(12) United States Patent
Park et al.

(10) Patent No.: US 11,512,076 B2
(45) Date of Patent: Nov. 29, 2022

(54) COMPOUND FOR ORGANIC ELECTRONIC ELEMENT, ORGANIC ELECTRONIC ELEMENT COMPRISING THE SAME, AND ELECTRONIC DEVICE THEREOF

(71) Applicant: DUK SAN NEOLUX CO., LTD., Cheonan-si (KR)

(72) Inventors: Jong Gwang Park, Cheonan-si (KR); Yun Suk Lee, Cheonan-si (KR); Jung Hwan Park, Cheonan-si (KR); Jung Wook Lee, Cheonan-si (KR); Sun Hee Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 417 days.

(21) Appl. No.: 16/636,375

(22) PCT Filed: Aug. 8, 2018

(86) PCT No.: PCT/KR2018/009008
§ 371 (c)(1),
(2) Date: Feb. 4, 2020

(87) PCT Pub. No.: WO2019/031833
PCT Pub. Date: Feb. 14, 2019

(65) Prior Publication Data
US 2020/0172524 A1    Jun. 4, 2020

(30) Foreign Application Priority Data
Aug. 9, 2017 (KR) .................. 10-2017-0101165

(51) Int. Cl.
C07D 409/10 (2006.01)
C07D 409/12 (2006.01)
(Continued)

(52) U.S. Cl.
CPC ......... *C07D 409/10* (2013.01); *C07D 409/12* (2013.01); *C07D 409/14* (2013.01);
(Continued)

(58) Field of Classification Search
None
See application file for complete search history.

(56) References Cited

U.S. PATENT DOCUMENTS

2010/0187511 A1* 7/2010 Funahashi ........... H01L 51/0061
257/E51.026
2011/0168990 A1* 7/2011 Tanaka ................ H01L 51/0074
257/E51.027
(Continued)

FOREIGN PATENT DOCUMENTS

KR   10-2009-0041999 A   4/2009
KR   10-2014-0035737 A   3/2014
(Continued)

*Primary Examiner* — Robert S Loewe
(74) *Attorney, Agent, or Firm* — The PL Law Group, PLLC

(57) ABSTRACT

Provided are a compound of Formula 1; an organic electric element comprising a first electrode, a second electrode, and an organic material layer formed between the first electrode and the second electrode, comprising a compound of Formula 1 in the organic material layer; and an electronic device comprising the element, which has lowered driving voltage and increased luminous efficiency and life time.

11 Claims, 1 Drawing Sheet

(51) Int. Cl.
*C07D 409/14* (2006.01)
*C07F 7/08* (2006.01)
*H01L 51/00* (2006.01)
*H01L 51/50* (2006.01)

(52) U.S. Cl.
CPC ........ *C07F 7/0803* (2013.01); *H01L 51/0058* (2013.01); *H01L 51/0061* (2013.01); *H01L 51/0067* (2013.01); *H01L 51/0073* (2013.01); *H01L 51/0074* (2013.01); *H01L 51/0005* (2013.01); *H01L 51/5056* (2013.01); *H01L 51/5072* (2013.01); *H01L 51/5092* (2013.01)

(56) References Cited

U.S. PATENT DOCUMENTS

| | | | | |
|---|---|---|---|---|
| 2016/0072091 | A1* | 3/2016 | Imada | H01L 51/5064 |
| | | | | 257/40 |
| 2016/0268516 | A1* | 9/2016 | Tanaka | C07D 471/06 |
| 2017/0301868 | A1* | 10/2017 | Lee | C07D 209/82 |

FOREIGN PATENT DOCUMENTS

| | | | |
|---|---|---|---|
| KR | 10-2015-0016896 A | 2/2015 | |
| KR | 10-2016-0013692 A | 2/2016 | |
| KR | 10-1614738 B1 | 4/2016 | |
| WO | WO-2016056757 A1 * | 4/2016 | ........... C07D 333/76 |

* cited by examiner

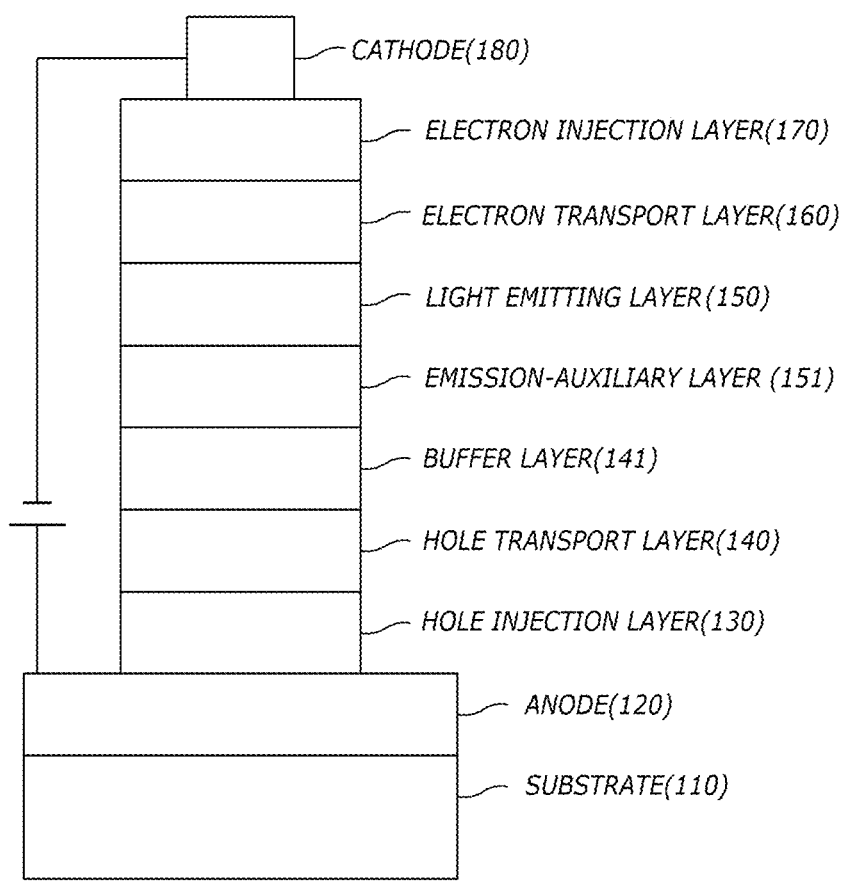

COMPOUND FOR ORGANIC ELECTRONIC ELEMENT, ORGANIC ELECTRONIC ELEMENT COMPRISING THE SAME, AND ELECTRONIC DEVICE THEREOF

CROSS-REFERENCE TO RELATED APPLICATION

This patent application claims priority from and the benefit under 35 U.S.C. § 119 to § 121, and § 365 of Korean Patent Application No. 10-2017-0101165, filed on Aug. 9, 2017, which is hereby incorporated by reference for all purposes as if fully set forth herein. Further, this application claims the benefit of priority in countries other than U.S., which is hereby incorporated by reference herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function.

Currently, the power consumption is required more and more as size of display becomes larger and larger in the portable display market. Therefore, the power consumption is a very important factor in the portable display with a limited power source of the battery, and efficiency and life span issue also must be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when energy levels and T1 values among the respective layers included in the organic material layer, inherent material properties (mobility, interfacial properties, etc.) and the like are optimal combination.

In addition, in the recent organic electroluminescent devices, an emission-auxiliary layer (multi-layered hole transport layer) must be present between the hole transport layer and the light emitting layer in order to solve the problems of luminescence in the hole transport layer and the driving voltage, and it is necessary to develop different emission-auxiliary layers according to respective light emitting layers.

In general, an electron is transferred from an electron transport layer to a light emitting layer and a hole is transferred from a hole transport layer to the light emitting layer, as a result, an exciton is formed by the recombination of the electron and hole within the light emitting layer.

However, material used in a hole transport layer has a low T1 value because the material should have a low HOMO value. As a result, the exciton generated in the light emitting layer is transferred to the hole transport layer and it causes charge unbalance in the light emitting layer, thereby emitting light at the interface of the hole transport layer.

When light is emitted from the interface of the hole transporting layer, the color purity and efficiency of the organic electronic element are lowered and the lifetime is shortened. Therefore, it is strongly desired to develop materials for the emission-auxiliary layer having a HOMO level between the HOMO energy level of the hole transporting layer and the HOMO energy level of the light emitting layer, a high T1 energy value and a hole mobility within a suitable driving voltage range (within a driving voltage range of blue element of a full device).

However, this cannot be achieved simply by the structural properties of the core of the emission-auxiliary layer material. An element having a high efficiency and a long life span can be realized when the characteristics of core and sub-substituents of the emission-auxiliary layer material, the proper combination of the emission-auxiliary layer and the hole transport layer, and the proper combination of the emission-auxiliary layer and the light emitting layer.

In order to fully exhibit the excellent characteristics of the organic electric element, materials forming the organic material layer in the element, such as a hole injection material, a hole transport material, a light emitting material, an electron transport material, an electron injection material, an emission-auxiliary layer material, etc. should be prerequisite to support by a stable and efficient material, and in particular, it is strongly required to develop material of an an emission-auxiliary layer.

Object, Technical Solution and Effects of the Invention

The object of the present invention is to provide a compound capable of lowering driving voltage of the device, and capable of improving luminous efficiency, color purity and lifespan, an organic electric element employing the same, and an electronic device thereof.

In accordance with an aspect of the present invention, the compound represented by the following formula is provided.

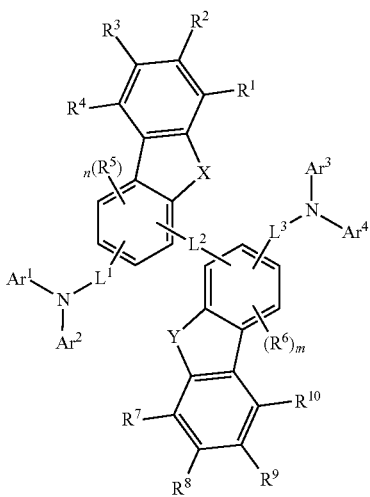

In another aspect of the present invention, organic electric element employing the compound represented by the above formula and an electronic device comprising the organic electric element are provided.

According to the present invention, by employing a compound according to one embodiment of the present invention, the driving voltage of a device can be lowered, and the luminous efficiency, color purity and lifespan of a device can be improved.

BRIEF DESCRIPTION OF THE DRAWINGS

The FIGURE illustrates an example of an organic light emitting diode according to an embodiment of the present invention: 100 is organic electric element, 110 is substrate, 120 is first electrode, 130 is hole injection layer, 140 is hole transport layer, 141 is buffer layer, 150 is light emitting layer, 151 is emission-auxiliary layer, 160 is electron transport layer, 170 is electron injection layer, and 180 is second electrode.

DETAILED DESCRIPTION

As used in the specification and the accompanying claims, unless otherwise stated, the meanings of the following terms are as follows.

Unless otherwise stated, the term "halo" or "halogen" as used herein includes fluorine (F), bromine (Br), chlorine (Cl), or iodine (I).

Unless otherwise stated, the term "alkyl" or "alkyl group" as used herein has a single bond of 1 to 60 carbon atoms, and means the saturated aliphatic functional radicals including a linear alkyl group, a branched chain alkyl group, a cycloalkyl group (alicyclic), a cycloalkyl group substituted with an alkyl group and an alkyl group substituted with a cycloalkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

Unless otherwise stated, the term "alkoxyl group", "alkoxy group" or "alkyloxy group" as used herein means oxygen radical attached to an alkyl group, but not limited to, and has 1 to 60 carbon atoms.

Unless otherwise stated, the term "aryloxyl group" or "aryloxy group" as used herein means oxygen radical attached to an aryl group, but not limited to, and has 6 to 60 carbon atoms.

Unless otherwise stated, the term "fluorenyl group" or "fluorenylene group" as used herein means univalent or bivalent functional group in which R, R' and R" are all hydrogen in the following structure, "substituted fluorenyl group" or "substituted fluorenylene group" means that at least any one of R, R' and R" is a substituent other than hydrogen, and it comprises the case where R and R' are bonded to each other to form the spiro compound together with the carbon to which they are bonded.

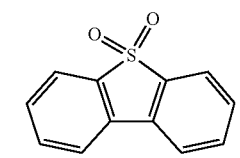 [SMILES: O=S1(=O)c2ccccc2-c2ccccc21]

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents N, O, S, P or Si. The heterocyclic group means a monocyclic, ring assemblies, fused polycyclic system or spiro compound containing one or more heteroatoms.

Also, the term "heterocyclic group" may comprise a ring including $SO_2$ instead of carbon consisting of a ring. For example, "heterocyclic group" includes the following compound.

The term "ring" as used herein means, a monocyclic and polycyclic, an aliphatic ring and heterocyclic group containing at least one heteroatom, and an aromatic ring and a non-aromatic ring.

The term "polycyclic ring" as used herein may comprise ring assemblies such as biphenyl and terphenyl, fused polycyclic system and a spiro compound, an aromatic ring and a non-aromatic ring, and an aliphatic ring and heterocyclic group containing at least one heteroatom.

The term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

The term "fused polycyclic system" as used herein means, fused ring type which has at least two atoms as the common members, fused two or more aliphatic ring systems and a fused hetero ring system containing at least one heteroatom. Fused polycyclic system is an aromatic ring, a hetero aromatic ring, an aliphatic ring, or a combination thereof.

The term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group containing at least one heteroatom selected from the group consisting of O, N, S, Si, and P, but there is no limitation thereto.

A 'group name' comprised in an aryl group, an arylene group, a heterocyclic group and the like as example of each symbol and a substituent as used herein may be written in the name of functional group reflecting the valence, and may also be described as the name of a parent compound. For example, in the case of phenanthrene which is a kind of aryl group, it may be described by distinguishing valence such as 'phenanthryl' when it is 'monovalent group', and as 'phenanthrylene' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl group when it is monovalent group, and as pyrimidylene group when it is divalent group.

Otherwise specified, the formulas used in the present invention are as defined in the index definition of the substituent of the following formula.

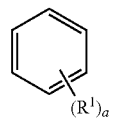

In the above formula, where a is an integer of zero, the substituent $R^1$ is absent, that is, hydrogen atoms are bonded to all the carbon constituting the benzene ring. Here, chemical formulas or compounds may be written without explicitly describing the hydrogen. In addition, one substituent $R^1$ is bonded to any carbon of the carbons forming the benzene ring when "a" is an integer of 1. Similarly, where "a" is an integer of 2 or 3, substituents $R^1$s may be bonded to the carbon of the benzene ring, for example, as followings. Also, where "a" is an integer of 4 to 6, substituents $R^1$s are bonded to the carbon of the benzene ring in a similar manner. Further, where "a" is an integer of 2 or more, $R^1$s may be the same or different from each other.

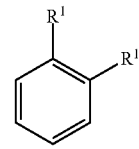

(a=2)

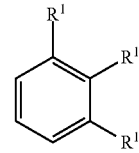

(a=3)

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer formed between the first electrode 120 and the second electrode 180 and comprising the compound of the present invention. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may be omitted, or the organic material layer may further include a hole blocking layer, an electron blocking layer, an emission-auxiliary layer 151, the electron transport-auxiliary layer, a buffer layer 141, etc., the electron transport layer 160 or the like may serve as the hole blocking layer.

Although not shown, the organic electric element according to an embodiment of the present invention may further include a protective layer or a layer (Capping layer) for improving luminous efficiency formed on at least one side of sides of the first electrode and the second electrode, wherein at least one side is not facing the organic material layer.

The inventive compound employed in the organic material layer may be used as a material of a hole injection layer 130, a hole transport layer 140, an emission-auxiliary layer 151, an electron transport auxiliary layer, an electron transport layer 160, an electron injection layer 170, as host or dopant of a light emitting layer 150, or as a material of a layer for improving luminous efficiency. For example, the inventive compound may be used as material of the light emitting layer 150, the hole transport layer 140 and/or the emission-auxiliary layer 151.

On the other hand, even if the core is the same core, the band gap, the electrical characteristics, the interface characteristics and the like may be different depending on which substituent is bonded at which position. Therefore, it is necessary to study the selection of the core and the combination of the core and the sub-substituent bonded to the core. In particular, long life span and high efficiency can be simultaneously achieved when the optimal combination of energy levels and $T_1$ values, inherent material properties (mobility, interfacial properties, etc.), and the like among the respective layers of an organic material layer is achieved.

Therefore, according to the present invention, energy level and $T_1$ value between the respective layers of the organic material layer, inherent material properties (mobility, interfacial properties, etc.) and the like can be optimized by forming an emission-auxiliary layer 151 with the compound represented by the Formula 1, and thus it is possible to simultaneously improve the life span and efficiency of the organic electric element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150, and an electron transport auxiliary layer may be formed between a light emitting layer 150 and an electron transport layer 160.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

WOLED (White Organic Light Emitting Device) has advantages of high resolution realization, an excellent processability, and being produced by using conventional color filter technologies for LCDs. Various structures for WOLED which mainly used as back light units have been suggested and patented. WOLED may employ various arrangement methods, representatively, a parallel side-by-side arrangement method of R (Red), G (Green), B (Blue) light-emitting units, a vertical stack arrangement method of RGB light-emitting units, and a CCM (color conversion material) method in which electroluminescence from a blue (B) organic light emitting layer, and the present invention may be applied to such WOLED.

Also, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, the compound according to an aspect of the present invention will be described.

The compound according to an aspect of the present invention is represented by formula 1 below.

<Formula 1>

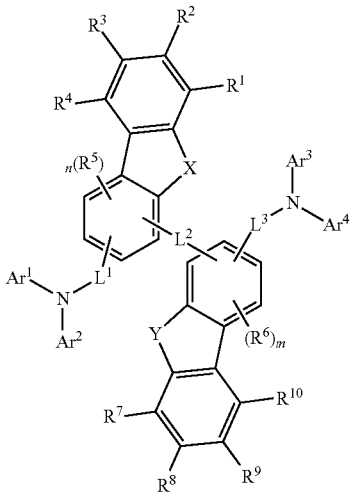

In the formula 1, each of symbols may be defined as follows.

X and Y are each independently O or S.

$L^1$ and $L^3$ may be each independently selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, and a fused ring group formed by a $C_3$-$C_{60}$ aliphatic ring with a $C_6$-$C_{60}$ aromatic ring, and $L^2$ may be selected from the group consisting of a $C_6$-$C_{60}$ arylene group, a fluorenylene group, a $C_2$-$C_{60}$ heterocyclic group containing at least one heteroatom selected from the group consisting of O, N, S, Si, and P, and a fused ring group formed by a $C_3$-$C_{60}$ aliphatic ring with a $C_6$-$C_{60}$ aromatic ring.

Where $L^1$ to $L^3$ are each arylene group, $L^1$ to $L^3$ may be preferably a $C_6$-$C_{30}$ arylene group, more preferably a $C_6$-$C_{18}$ arylene group, for example, phenyl, biphenyl, phenylnaphthalene or the like. Where $L^1$ to $L^3$ are a heterocyclic group, $L^1$ to $L^3$ may be preferably a $C_2$-$C_{30}$ heterocyclic group, more preferably a $C_2$-$C_{16}$ heterocyclic group, for example, dibenzothiophene, benzonaphthofuran, dibenzofuran, or the like.

$Ar^1$ to $Ar^4$ may be each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group formed by a $C_3$-$C_{60}$ aliphatic ring with a $C_6$-$C_{60}$ aromatic ring, a $C_6$-$C_{30}$ aryloxy group and -L'-N($R_a$)($R_b$).

Where $Ar^1$ to $Ar^4$ are each an aryl group, $Ar^1$ to $Ar^4$ may be preferably a $C_6$-$C_{30}$ aryl group, more preferably a $C_6$-$C_{18}$ aryl group, for example, phenyl, biphenyl, naphthyl, phenanthrene, triphenylene, terphenyl, phenylnaphthalene, anthracene or the like. Where $Ar^1$ to $Ar^4$ are each a heterocyclic group, $Ar^1$ to $Ar^4$ may be preferably a $C_2$-$C_{30}$ heterocyclic group, more preferably a $C_2$-$C_{20}$ heterocyclic group, for example, pyridine, dibenzothiophene, dibenzofuran, isoquinoline, carbazole, phenylcarbazole, benzo[b]benzo[4,5]thieno[2,3-d]thiophene, benzonaphthothiophene and the like. Where $Ar^1$ to $Ar^4$ are each a fluorenyl group, $Ar^1$ to $Ar^4$ may be 9,9-dimethylfluorene, 9,9-diphenylfluorene, 9,9'-spirobifluorene and the like.

$R^1$ to $R^{10}$ may be each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and adjacent groups may be optionally linked to each other to form a ring.

The ring formed by linking between adjacent $R^1$ and $R^2$, between adjacent $R^2$ and $R^3$, between adjacent $R^3$ and $R^4$, between adjacent $R^7$ and $R^8$, between adjacent $R^8$ and $R^9$, between adjacent $R^9$ and $R^{10}$, between adjacent $R^5$s, and/or between adjacent $R^6$s may be a $C_6$-$C_{60}$ aromatic ring group, a fluorenyl group, a $C_2$-$C_{60}$ heterocyclic group containing at least one heteroatom selected from the group consisting of O, N, S, Si, and P, or a fused ring group formed by a $C_3$-$C_{60}$ aliphatic ring with a $C_6$-$C_{60}$ aromatic ring and the like, preferably, the ring is a $C_6$-$C_{20}$ aromatic ring group or a $C_2$-$C_{20}$ heterocyclic group, for example, benzene, naphthalene, phenanthrene and the like.

m and n are each an integer of 0 to 2. Where m is an integer of 2 or more, a plurality of $R^5$s are the same as or different from each other, and where n is an integer of 2 or more, a plurality of $R^6$s are the same as or different from each other.

The above L' may be selected from the group consisting of a single bond, a $C_6$-$C_{60}$ arylene group, a fluorenylene group, and a $C_2$-$C_{60}$ heterocyclic group containing at least one heteroatom selected from the group consisting of O, N, S, Si, and P, and a fused ring group formed by a $C_3$-$C_{60}$ aliphatic ring with a $C_6$-$C_{60}$ aromatic ring.

The above $R_a$ and $R_b$ may be each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, and a fused ring group formed by a $C_3$-$C_{60}$ aliphatic ring with a $C_6$-$C_{60}$ aromatic ring.

Where the above symbols are each an aryl group, an arylene group, a fluorenyl group, a fluorenylene group, a heterocyclic group, a fused ring group, an alkyl group, an alkenyl group, an alkynyl group, an alkoxyl group or an aryloxy group, or where adjacent groups among $R^1$ to $R^{10}$ are linked to each other to form a ring, the aryl group, the arylene group, the fluorenyl group, the fluorenylene group, the heterocyclic group, the fused ring group, the alkyl group, the alkenyl group, the alkynyl group, the alkoxyl group, the aryloxyl group, or the ring formed by adjacent groups are each optionally substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, a $C_8$-$C_{20}$ arylalkenyl group and a combination thereof.

With the proviso that when $L^2$ is a $C_6$ arylene group, the case where $L^2$ is a $C_6$ arylene group substituted with a carbazole derivative, in particular, benzocarbazole is excluded from Formula 1. That is, the following compound is excluded from Formula 1.

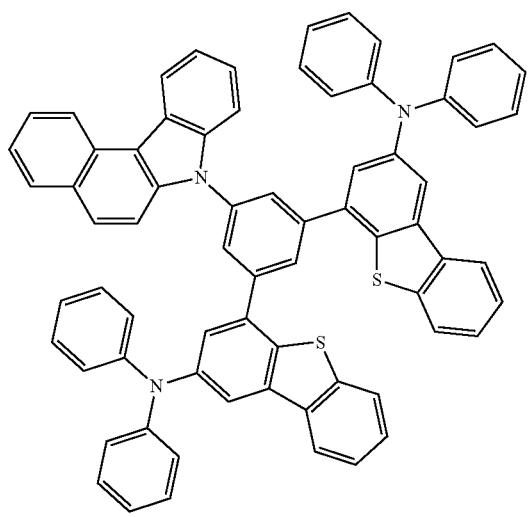 [SMILES: c1ccc(N(c2ccccc2)c2cc(-c3cc(-c4cc(N(c5ccccc5)c5ccccc5)cc5c4sc4ccccc45)cc(-n4c5ccccc5c5c6ccccc6ccc54)c3)c3sc4ccccc4c3c2)cc1]
Formula 1 may be represented by one of the Formulas 2 to 10.
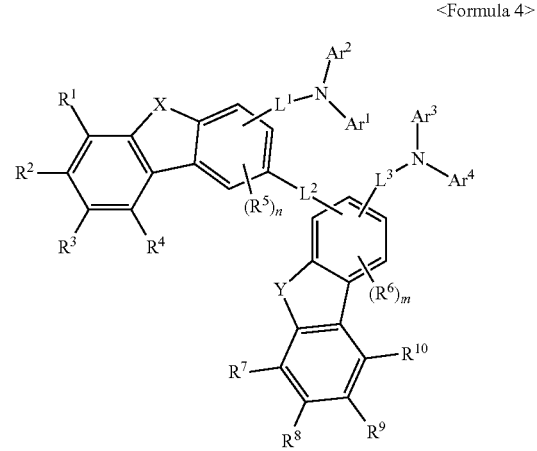
<Formula 4>
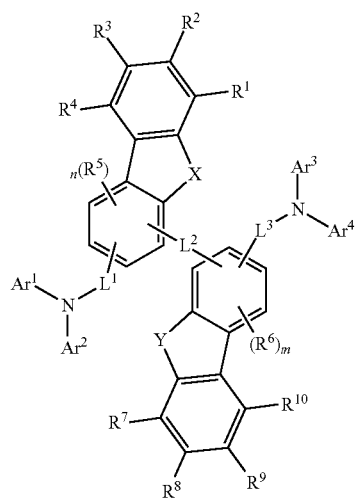
<Formula 2>
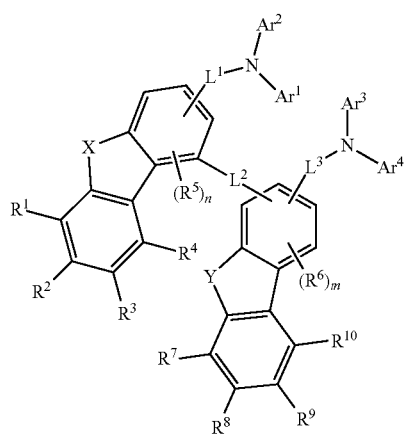
<Formula 5>
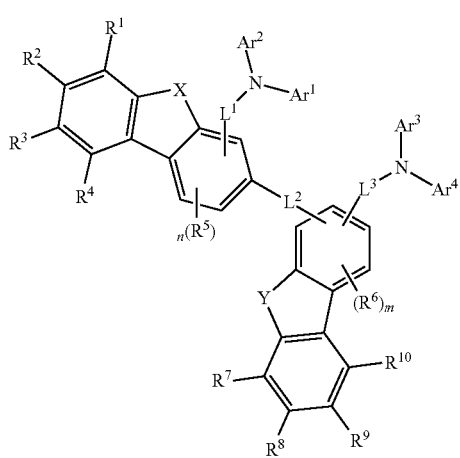
<Formula 3>
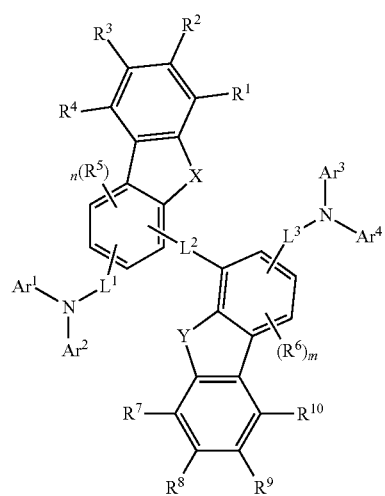
<Formula 6>

<Formula 7>
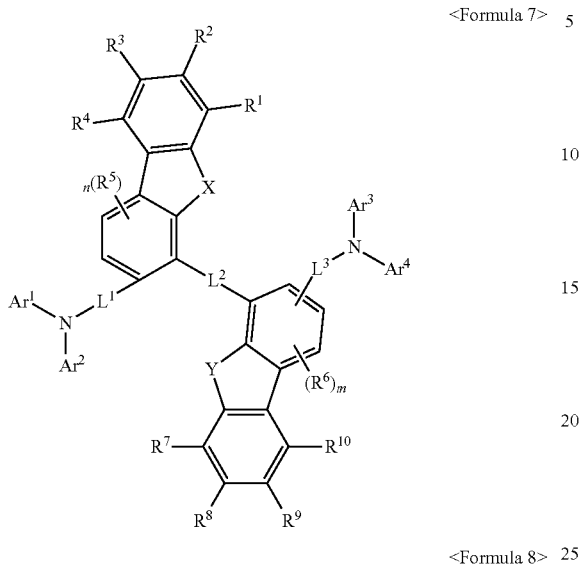
<Formula 8>
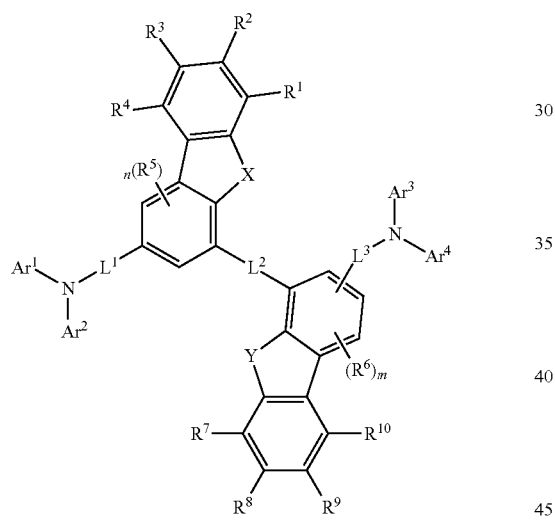
<Formula 9>
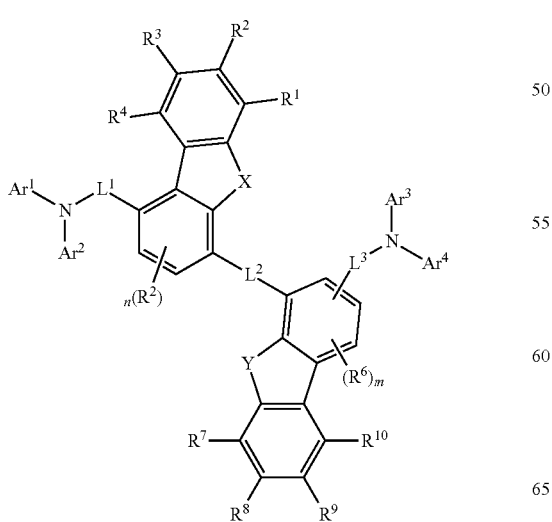
<Formula 10>
In the formulas 2 to 10, X, Y, $L^1$ to $L^3$, $Ar^1$ to $Ar^4$, $R^1$ to $R^{10}$, m and n are the same as defined in Formula 1.
In the formula 1, $L^1$ to $L^3$ are each independently represented by one of Formulas A-1 to A-13.
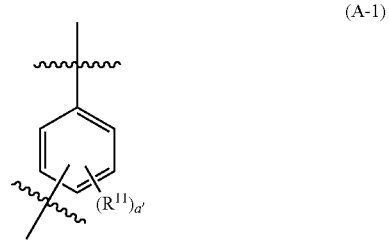
(A-1)
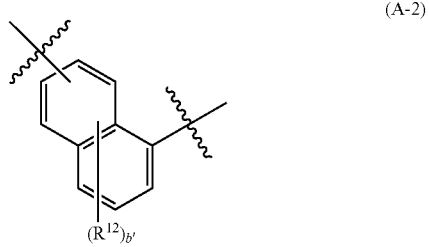
(A-2)
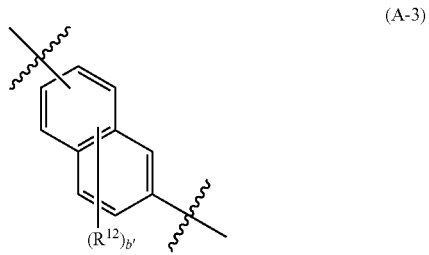
(A-3)

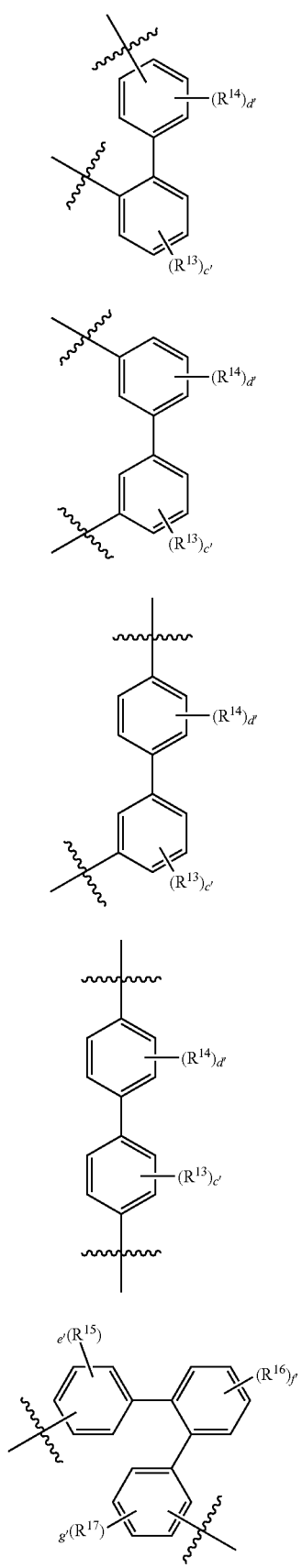

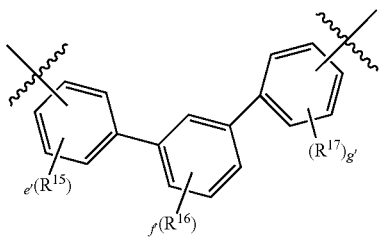

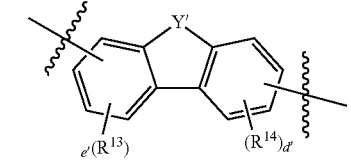

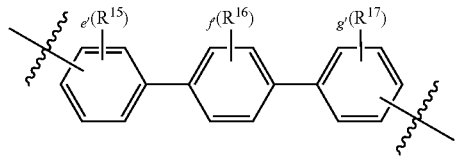

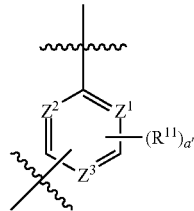

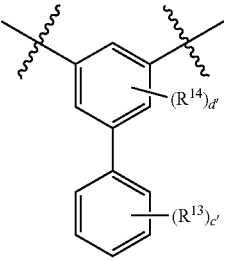

In the formulas A-1 to A-13, each of symbols may be defined as follows.

a', c', d', e', f' and g' are each an integer of 0 to 4, b' is an integer of 0 to 6.

$R^{11}$ to $R^{17}$ are each independently selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, and adjacent groups may be optionally linked to each other to form a ring.

Y' is N(R'), O, S or C(R')(R'').

$Z^1$ to $Z^3$ are each independently C, C(R') or N, and at least one of them is N.

R' and R'' are each independently selected from the group consisting of hydrogen, deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, and R' and R'' may be optionally linked to each other to form a ring.

The compound represented by formula 1 may be one of the following compounds.

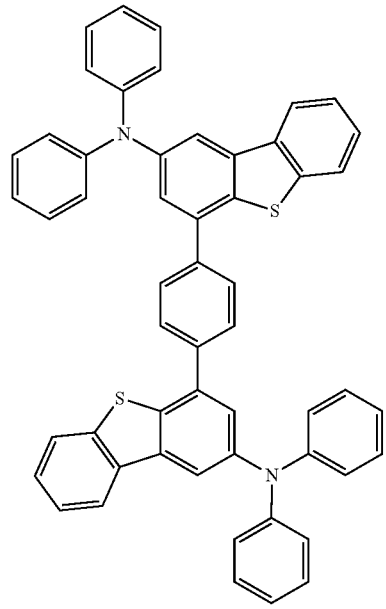

P-1

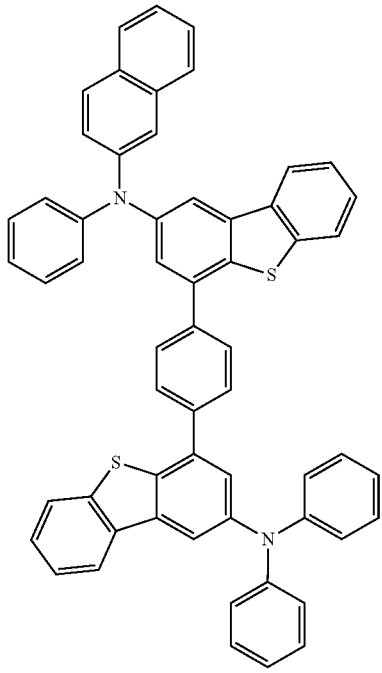

P-2

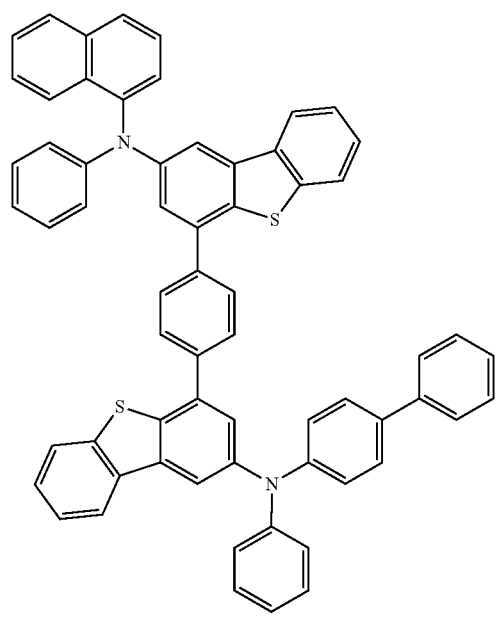

P-3

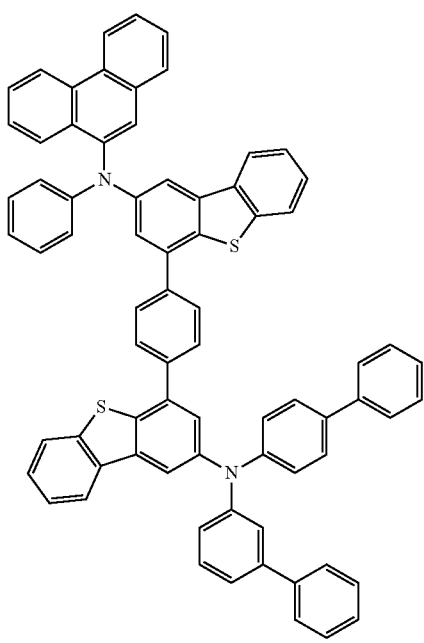

P-4

P-5
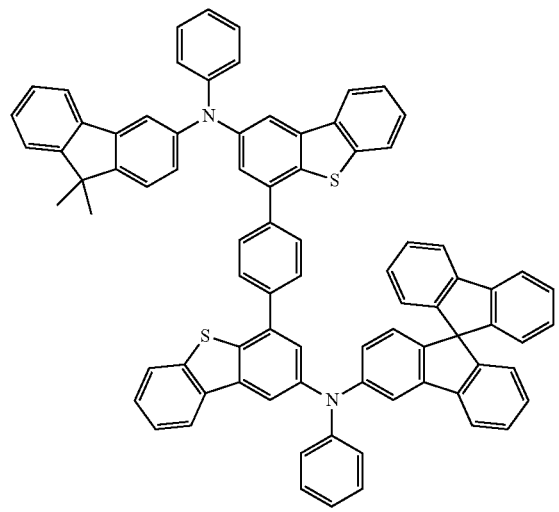
P-6
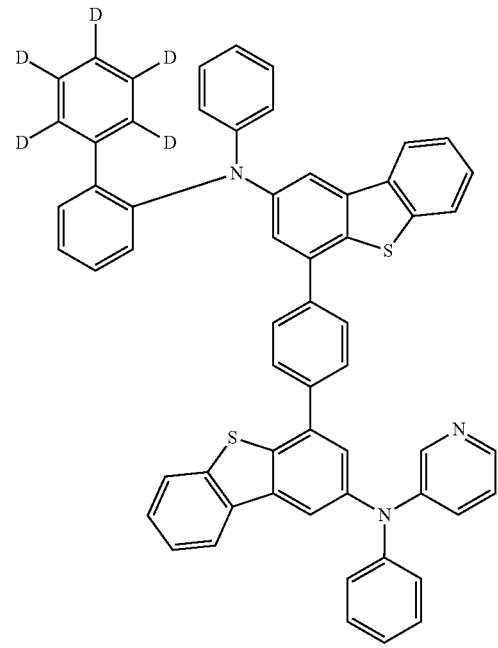
P-7
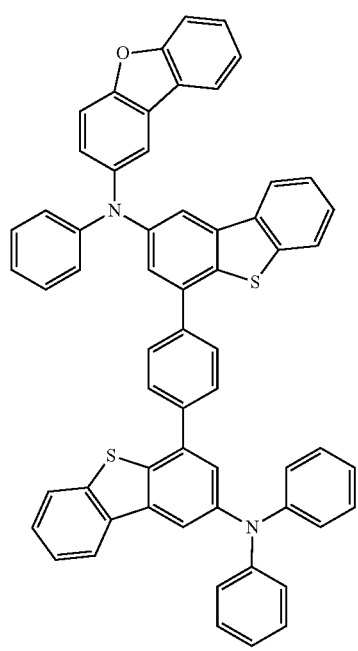
P-8
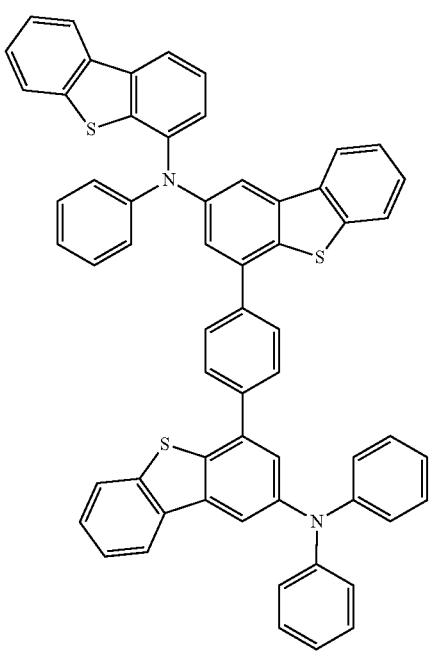

P-9
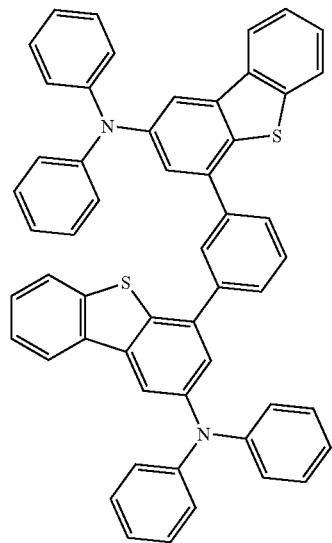
P-10
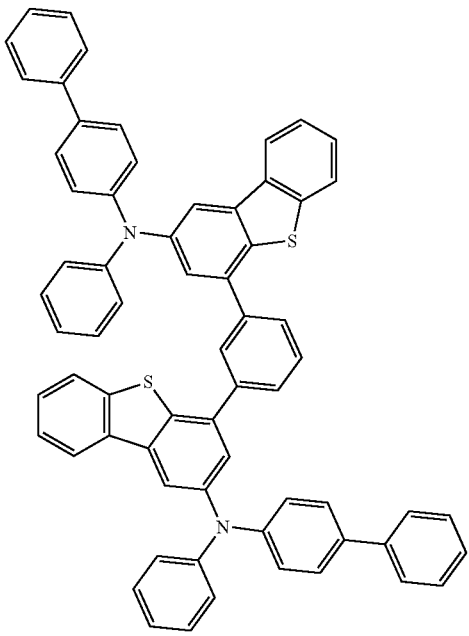
P-11
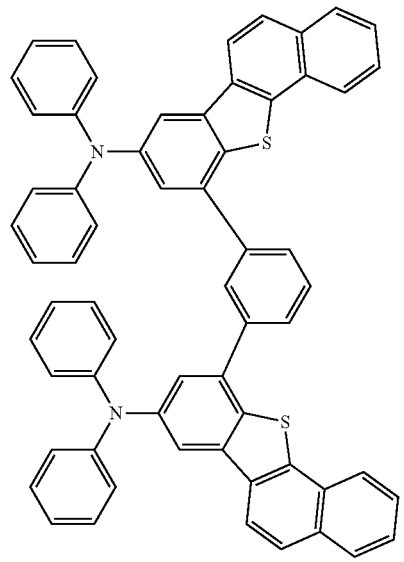
P-12
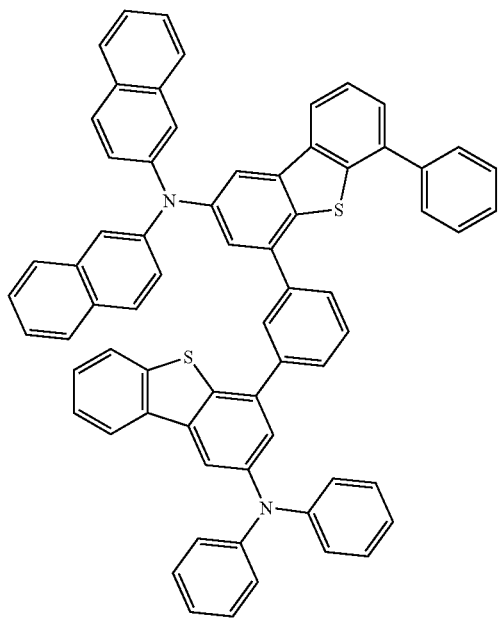

-continued
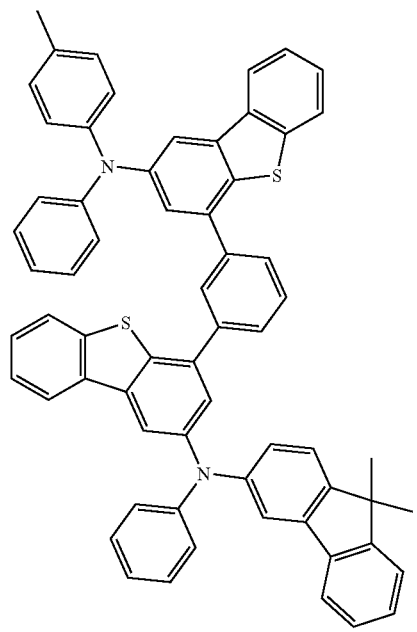
P-13
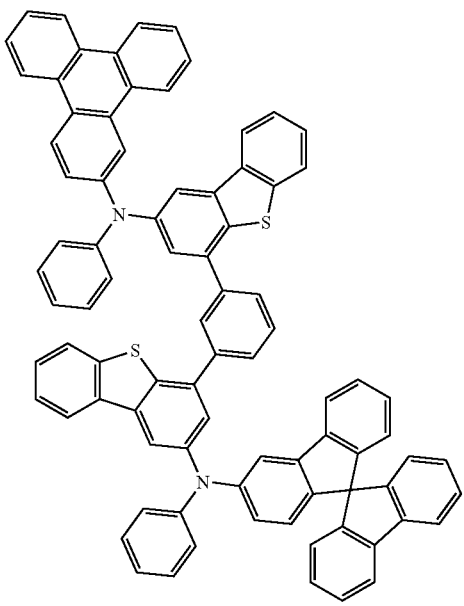
P-14
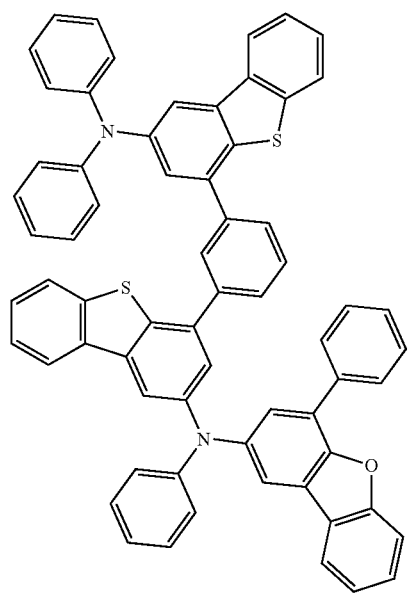
P-15
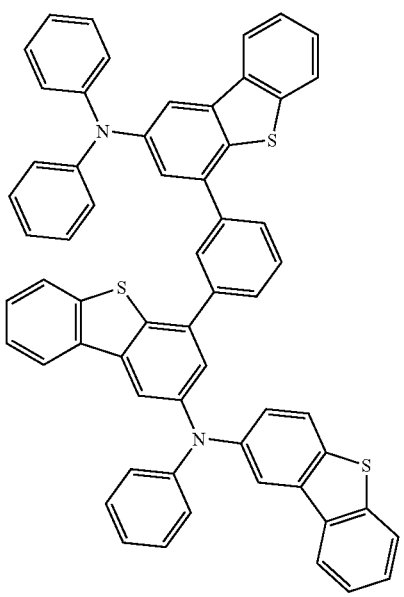
P-16

-continued
P-17
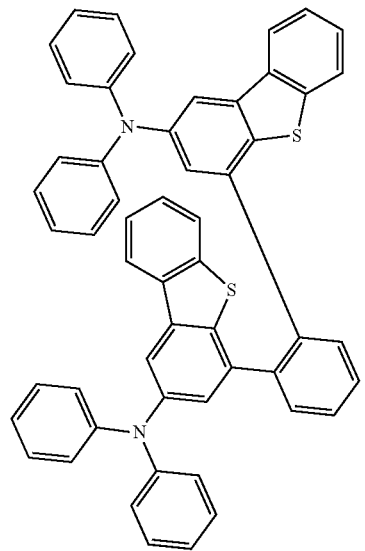
P-18
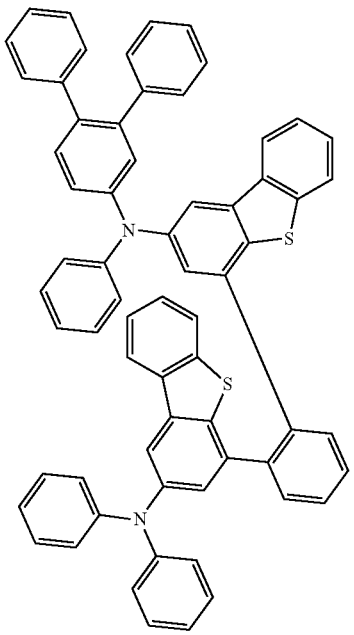
P-19
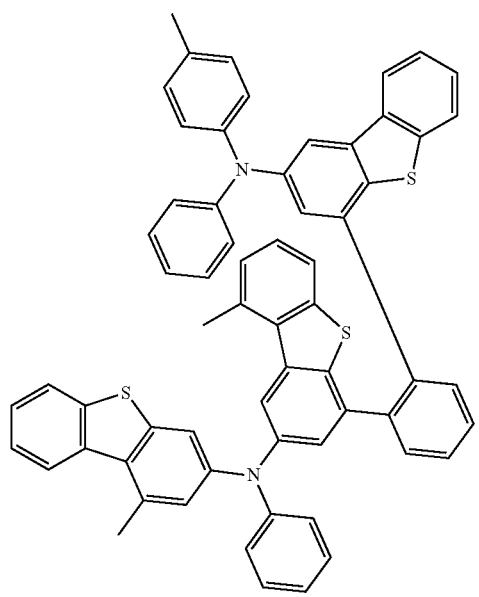
P-20
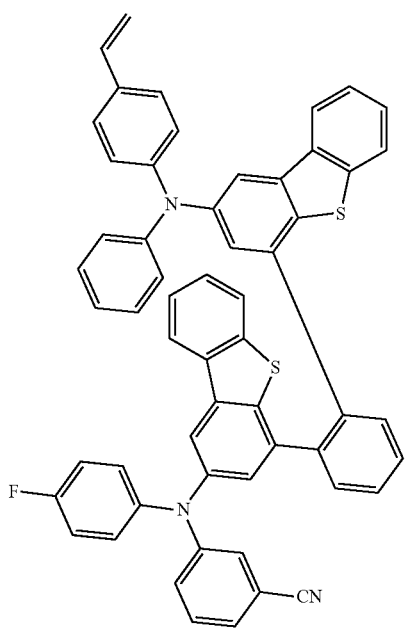

-continued
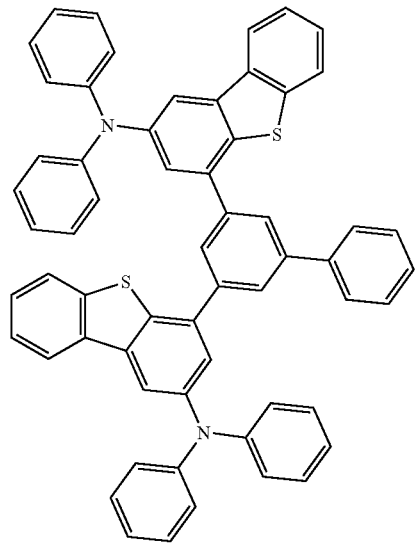
P-21
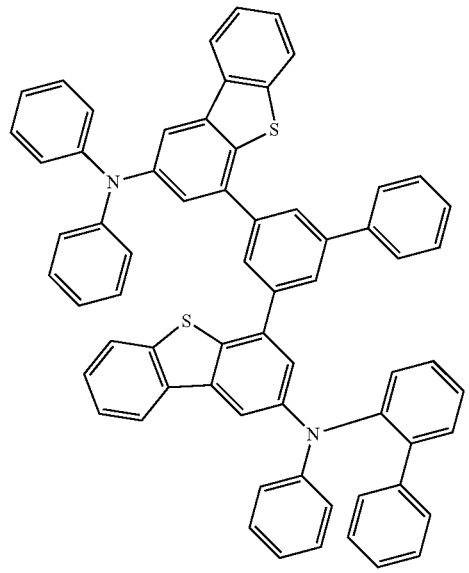
P-22
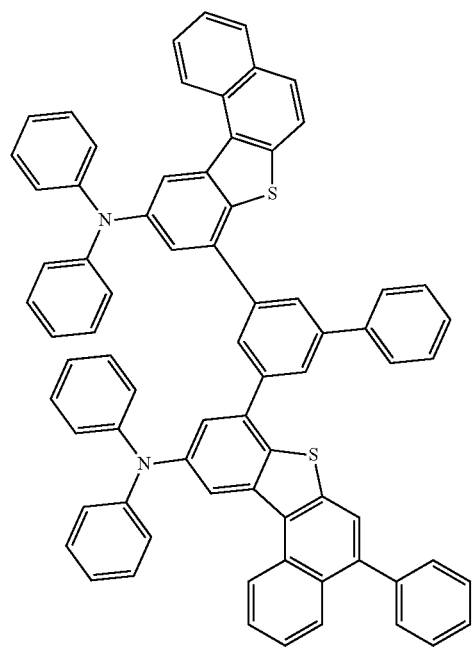
P-23
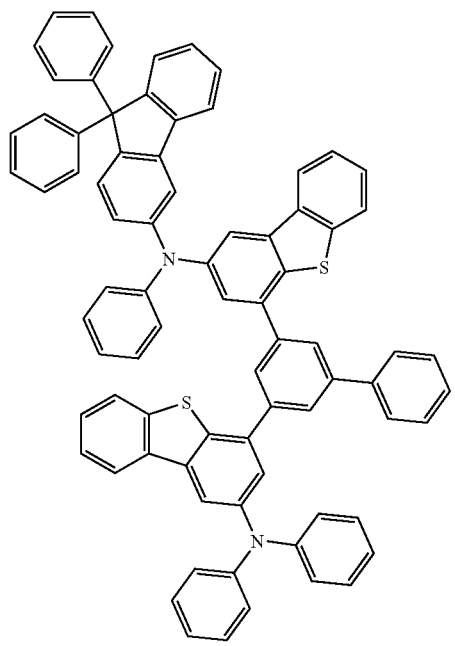
P-24

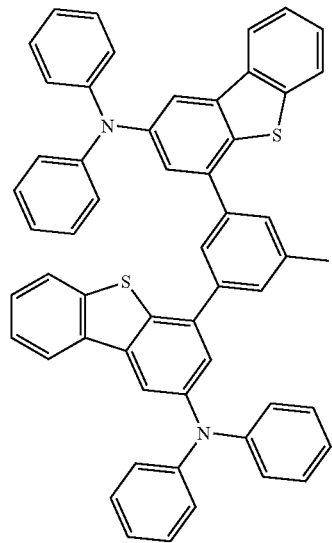
P-25
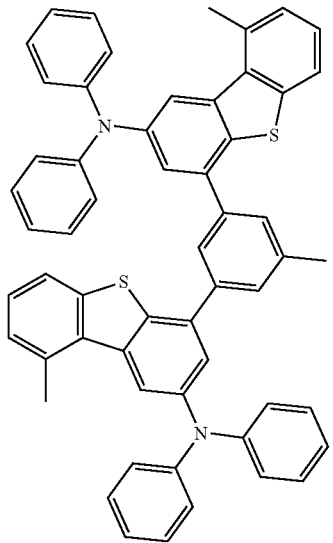
P-26
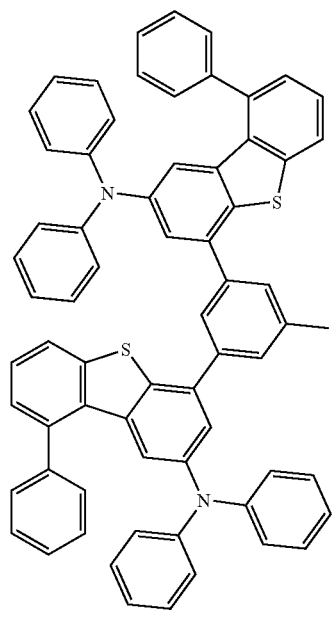
P-27
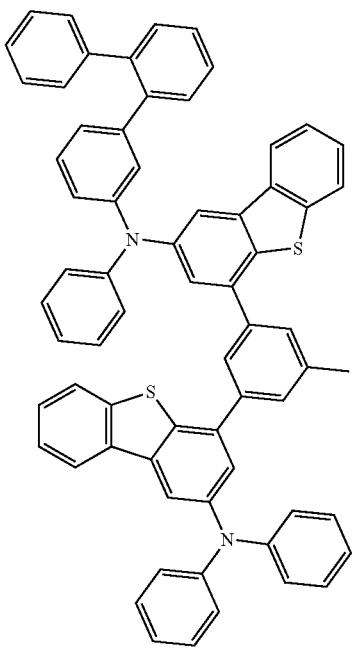
P-28

P-29
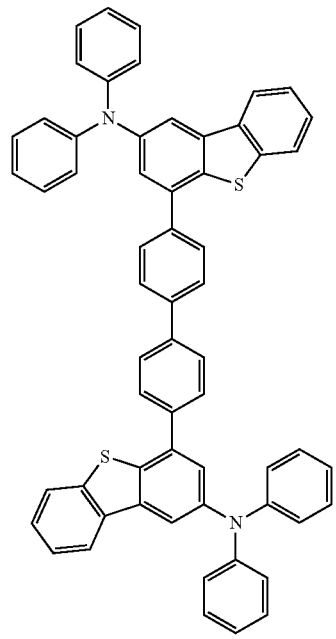
P-30
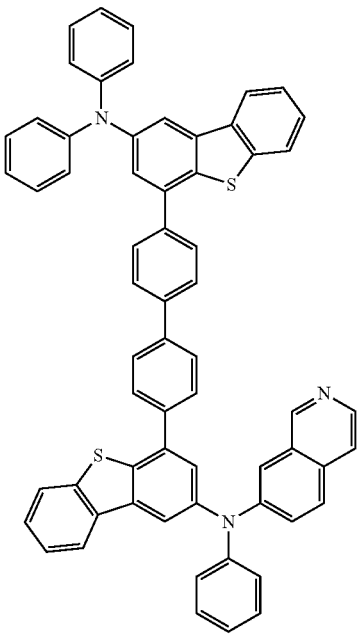
P-31
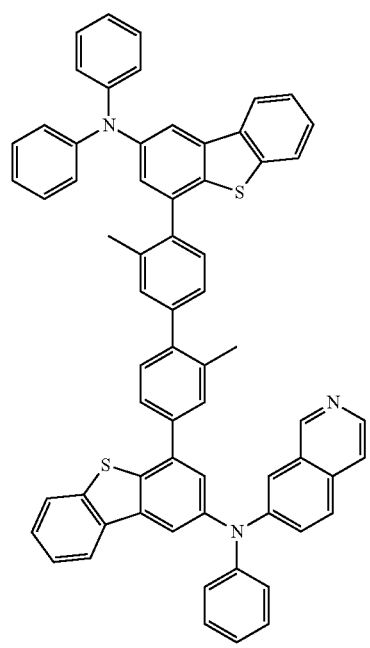
P-32
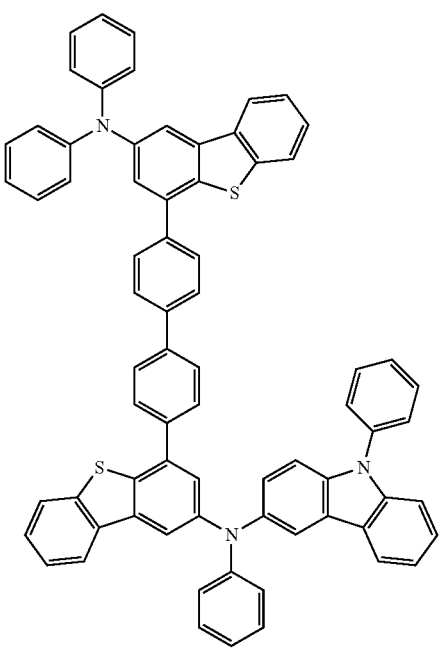

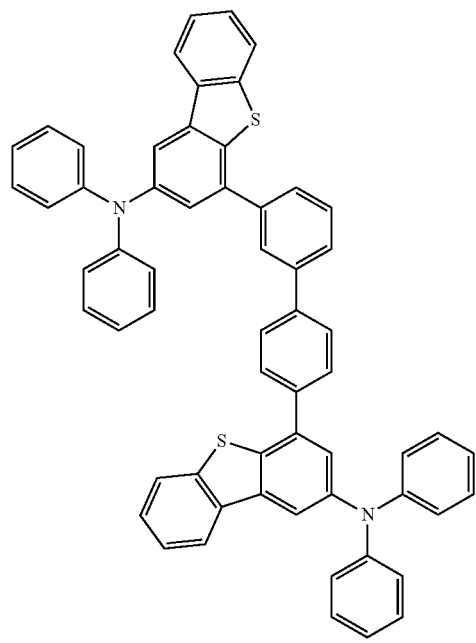
P-33
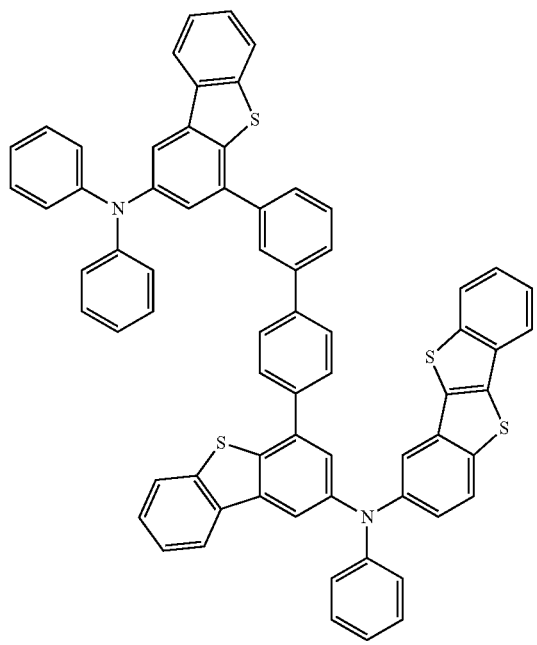
P-34
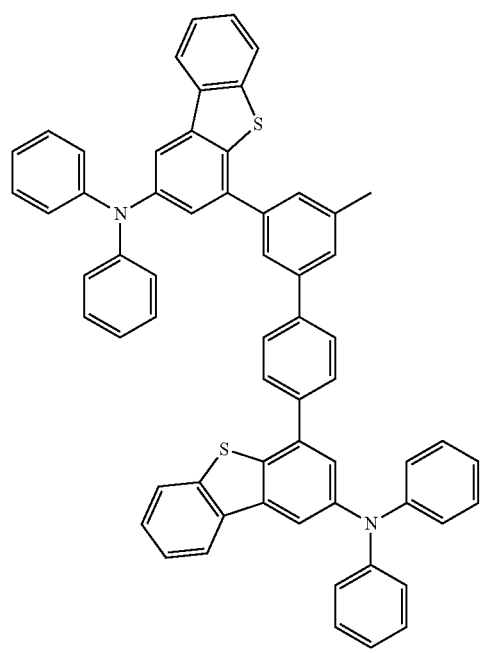
P-35
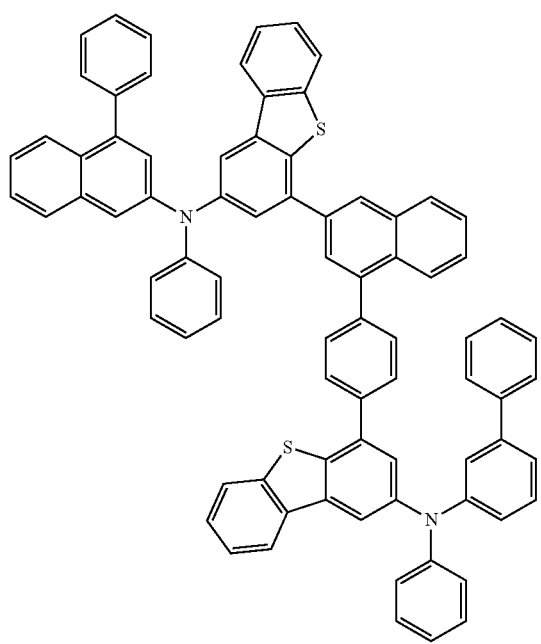
P-36

P-37
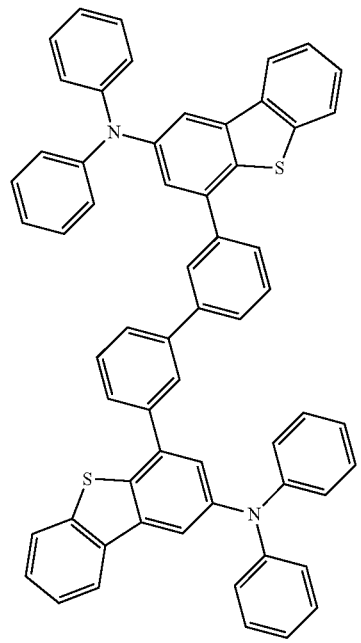
P-38
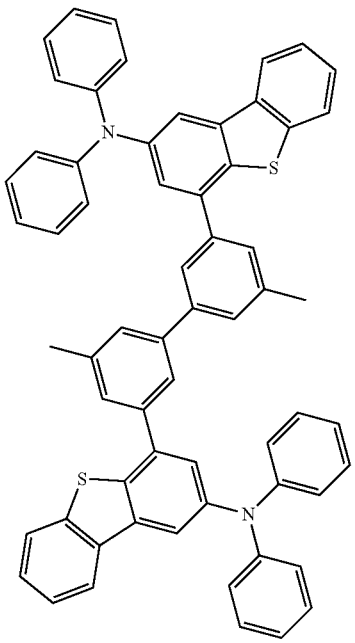
P-39
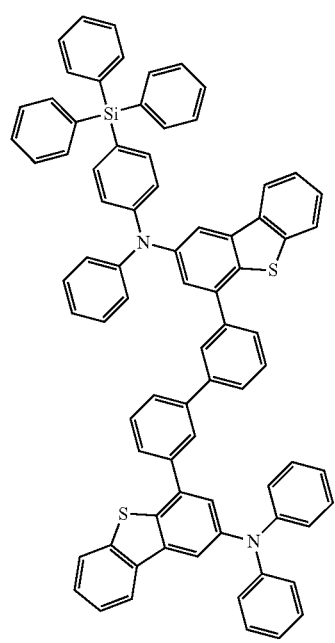
P-40
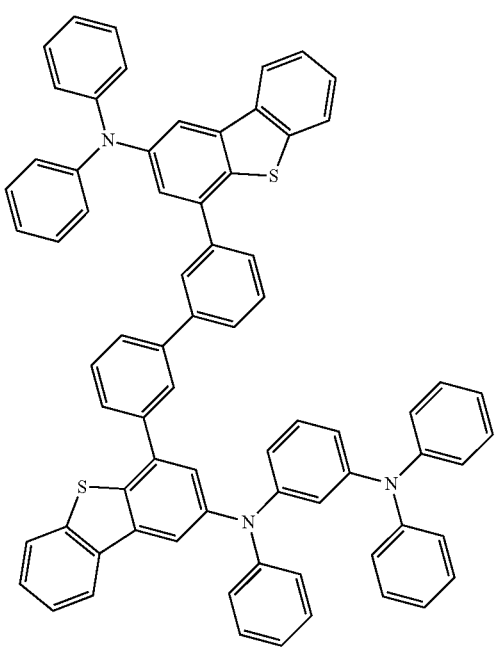

-continued
P-41
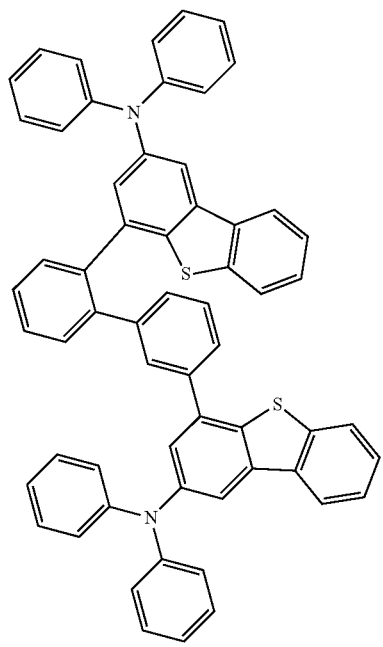
P-42
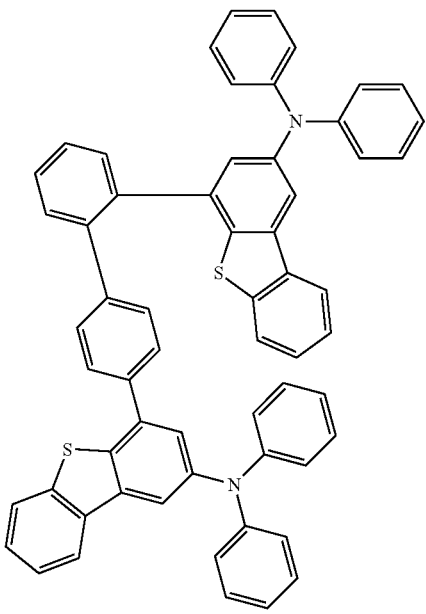
P-43
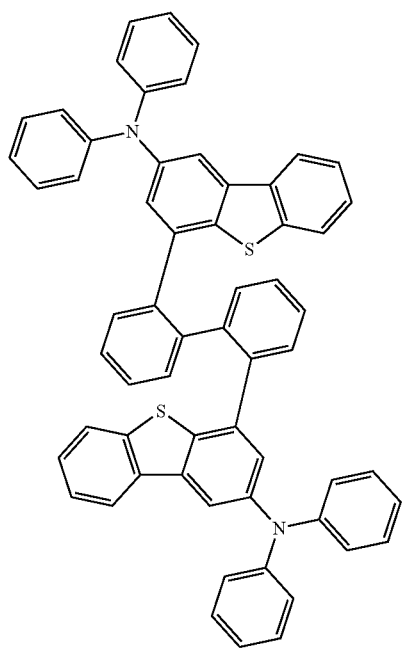
P-44
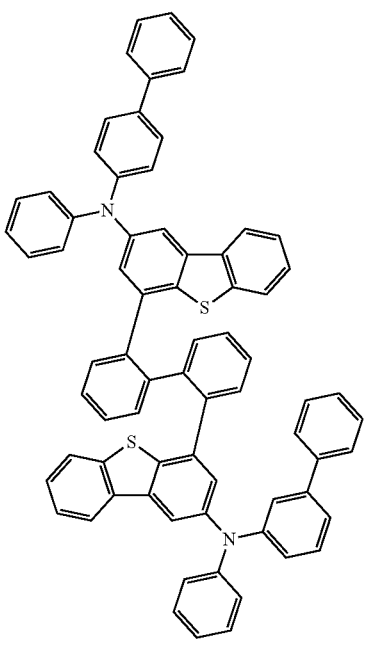

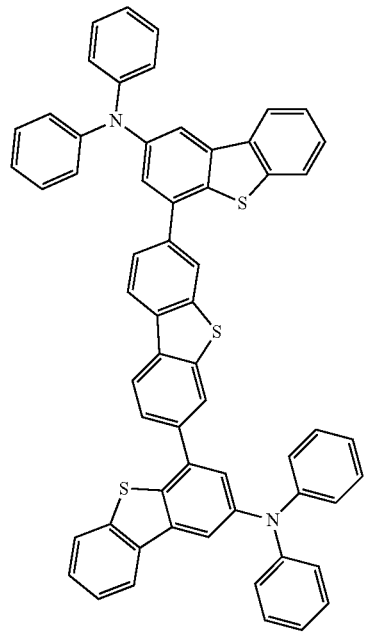
P-45
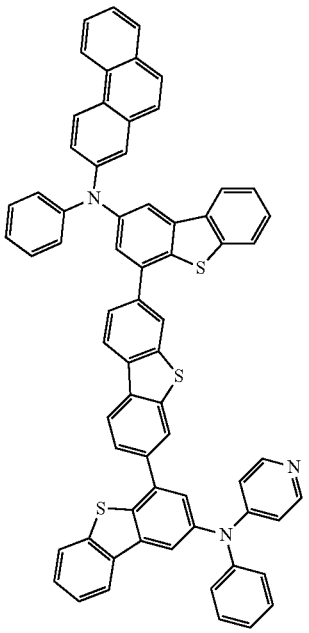
P-46
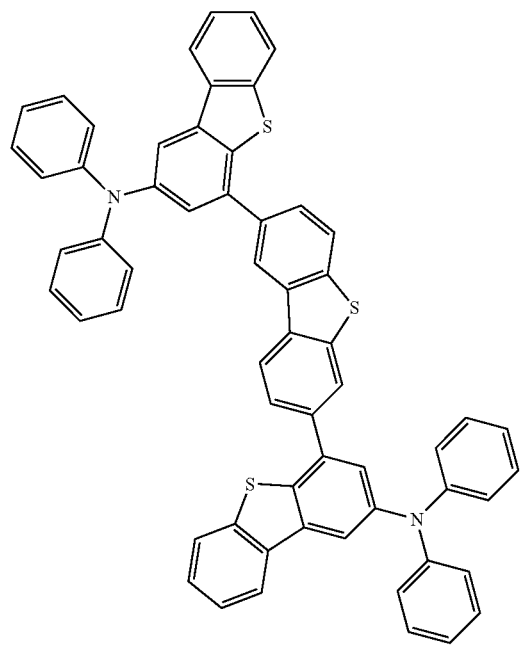
P-47
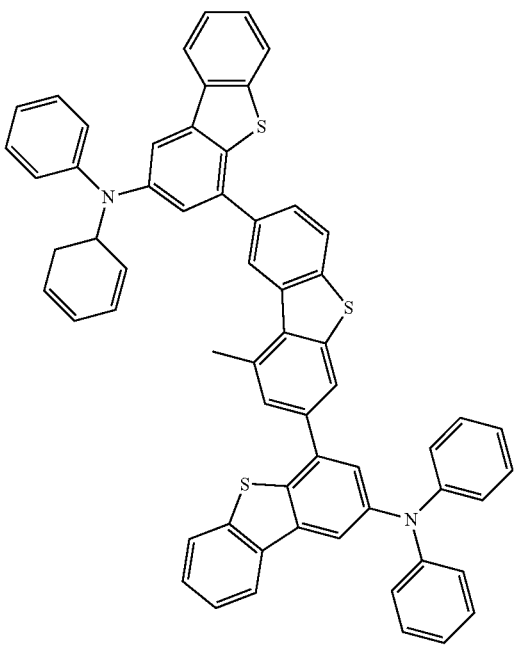
P-48

P-49
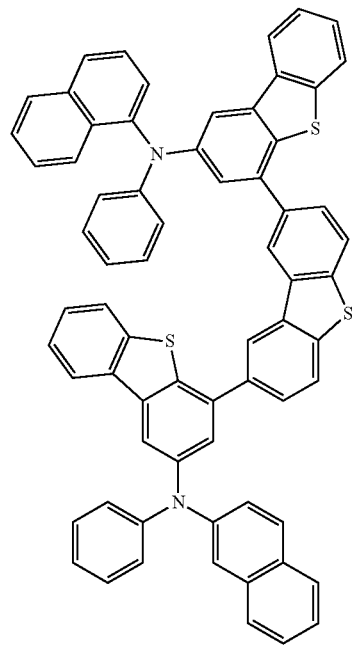
P-50
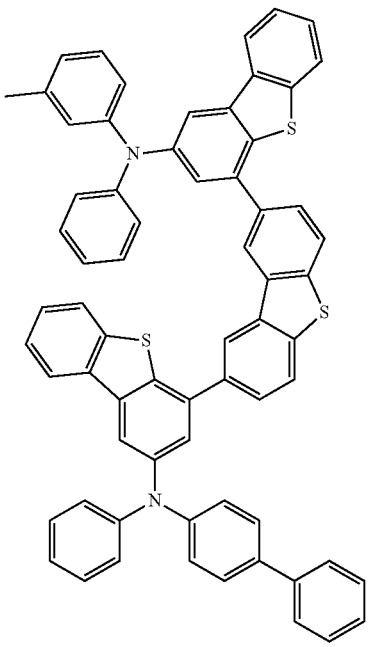
P-51
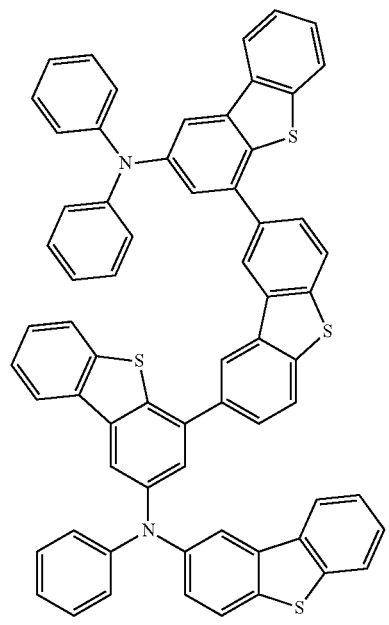
P-52
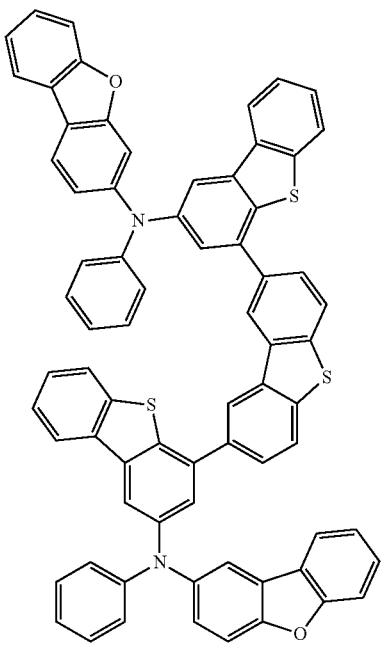

-continued
P-53
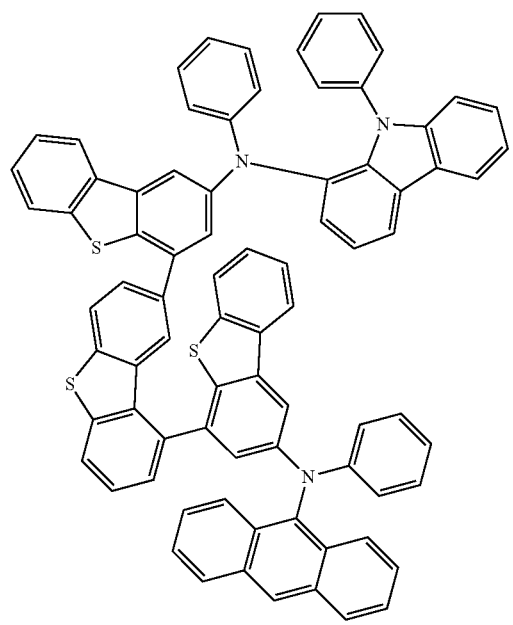
P-54
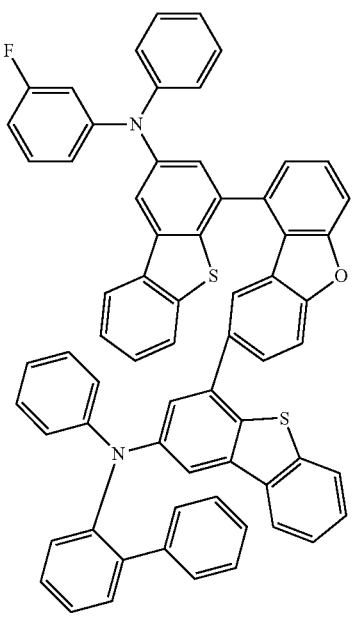
P-55
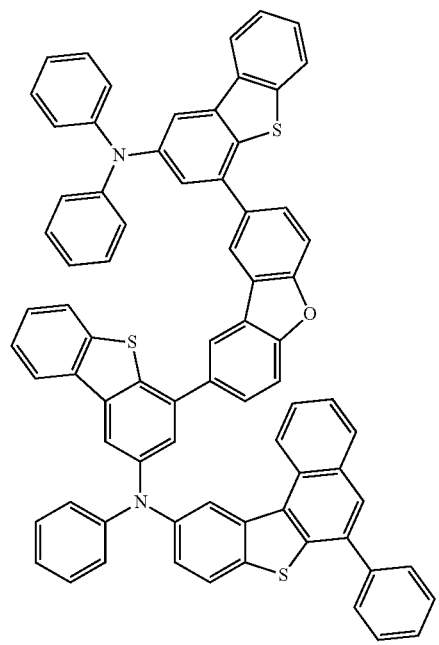
P-56
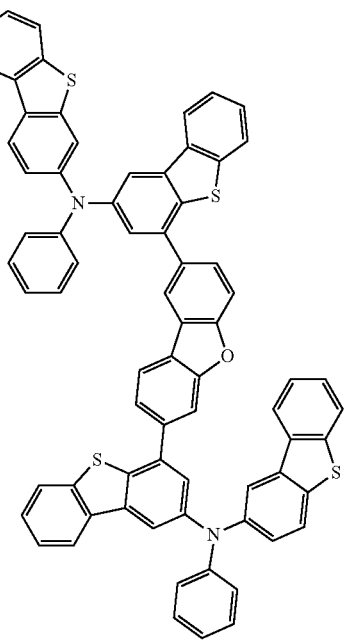

P-57
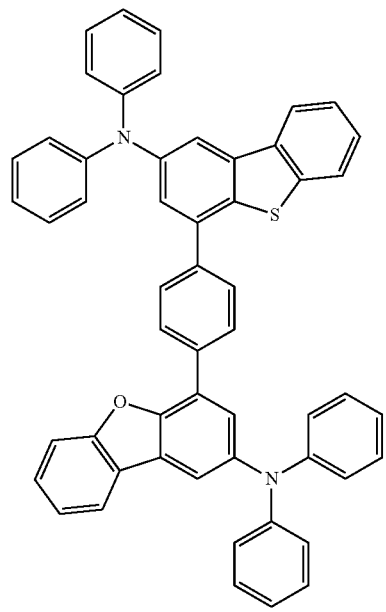
P-58
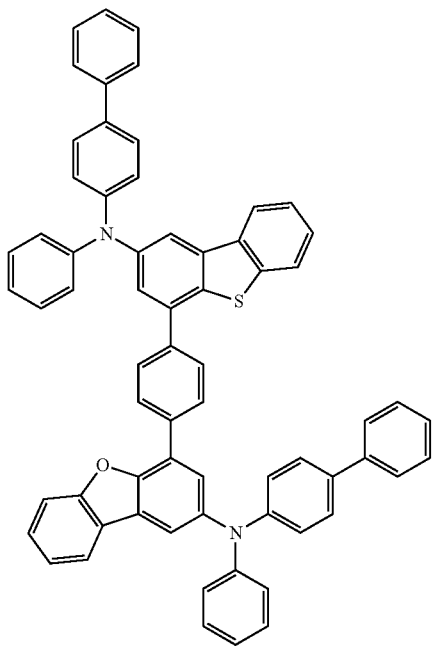
P-59
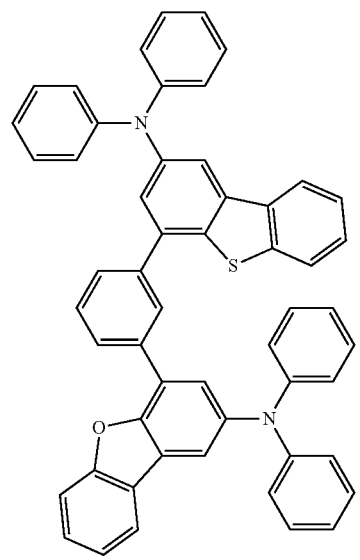
P-60
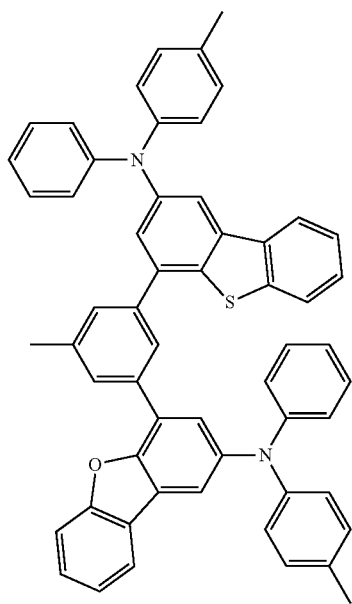

P-61
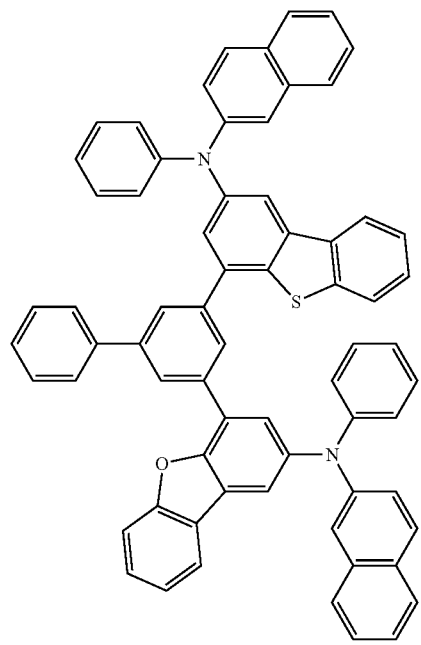
P-62
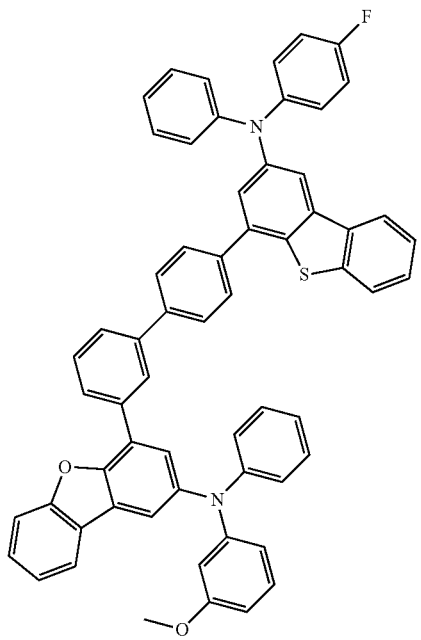
P-63
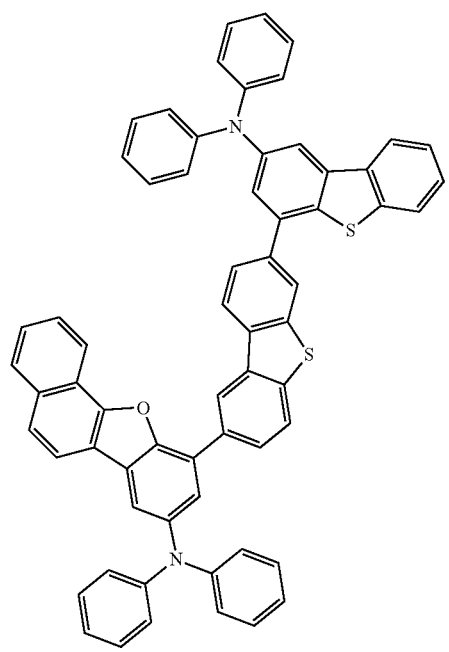
P-64
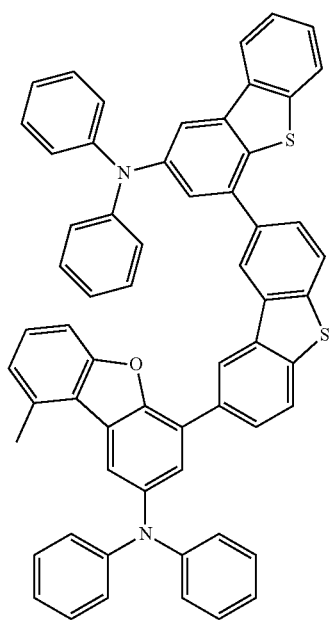

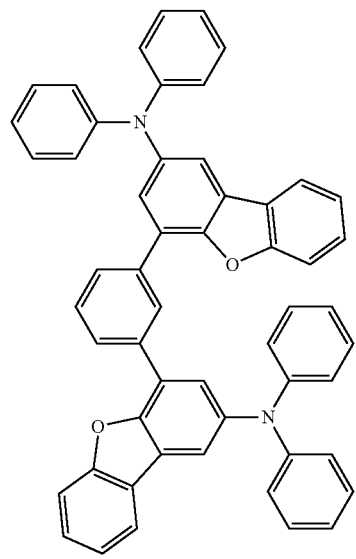
P-65
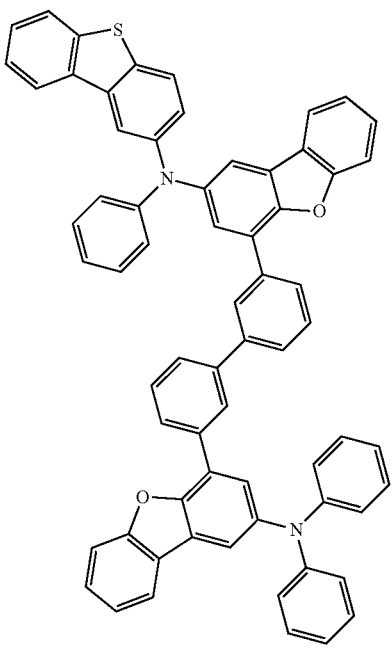
P-66
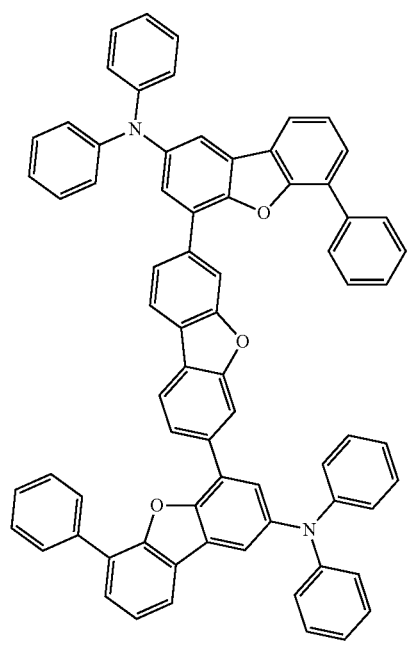
P-67
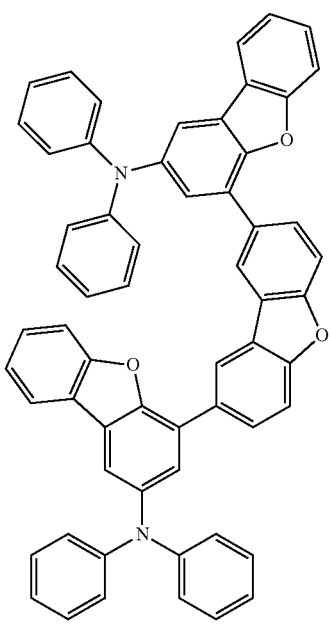
P-68

-continued
P-69
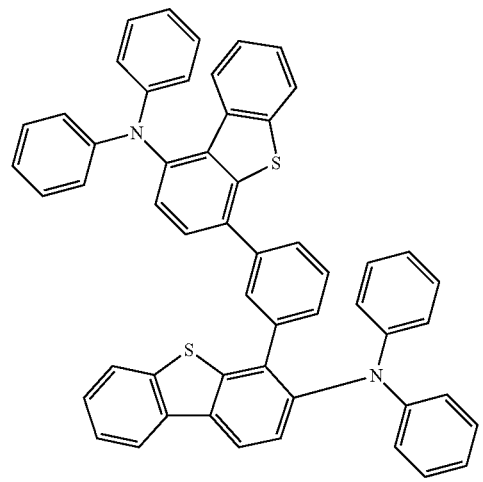
P-70
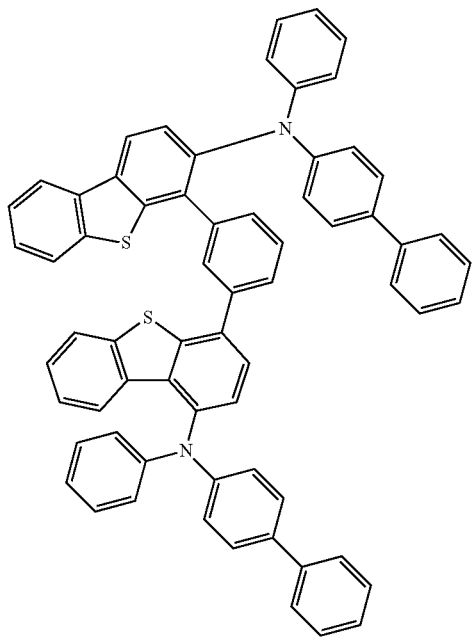
P-71
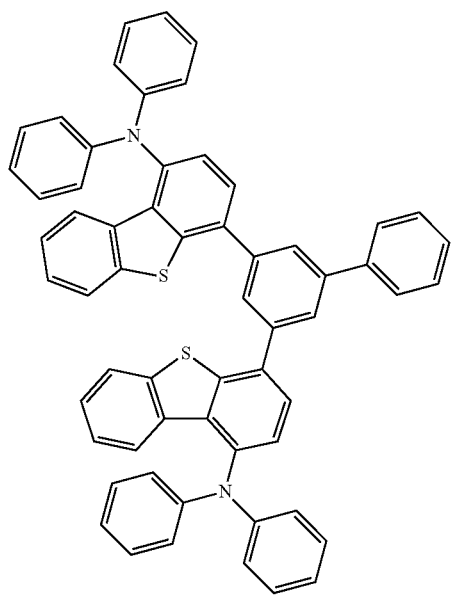
P-72
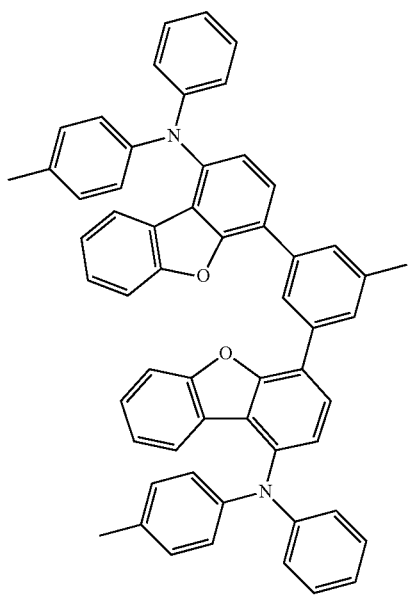

P-73
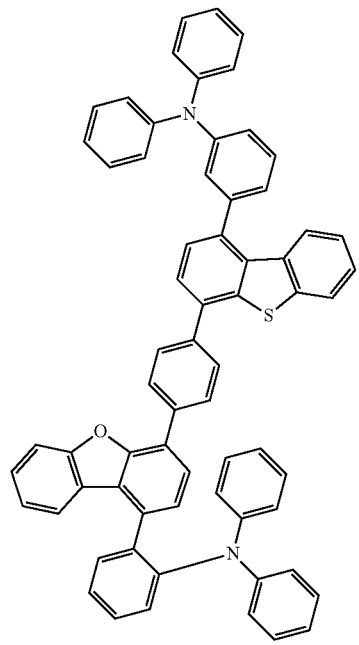
P-74
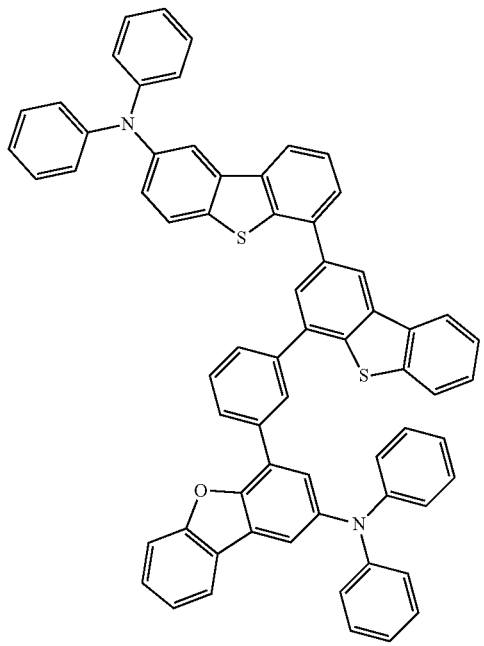
P-75
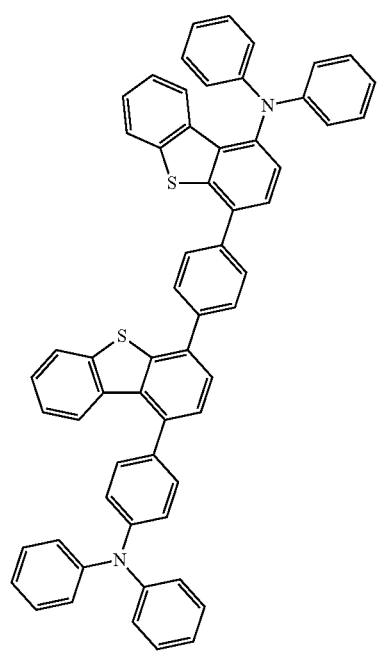
P-76
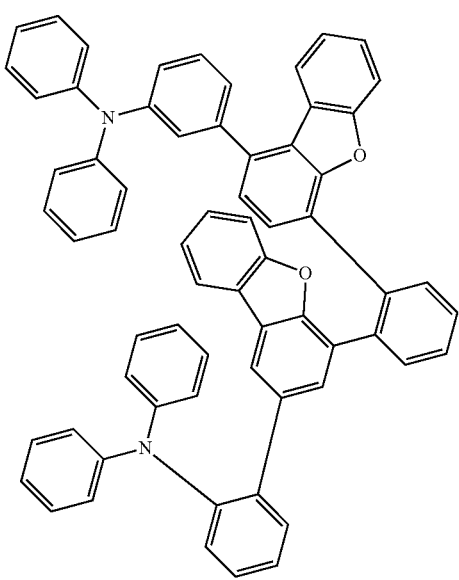

-continued
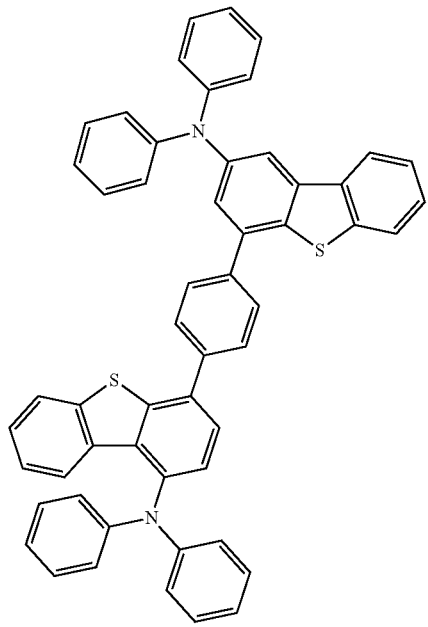
P-78
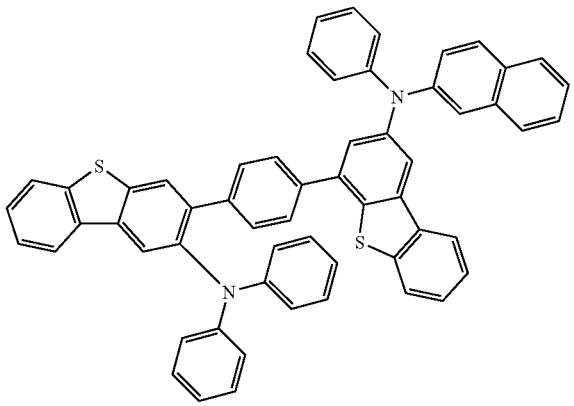
P-79
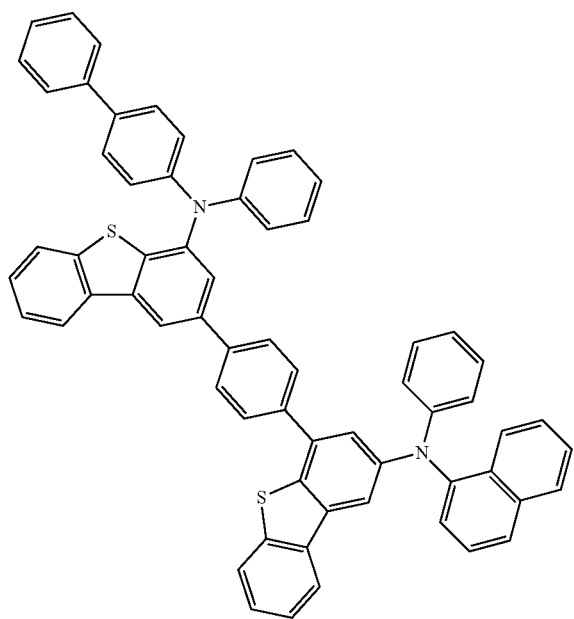
P-80

-continued
P-81
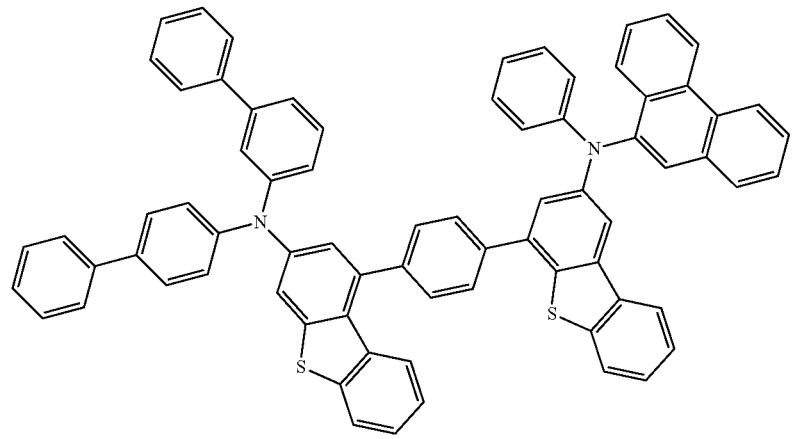
P-82
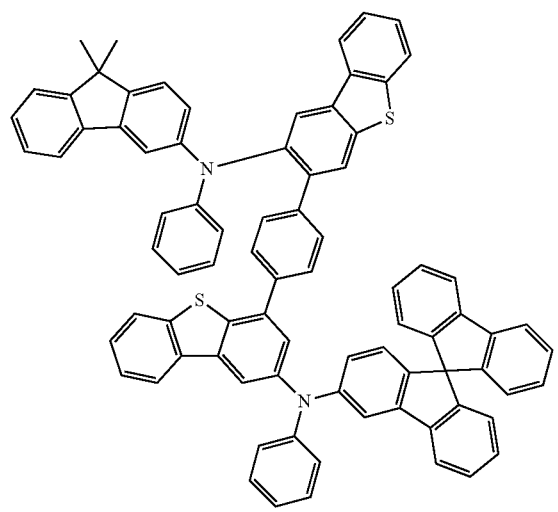
P-83
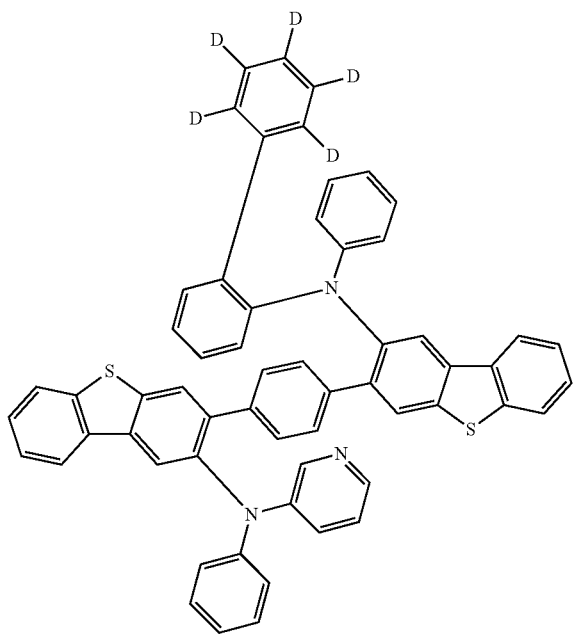
P-84
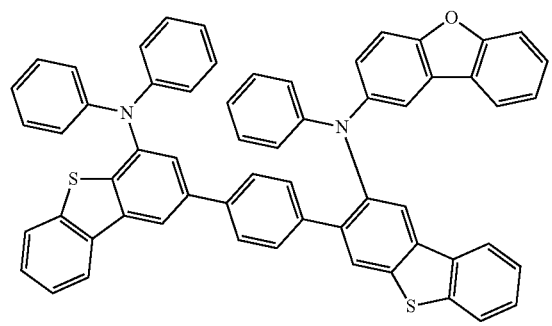
P-85
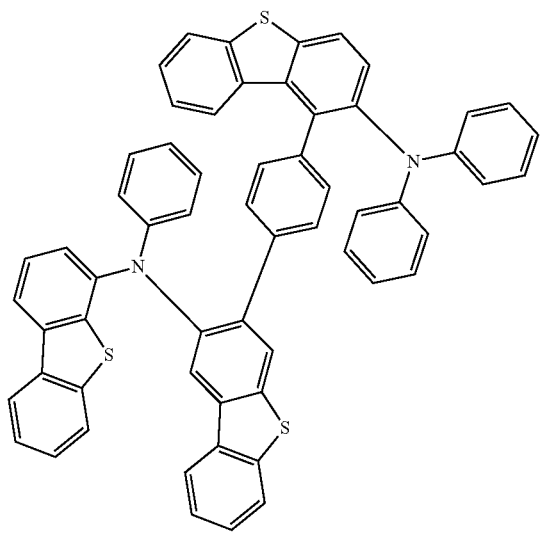

P-86
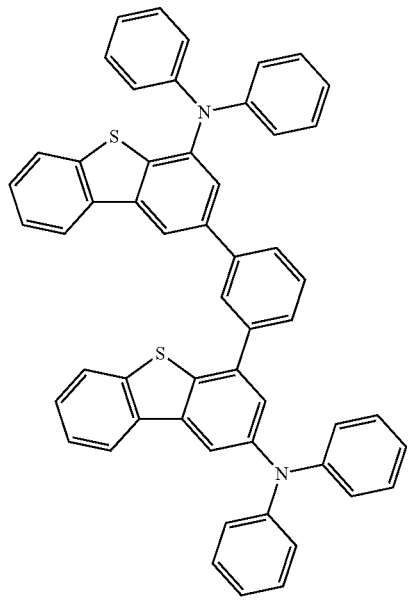
P-87
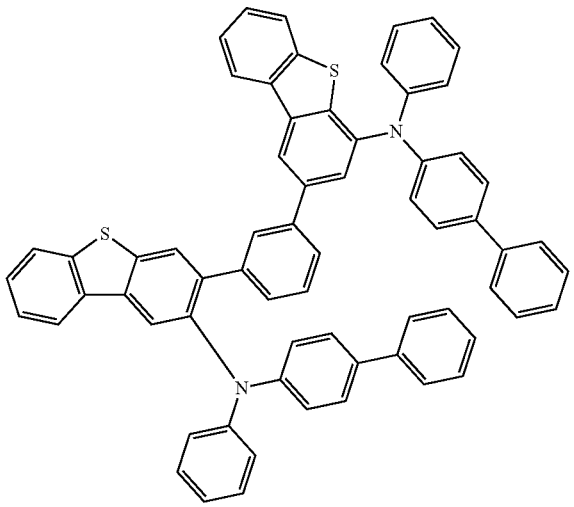
P-88
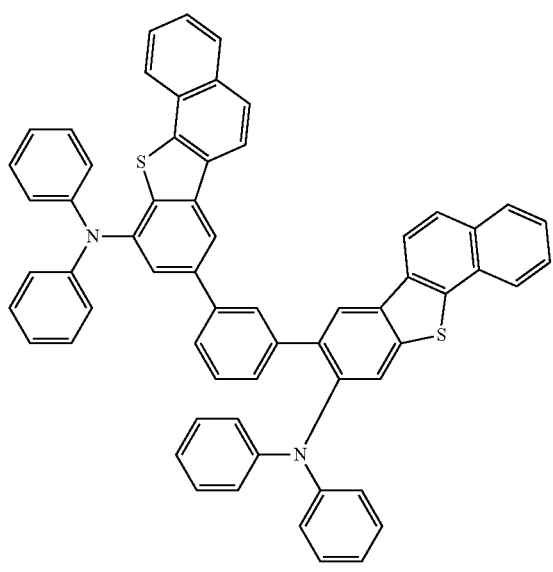
P-89
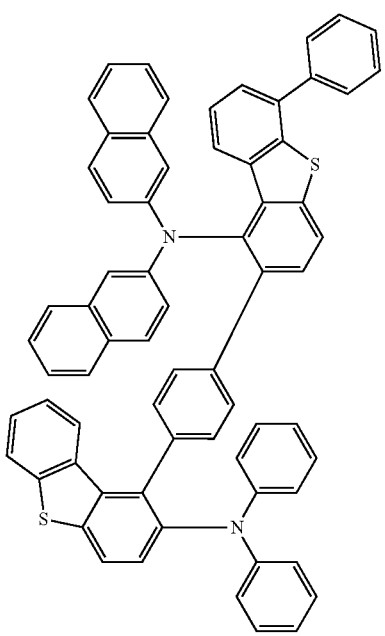

-continued

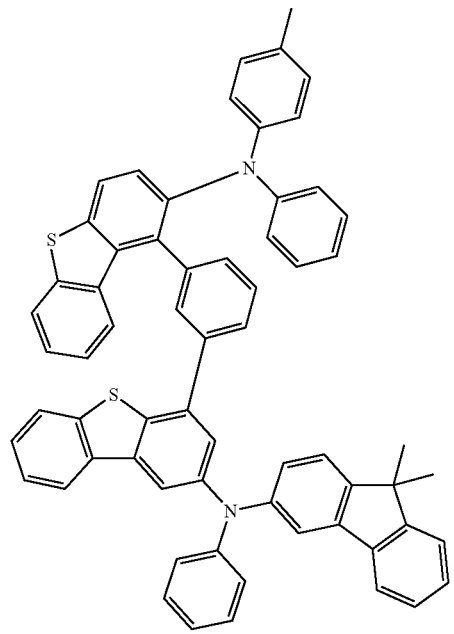

P-90

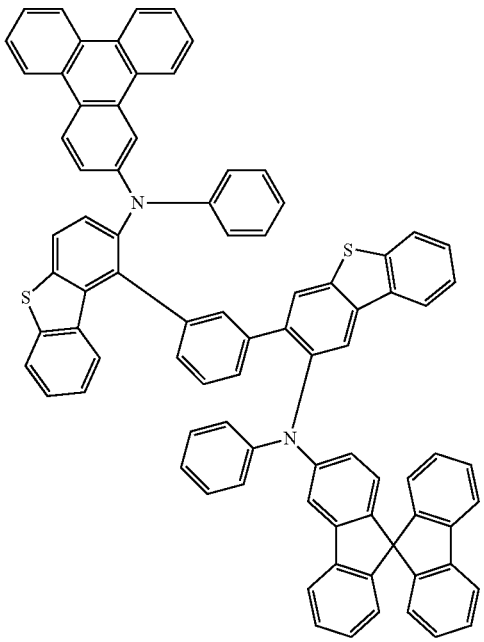

P-91

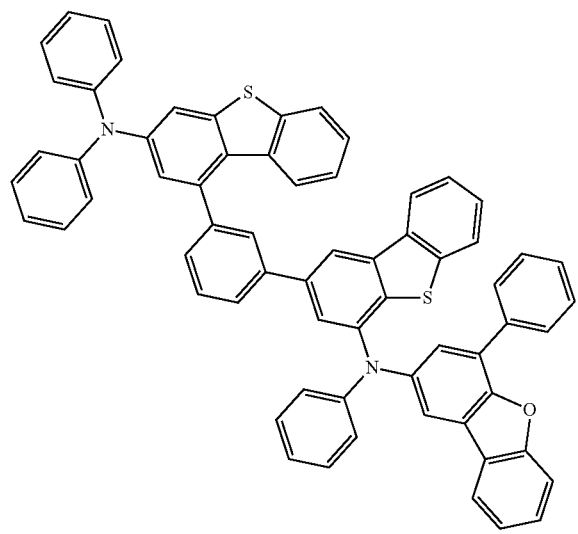

P-92

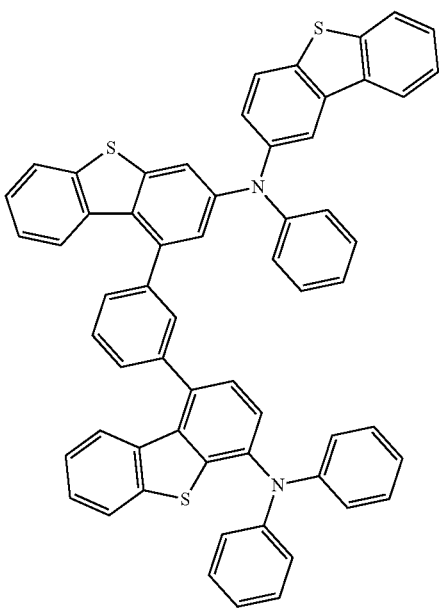

P-93

In another aspect of the present invention, the present invention provides an organic electric element comprising a first electrode, a second electrode, and an organic material layer formed between the first electrode and the second electrode.

The organic material layer comprises at least one layer of a hole injection layer, a hole transport layer, an emission-auxiliary layer, a light emitting layer, an electron transport auxiliary layer, an electron transport layer and an electron injection layer, and at least one layer of the hole injection layer, the hole transport layer, the emission-auxiliary layer, the light emitting layer, the electron transport auxiliary layer, the electron transport layer and the electron injection layer comprises a single compound or a mixture of two or more kinds represented by Formula 1, and preferably, the compound may be used as material of the emission-auxiliary layer.

In another aspect of the present invention, the present invention provides an electronic device comprising a display device and a control unit for driving the display device, wherein the display device comprises the organic electric element.

Hereinafter, synthesis example of the compound represented by Formula 1 and preparation method of an organic electric element according to one embodiment of the present invention will be described in detail by way of examples. However, the present invention is not limited to the following examples.

Synthesis Example

The compounds (final products) represented by Formula 1 according to the present invention can be synthesized by reacting Sub 1 with Sub 2.

<Reaction Scheme 1>

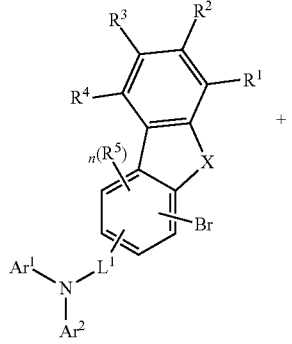

Sub 1

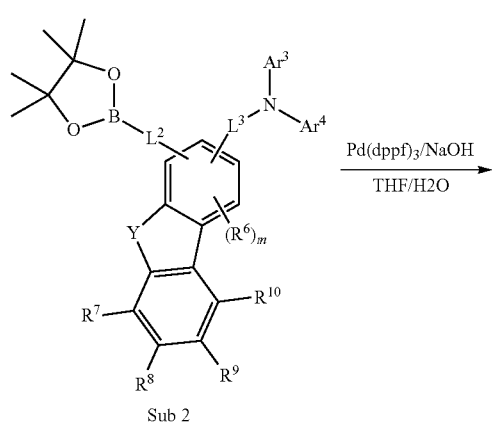

Sub 2

Final Products

I. Synthesis of Sub 1

The compound belonging to Sub 1 of the Reaction Scheme 1 may be synthesized by the reaction route of the following Reaction Scheme 2. In the following Reaction Scheme 2, L corresponds to $L^1$ in the Reaction Scheme 1.

<Reaction Scheme 2>

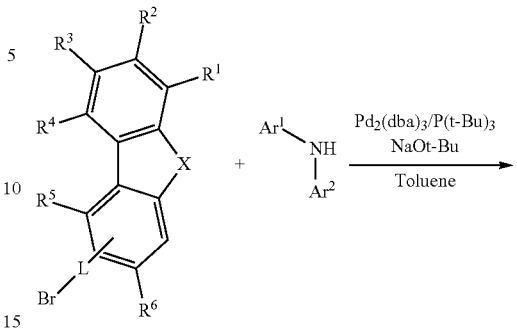

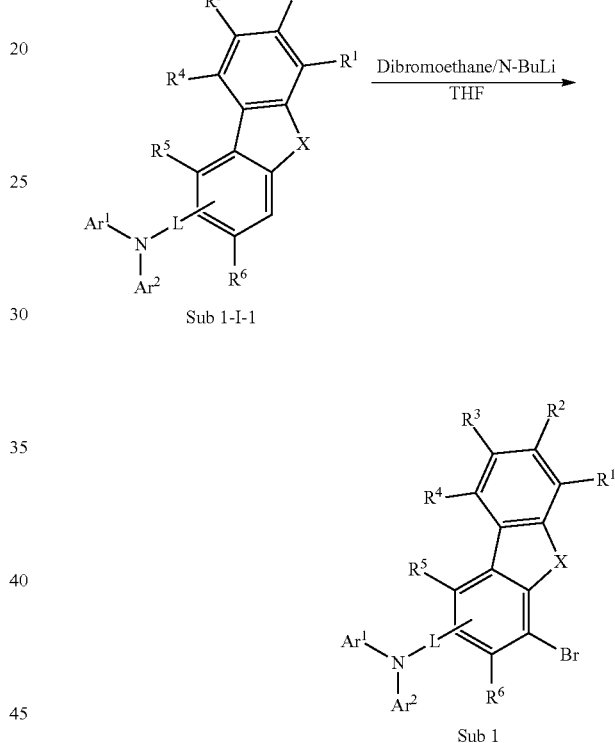

Sub 1

Synthesis examples of specific compounds belonging to Sub 1 are as follows.

1. Synthesis Example of Sub1-1

<Reaction Scheme 3>

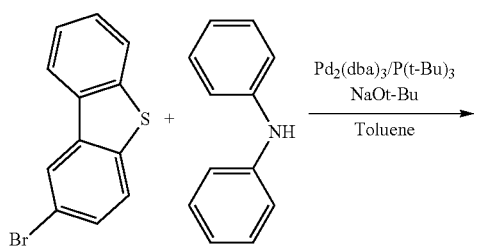

65

-continued

Sub 1-I-1

Sub 1-1

(1) Synthesis of Sub 1-I-1

The starting material 2-bromodibenzo [b, d] thiophene (100 g, 0.38 mol) was placed into a round bottom flask and dissolved with toluene (760 mL). Diphenylamine (64.3 g, 0.38 mol), $Pd_2(dba)_3$ (10.4 g, 0.0114 mmol), 50% $P(t-Bu)_3$ (9.22 ml, 0.02281 mmol) and NaOt-Bu (109 g, 1.14 mmol) were added the solution and stirred at 80° C. When the reaction was completed, the reaction product was extracted with $CH_2Cl_2$ and water. Then, the organic layer was dried with $MgSO_4$ and concentrated. Then, the concentrate was applied to silicagel column and recrystallized to obtain 131 g (yield: 98%) of the product Sub 1-I-1.

(2) Synthesis of Sub 1-1

Sub 1-I-1 (100 g, 0.284 mol) was added to THF (570 ml) and the solution was stirred at −78° C. Then, 2.5M n-BuLi (125 mL) was slowly added to the solution and the mixture was stirred for 1 hour. 1,2-dibromoethane (58.5 g, 0.313 mol) was slowly added thereto and the mixture was stirred at room temperature for 8 hours. When the reaction was completed, 100 g (yield: 82%) of the product Sub 1-1 was obtained by using the same manner as in the synthesis method of Sub 1-I-1.

66

2. Synthesis of Sub 1-12

<Reaction Scheme 4>

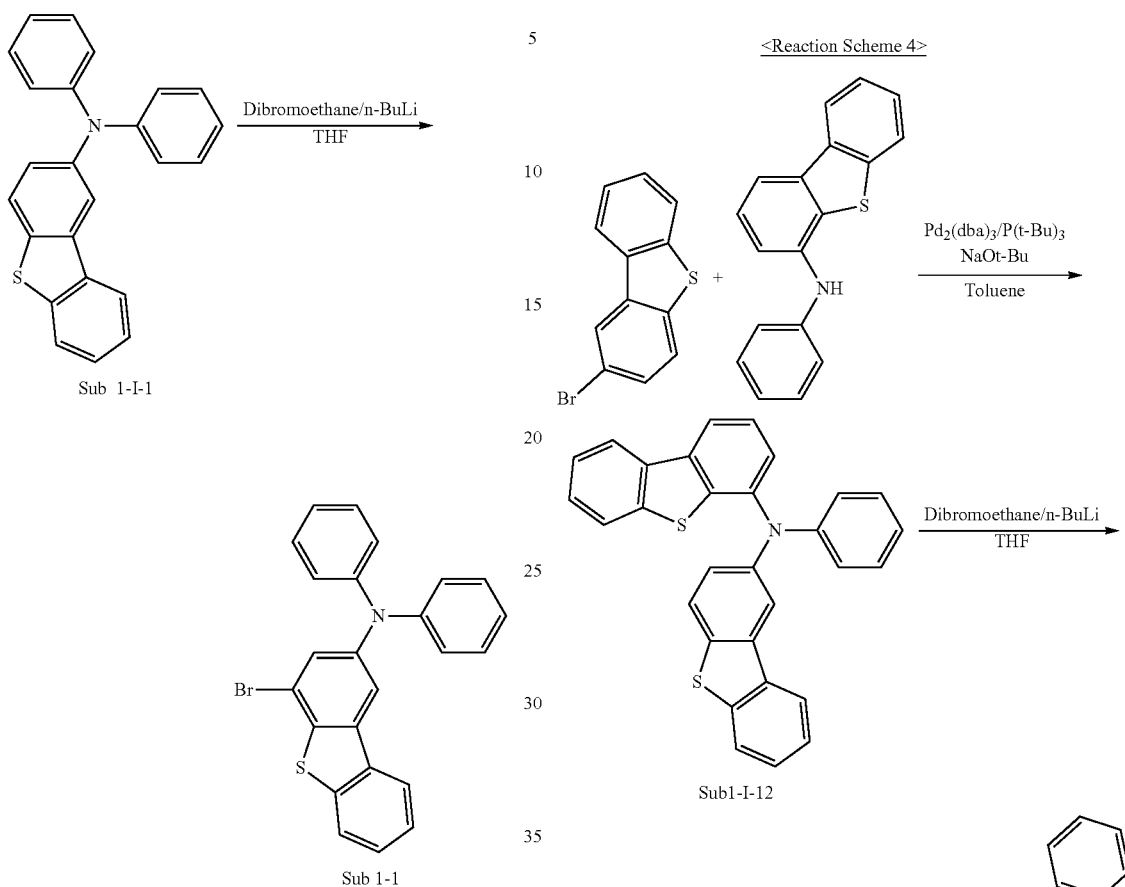

Sub1-I-12

Sub1-12

(1) Synthesis of Sub 1-I-12

The starting material 2-bromodibenzo[b,d]thiophene (100 g, 0.38 mol) was placed into a round bottom flask and dissolved with toluene (760 mL). N-phenyldibenzo[b,d]thiophen-4-amine (105 g, 0.38 mol), $Pd_2(dba)_3$ (10.4 g, 0.0114 mmol), 50% $P(t-Bu)_3$ (9.22 ml, 0.02281 mmol) and NaOt-Bu (109 g, 1.14 mmol) were added the solution and stirred at 80° C. When the reaction was completed, 140 g (yield: 80.5%) of the product Sub 1-I-12 was obtained by using the same manner as in the synthesis method of Sub 1-I-1.

(2) Synthesis of Sub 1-12

Sub 1-I-12 (140 g, 0.306 mol) was added to THF (611 ml) and the solution was stirred at −78° C. Then, 2.5M n-BuLi (134 mL) was slowly added to the solution and the mixture was stirred for 1 hour. 1,2-dibromoethane (63 g, 0.336 mol) was slowly added thereto and the mixture was stirred at room temperature for 8 hours. When the reaction was completed, 140 g (yield: 85%) of the product Sub 1-12 was obtained by using the same manner as in the synthesis method of Sub 1-I-1.

3. Synthesis of Sub 1-20

<Reaction Scheme 5>

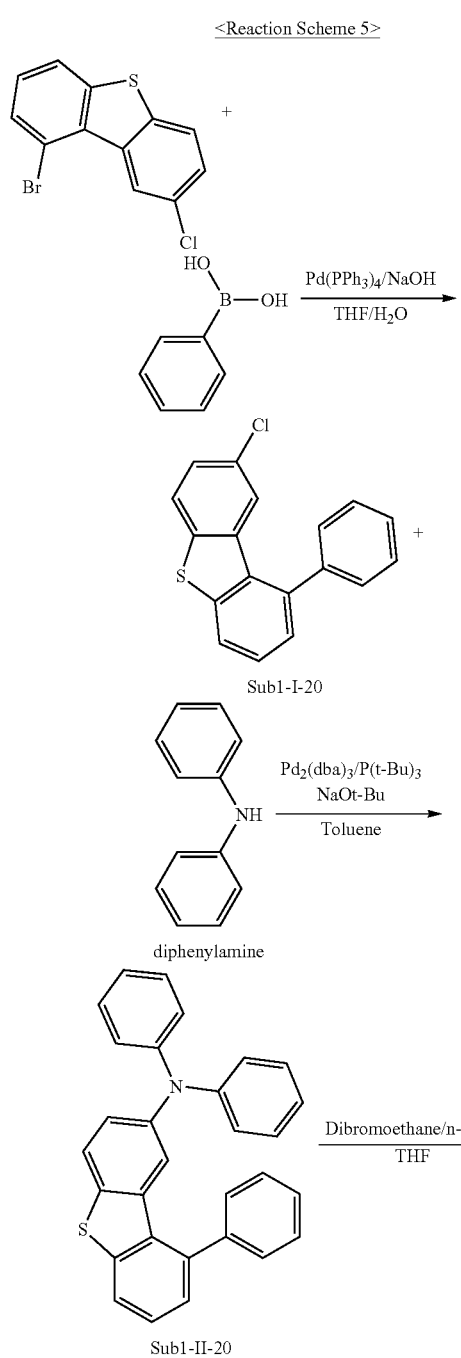

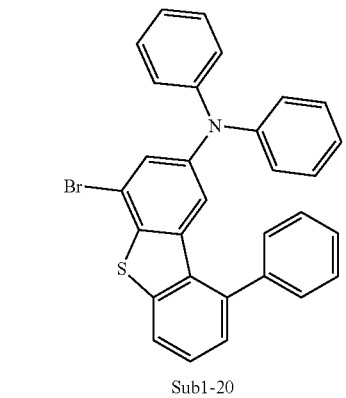

(1) Synthesis of Sub 1-I-20

The starting material 1-bromo-8-chlorodibenzo[b,d]thiophene (100 g, 0.336 mol) was placed into a round bottom flask and dissolved with THF (672 mL) and $H_2O$ (224 mL). Phenylboronic acid (41 g, 0.336 mol), $Pd(PPh_3)_4$ (11.6 g, 0.01 mol) and NaOH (40 g, 0.1 mol) were added the solution and stirred at 80° C. When the reaction was completed, the reaction product was extracted with $CH_2Cl_2$ and water. Then, the organic layer was dried with $MgSO_4$ and concentrated. Then, the concentrate was applied to silicagel column and recrystallized to obtain 89 g (yield: 90%) of the product Sub 1-I-20.

(2) Synthesis of Sub 1-II-20

Sub 1-I-20 (89 g, 0.30 mol), diphenylamine (51.1 g, 0.30 mol), $Pd_2(dba)_3$ (8.2 g, 0.009 mol), 50% $P(t-Bu)_3$ (7.32 ml, 0.018 mol) and NaOt-Bu (87 g, 0.91 mmol) were added to toluene (600 ml) and the solution was stirred at 130° C. When the reaction was completed, 100 g (yield: 77.5%) of the product Sub 1-II-20 was obtained by using the same manner as in the synthesis method of Sub 1-I-20.

(3) Synthesis of Sub 1-20

Sub 1-II-20 (100 g, 0.233 mol) was added to THF (467 mL) and the solution was stirred at −78° C. Then, 2.5M n-BuLi (102 mL) was slowly added to the solution and the mixture was stirred for 1 hour. 1,2-dibromoethane (48 g, 0.257 mol) was slowly added thereto and the mixture was stirred at room temperature for 8 hours. When the reaction was completed, 100 g (yield: 85%) of the product Sub 1-20 was obtained by using the same manner as in the synthesis method of Sub 1-I-1.

4. Synthesis of Sub 1-26

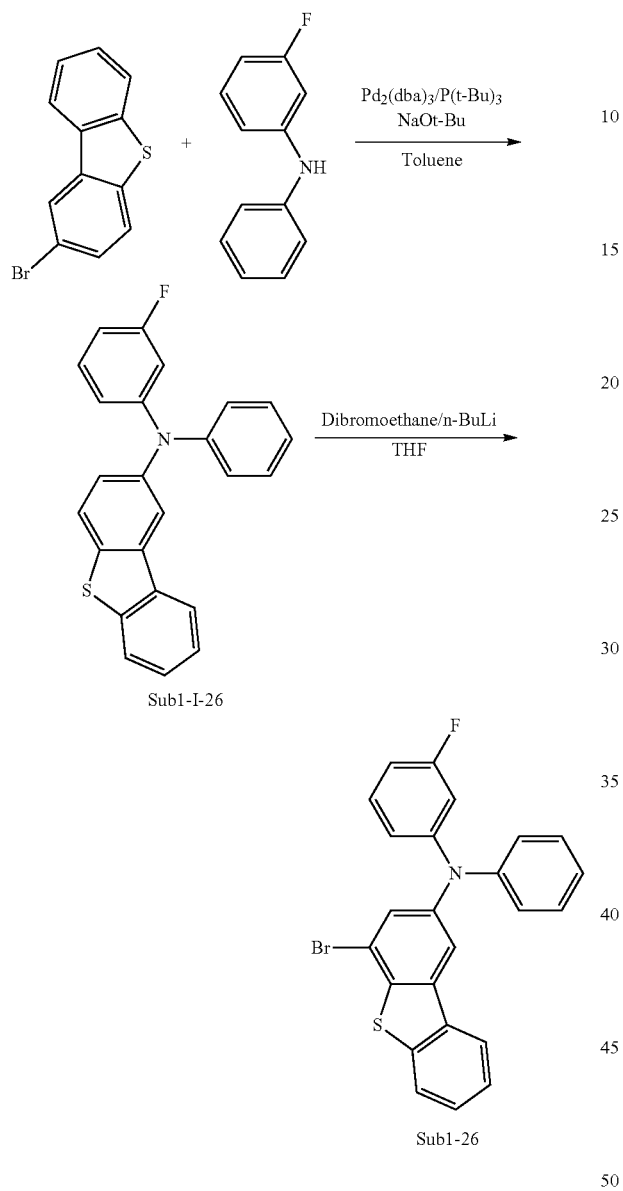

Sub1-I-26

Sub1-26

(1) Synthesis of Sub 1-I-26

The starting material 2-bromodibenzo[b,d]thiophene (100 g, 0.38 mol), 3-fluoro-N-phenylaniline (71.1 g, 0.38 mol), $Pd_2(dba)_3$ (10.4 g, 0.01 mol), 50% P(t-Bu)$_3$ (9.2 ml, 0.022 mol) and NaOt-Bu (109 g, 1.14 mmol) were added to toluene (760 ml) and the solution was stirred at 75° C. When the reaction was completed, 100 g (yield: 71.2%) of the product Sub 1-I-26 was obtained by using the same manner as in the synthesis method of Sub 1-I-1.

(2) Synthesis of Sub 1-26

Sub 1-I-26 (100 g, 0.27 mol) was added to THF (541 mL) and the solution was stirred at −78° C. While maintaining the temperature, 2.5M n-BuLi (119 mL) was slowly added to the solution and the mixture was stirred for 1 hour. 1,2-dibromoethane (55.7 g, 0.297 mol) was slowly added thereto and the mixture was stirred at room temperature for 8 hours. When the reaction was completed, 102 g (yield: 84%) of the product Sub 1-26 was obtained by using the same manner as in the synthesis method of Sub 1-I-1.

5. Synthesis of Sub 1-30

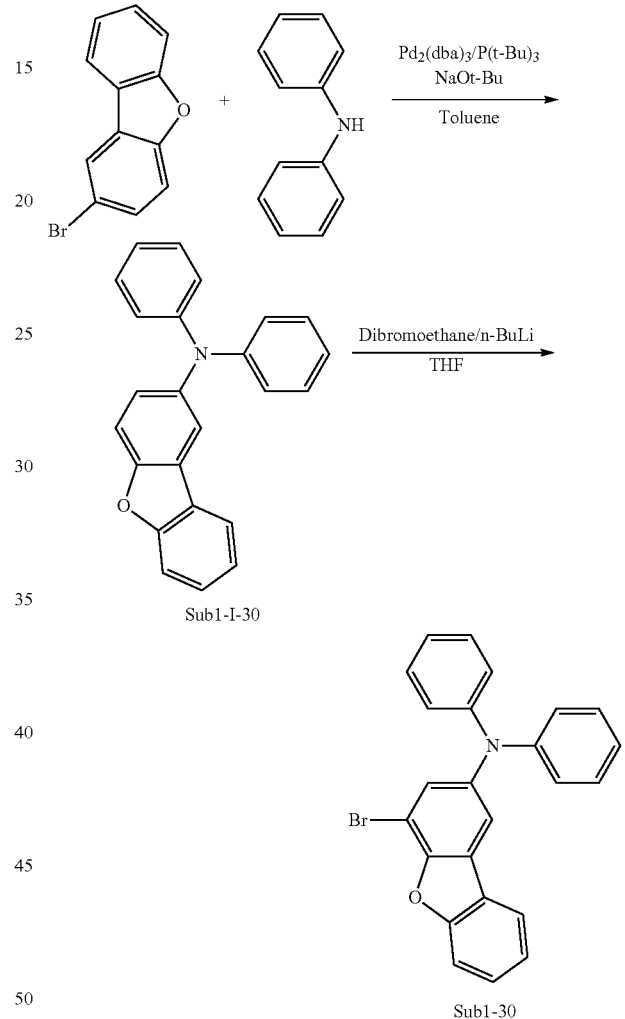

Sub1-I-30

Sub1-30

(1) Synthesis of Sub 1-I-30

The starting material 2-bromodibenzo[b,d]furan (100 g, 0.234 mol), diphenylamine (39.6 g, 0.234 mol), $Pd_2(dba)_3$ (6.4 g, 0.007 mol), 50% P(t-Bu)$_3$ (5.6 ml, 0.014 mol) and NaOt-Bu (67.5 g, 0.7 mmol) were added to toluene (468 ml) and the solution was stirred at 75° C. When the reaction was completed, 64 g (yield: 81.5%) of the product Sub 1-I-30 was obtained by using the same manner as in the synthesis method of Sub 1-I-1.

(2) Synthesis of Sub 1-30

Sub 1-I-26 (50 g, 0.14 mol) was added to THF (300 mL) and the solution was stirred at −78° C. While maintaining the temperature, 2.5M n-BuLi (65.59 mL) was slowly added to the solution and the mixture was stirred for 1 hour. 1,2-dibromoethane (30.6 g, 0.163 mol) was slowly added thereto and the mixture was stirred at room temperature for 8 hours. When the reaction was completed, 55 g (yield: 89%) of the product Sub 1-30 was obtained by using the same manner as in the synthesis method of Sub 1-I-1.

The compounds belonging to Sub 1 may be, but not limited to, the following compounds, and Table 1 shows the FD-MS values of the compounds belonging to Sub 1.

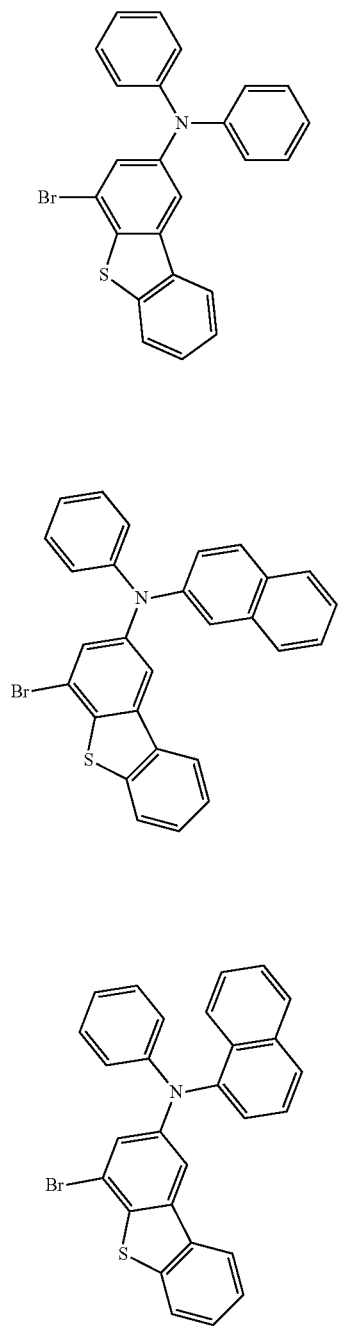

Sub1-1

Sub1-2

Sub1-3

-continued

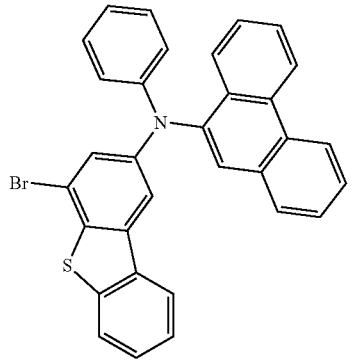

Sub1-4

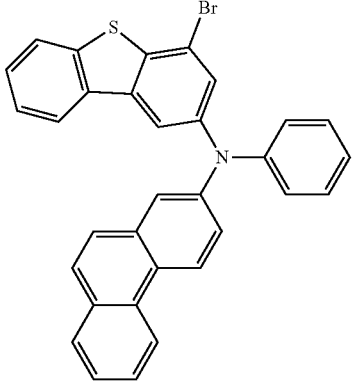

Sub1-5

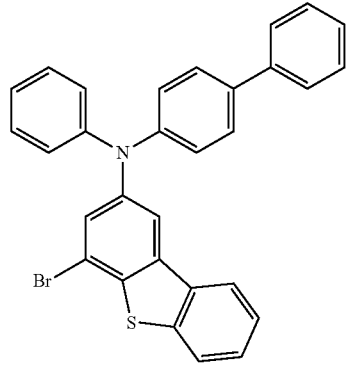

Sub1-6

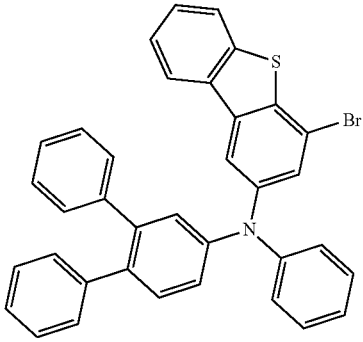

Sub1-7

Sub1-8
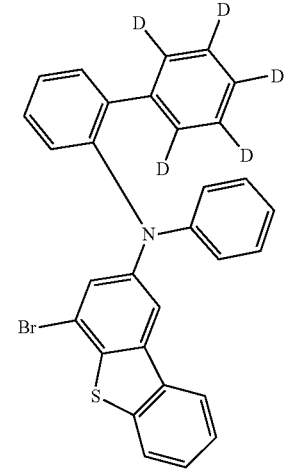
Sub1-9
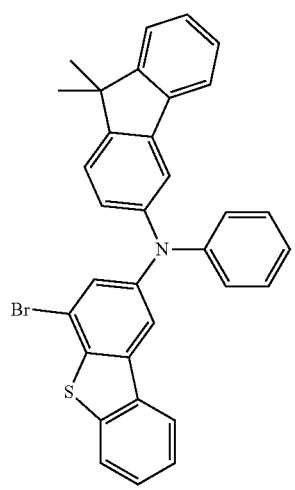
Sub1-10
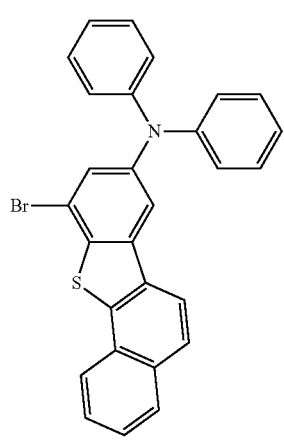
Sub1-11
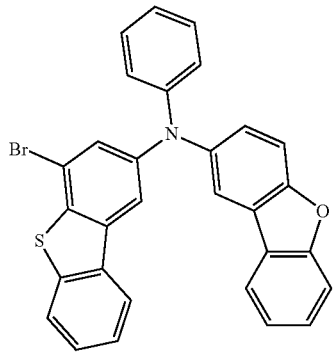
Sub1-12
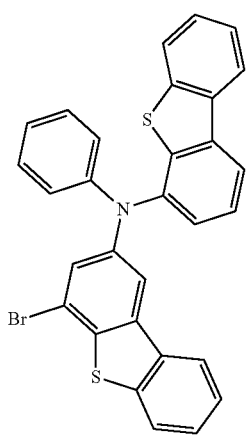
Sub1-13
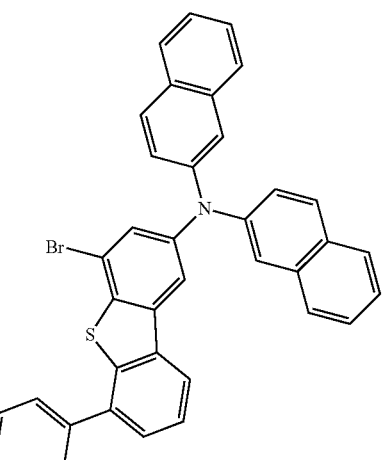
Sub1-14
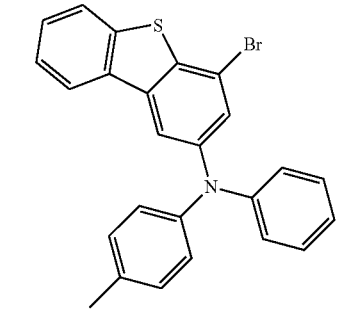

Sub1-15
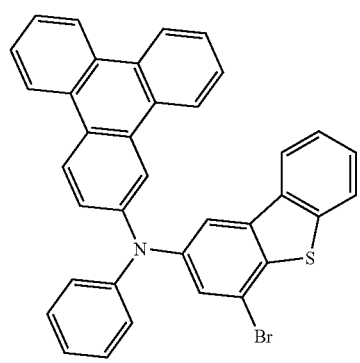
Sub1-16
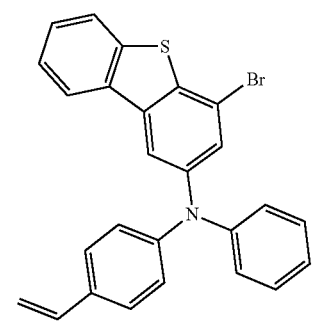
Sub1-17
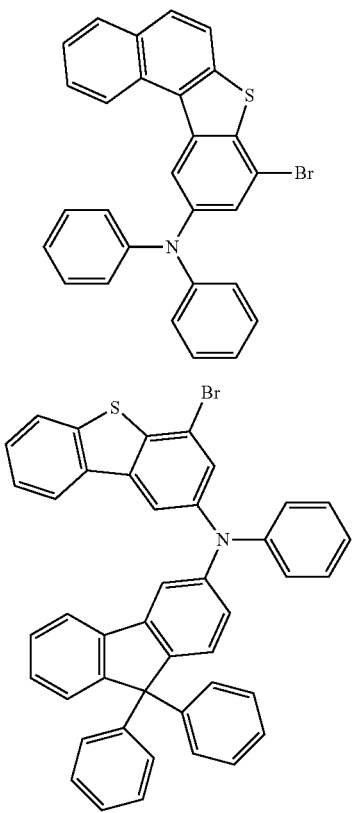
Sub1-18
Sub1-19
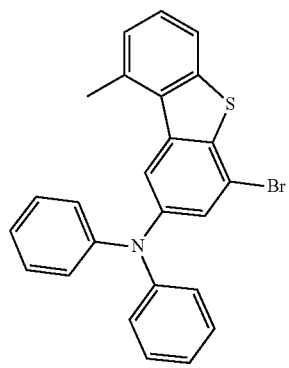
Sub1-20
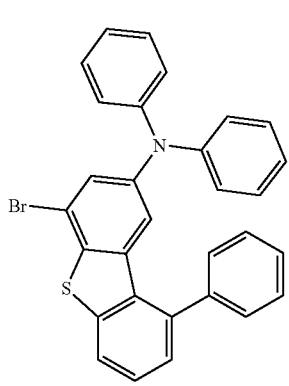
Sub1-21
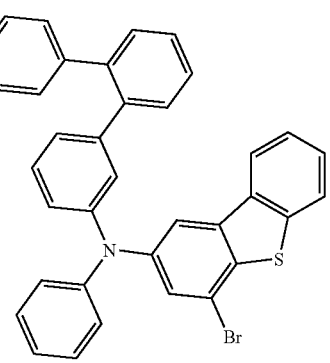
Sub1-22
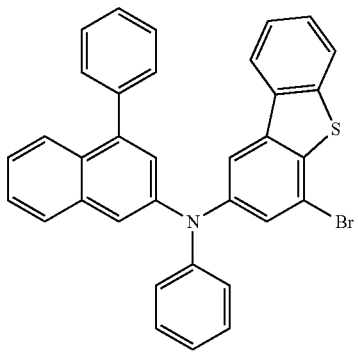

Sub1-23
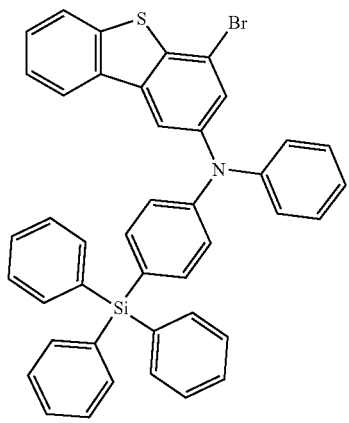
Sub1-24
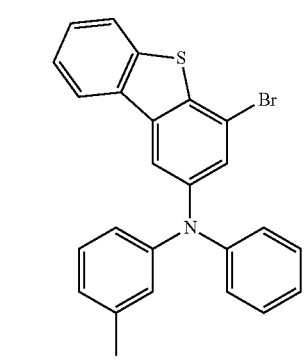
Sub1-25
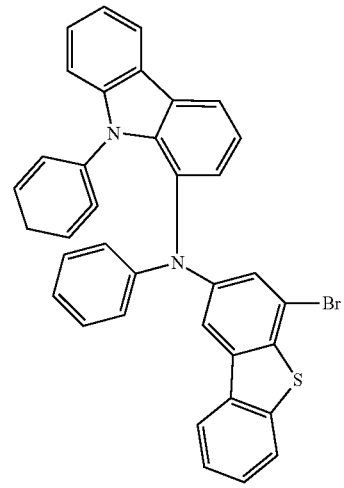
Sub1-26
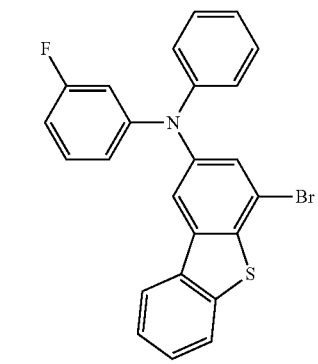
Sub1-27
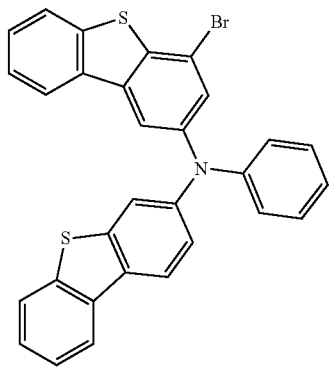
Sub1-28
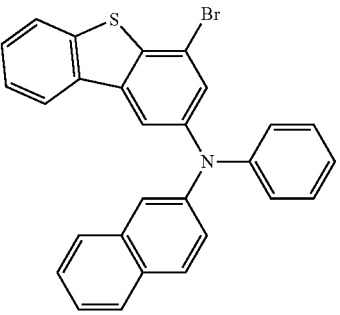
Sub1-29
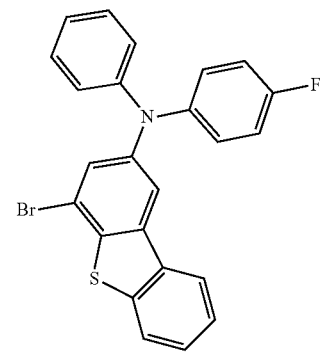
Sub1-30
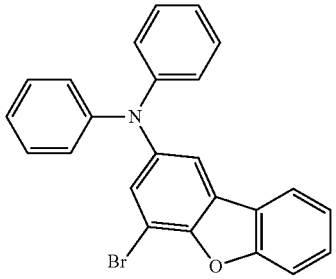

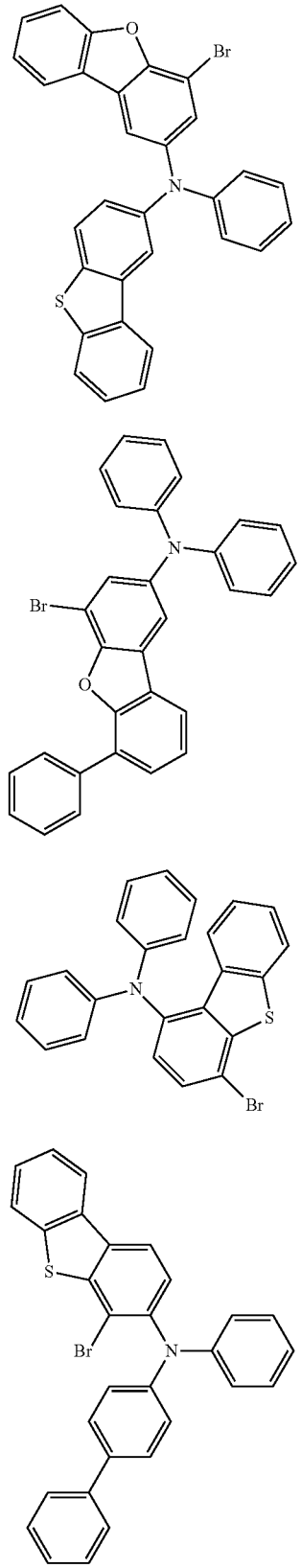
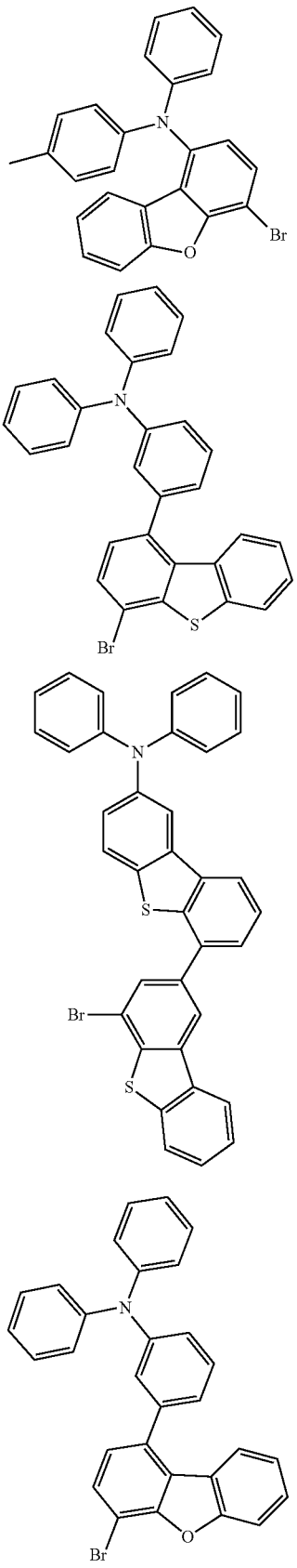

TABLE 1

| Compound | FD-MS | Compound | FD-MS |
|---|---|---|---|
| Sub 1-1 | m/z = 429.02 ($C_{24}H_{16}BrNS$ = 430.36) | Sub 1-2 | m/z = 479.03 ($C_{28}H_{18}BrNS$ = 480.42) |
| Sub 1-3 | m/z = 479.03 ($C_{28}H_{18}BrNS$ = 480.42) | Sub 1-4 | m/z = 529.05 ($C_{32}H_{20}BrNS$ = 530.48) |
| Sub 1-5 | m/z = 529.05 ($C_{32}H_{20}BrNS$ = 530.48) | Sub 1-6 | m/z = 505.05 ($C_{30}H_{20}BrNS$ = 506.46) |
| Sub 1-7 | m/z = 581.08 ($C_{36}H_{24}BrNS$ = 582.56) | Sub 1-8 | m/z = 510.08 ($C_{30}H_{15}D_5BrNS$ = 511.49) |
| Sub 1-9 | m/z = 545.08 ($C_{33}H_{24}BrNS$ = 546.53) | Sub 1-10 | m/z = 479.03 ($C_{28}H_{18}BrNS$ = 480.42) |
| Sub 1-11 | m/z = 519.03 ($C_{30}H_{18}BrNOS$ = 520.44) | Sub 1-12 | m/z = 535.01 ($C_{30}H_{18}BrNS_2$ = 536.51) |
| Sub 1-13 | m/z = 605.08 ($C_{38}H_{24}BrNS$ = 606.58) | Sub 1-14 | m/z = 443.03 ($C_{25}H_{18}BrNS$ = 444.39) |
| Sub 1-15 | m/z = 579.07 ($C_{36}H_{22}BrNS$ = 580.54) | Sub 1-16 | m/z = 455.03 ($C_{26}H_{18}BrNS$ = 456.40) |
| Sub 1-17 | m/z = 479.03 ($C_{28}H_{18}BrNS$ = 480.42) | Sub 1-18 | m/z = 669.11 ($C_{43}H_{28}BrNS$ = 670.67) |
| Sub 1-19 | m/z = 443.03 ($C_{25}H_{18}BrNS$ = 444.39) | Sub 1-20 | m/z = 505.05 ($C_{30}H_{20}BrNS$ = 506.46) |
| Sub 1-21 | m/z = 581.08 ($C_{36}H_{24}BrNS$ = 582.56) | Sub 1-22 | m/z = 555.07 ($C_{34}H_{22}BrNS$ = 556.52) |
| Sub 1-23 | m/z = 687.11 ($C_{42}H_{30}BrNSSi$ = 688.76) | Sub 1-24 | m/z = 443.03 ($C_{25}H_{18}BrNS$ = 444.39) |
| Sub 1-25 | m/z = 594.08 ($C_{36}H_{23}BrN_2S$ = 595.56) | Sub 1-26 | m/z = 447.01 ($C_{24}H_{15}BrFNS$ = 448.35) |
| Sub 1-27 | m/z = 535.01 ($C_{30}H_{18}BrNS_2$ = 536.51) | Sub 1-28 | m/z = 479.03 ($C_{28}H_{18}BrNS$ = 480.42) |
| Sub 1-29 | m/z = 447.01 ($C_{24}H_{15}BrFNS$ = 448.35) | Sub 1-30 | m/z = 413.04 ($C_{24}H_{16}BrNO$ = 414.30) |
| Sub 1-31 | m/z = 519.03 ($C_{30}H_{18}BrNOS$ = 520.44) | Sub 1-32 | m/z = 489.07 ($C_{30}H_{20}BrNO$ = 490.40) |
| Sub 1-33 | m/z = 429.02 ($C_{24}H_{16}BrNS$ = 430.36) | Sub 1-34 | m/z = 505.05 ($C_{30}H_{20}BrNS$ = 506.46) |
| Sub 1-35 | m/z = 427.06 ($C_{25}H_{18}BrNO$ = 428.33) | Sub 1-36 | m/z = 505.05 ($C_{30}H_{20}BrNS$ = 506.46) |
| Sub 1-37 | m/z = 611.04 ($C_{36}H_{22}BrNS2$ = 612.60) | Sub 1-36 | m/z = 489.07 ($C_{30}H_{20}BrNO$ = 490.40) |

II. Synthesis of Sub 2

Sub 2 of the Reaction Scheme 1 can be synthesized by the reaction route of the following Reaction Scheme 8, but there is no limitation thereto.

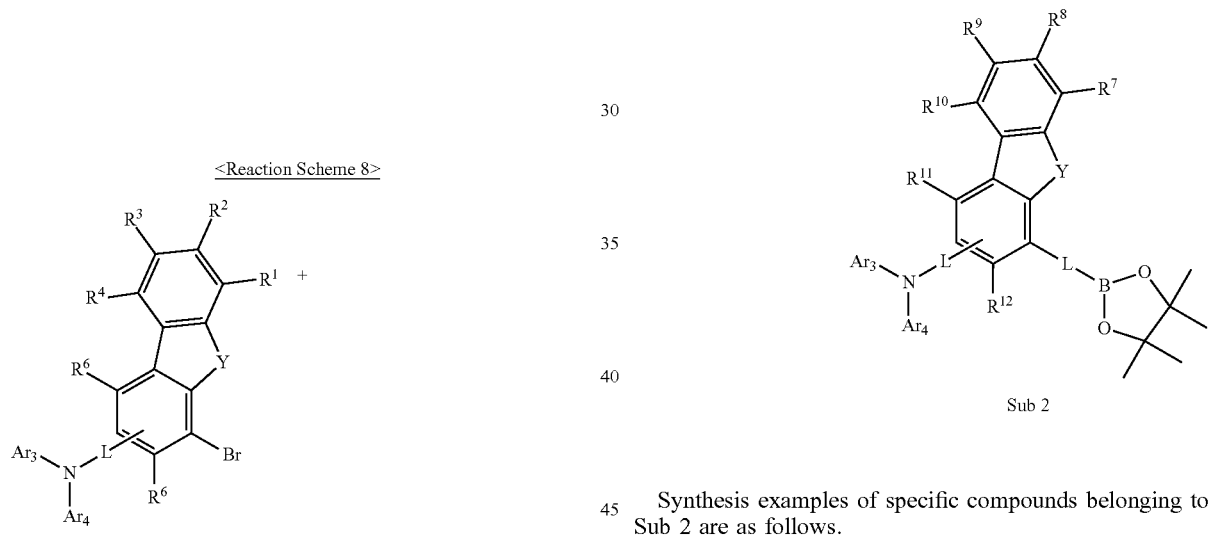

Synthesis examples of specific compounds belonging to Sub 2 are as follows.

1. Synthesis Example of Sub 2-1

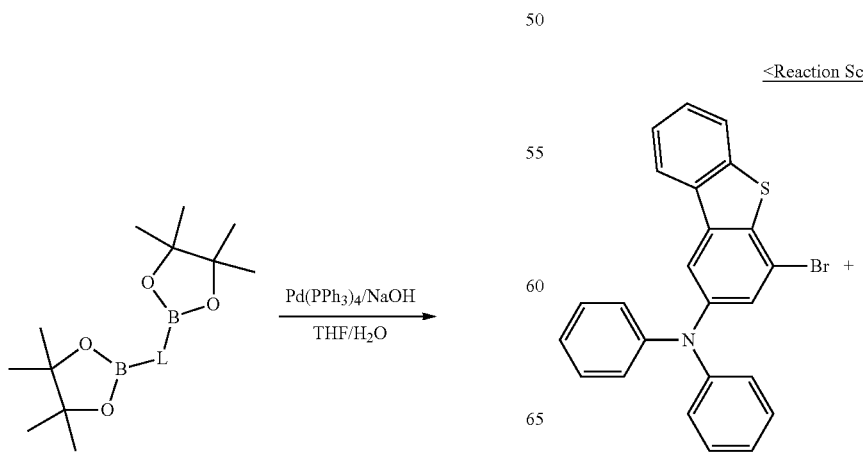

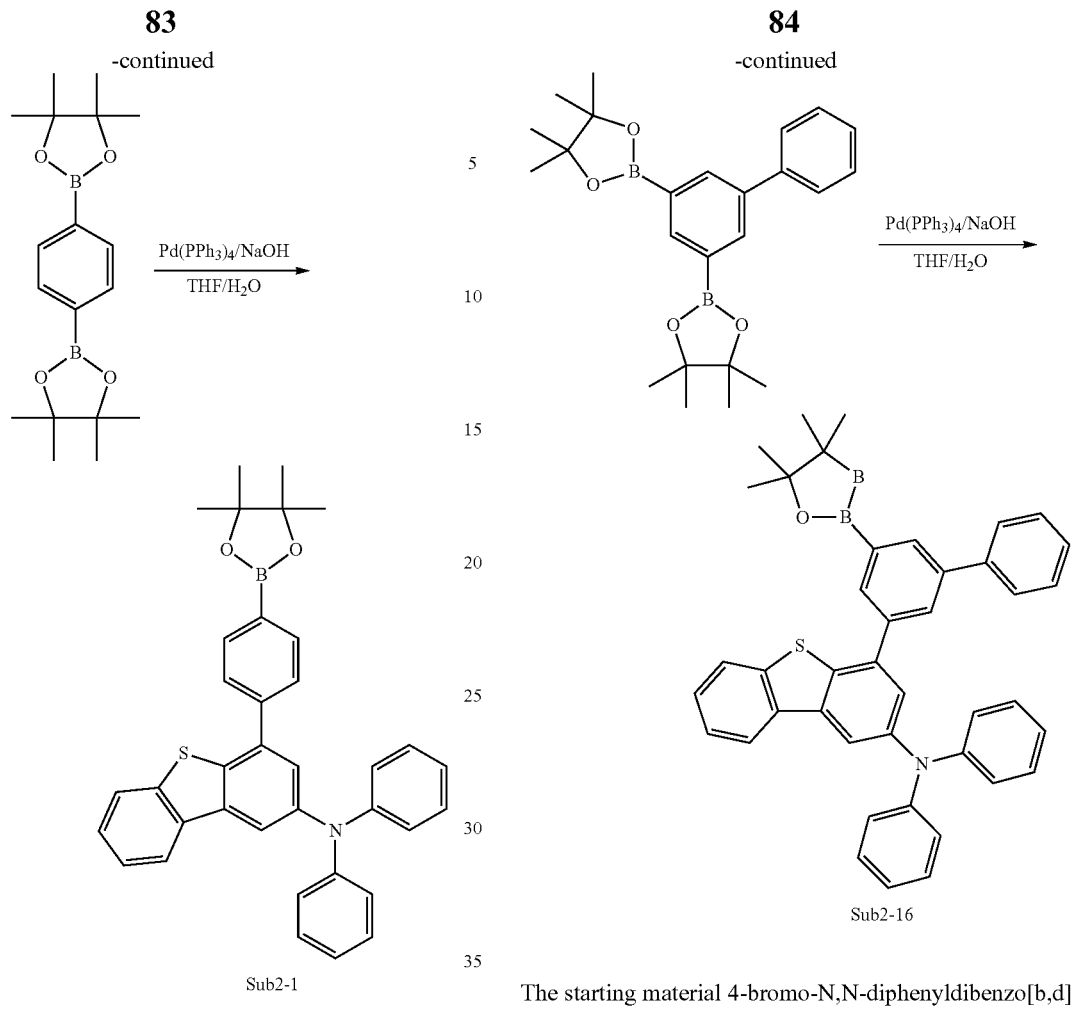

The starting material 4-bromo-N,N-diphenyldibenzo[b,d]thiophen-2-amine (50 g, 0.12 mol) and 1,4-bis(4,4,5,5-tetramethyl-1,3,2-dioxaborolan-2-yl)benzene (38.4 g, 0.12 mol) were placed into a round bottom flask and dissolved with THF (232 mL) and H₂O (80 mL). Pd(PPh₃)₄ (4 g, 0.003 mol) and NaOH (14 g, 0.348 mol) were added the solution, and the reaction was carried out at 75° C. When the reaction was completed, 55 g (yield: 85.5%) of the product Sub 2-1 was obtained by using the same manner as in the synthesis method of Sub 1-1.

2. Synthesis Example of Sub 2-16

<Reaction Scheme 10>

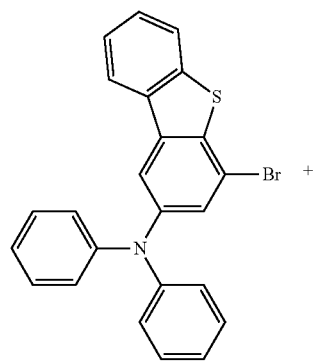

The starting material 4-bromo-N,N-diphenyldibenzo[b,d]thiophen-2-amine (50 g, 0.12 mol) and 3,5-bis(4,4,5,5-tetramethyl-1,3,2-dioxaborolan-2-yl)-1,1'-biphenyl (47 g, 0.12 mol) were placed into a round bottom flask and dissolved with THF (232 mL) and H₂O (80 mL). Pd(PPh₃)₄ (4 g, 0.003 mol) and NaOH (14 g, 0.348 mol) were added the solution, and the reaction was carried out at 75° C. When the reaction was completed, 60 g (yield: 82%) of the product Sub 2-16 was obtained by using the same manner as in the synthesis method of Sub 1-1.

3. Synthesis Example of Sub 2-38

<Reaction Scheme 11>

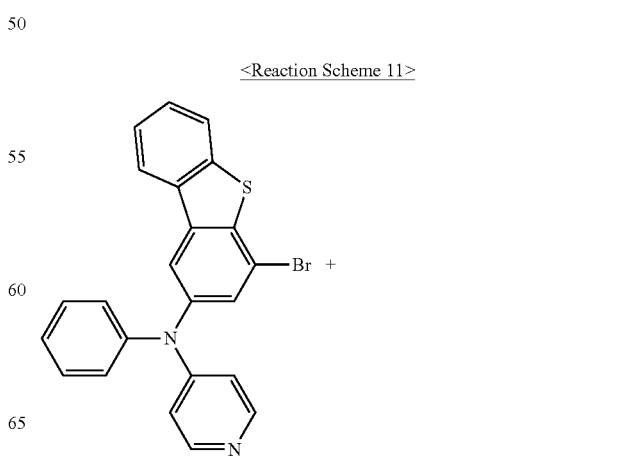

4. Synthesis Example of Sub 2-50

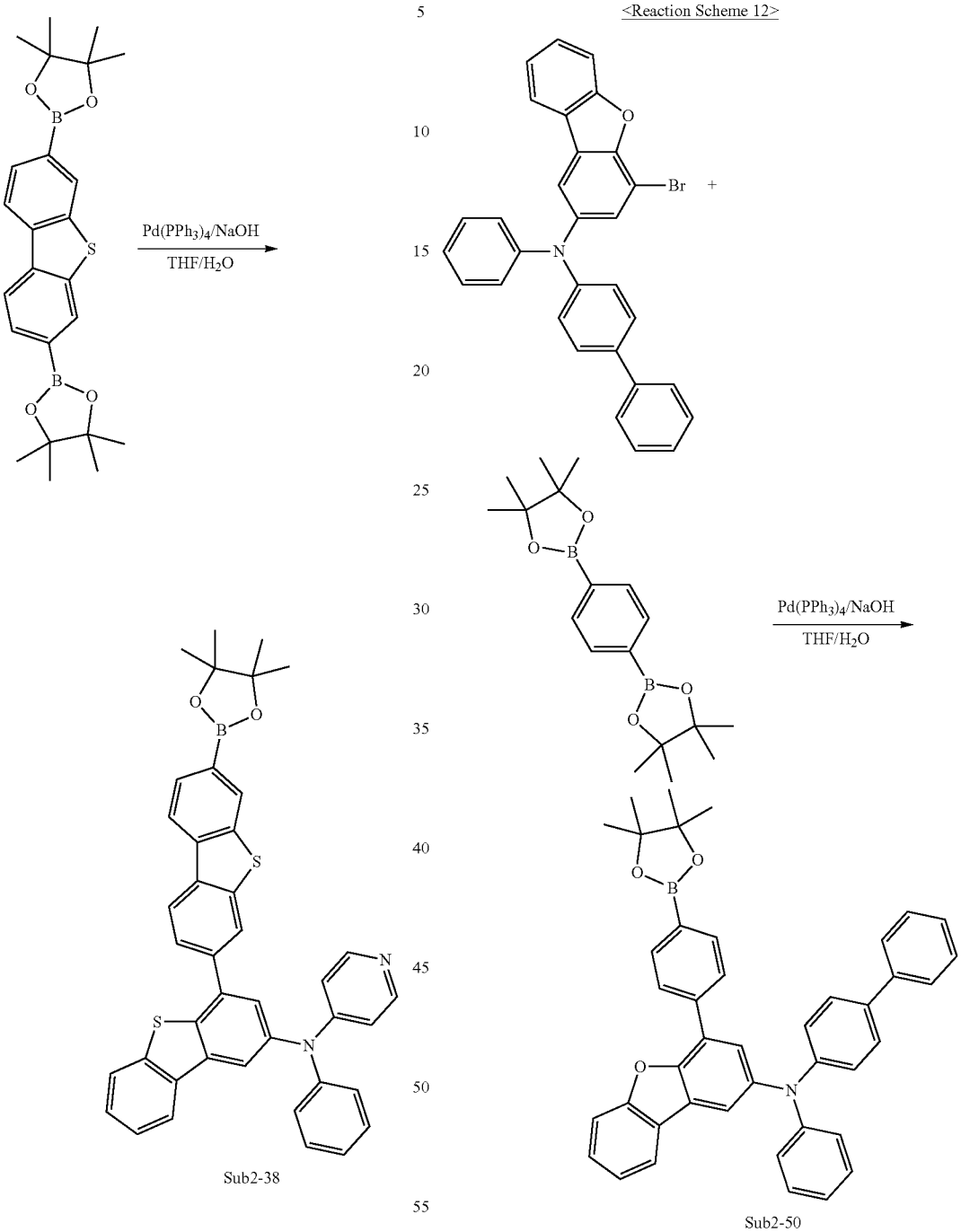

Sub2-38

3,7-bis(4,4,5,5-tetramethyl-1,3,2-dioxaborolan-2-yl) dibenzo[b,d]thiophene (50.5 g, 0.116 mol) was added to N-(4-bromodibenzo[b,d]thiophen-2-yl)-N-phenylpyridin-4-amine (50 g, 0.116 mol) and dissolved with THF (231 mL) and H₂O (80 mL). Pd(PPh₃)₄ (4 g, 0.003 mol) and NaOH (13.9 g, 0.347 mol) were added the solution, and the reaction was carried out at 75° C. When the reaction was completed, 70 g (yield: 91%) of the product Sub 2-38 was obtained by using the same manner as in the synthesis method of Sub 1-1.

Sub2-50

1,4-bis(4,4,5,5-tetramethyl-1,3,2-dioxaborolan-2-yl)benzene (33.7 g, 0.10 mol) was added to N-([1,1'-biphenyl]-4-yl)-4-bromo-N-phenyldibenzo[b,d]furan-2-amine (50 g, 0.10 mol) and dissolved in THF (200 mL) and H₂O (70 mL). Pd(PPh₃)₄ (3.5 g, 0.003 mol) and NaOH (12.2 g, 0.305 mol) were added the solution, and the reaction was carried out at 75° C. When the reaction was completed, 58 g (yield: 92.8%) of the product Sub 2-50 was obtained by using the same manner as in the synthesis method of Sub 1-1.

The compounds belonging to Sub 2 may be, but not limited to, the following compounds, and Table 2 shows the FD-MS values of the compounds belonging to Sub 2.
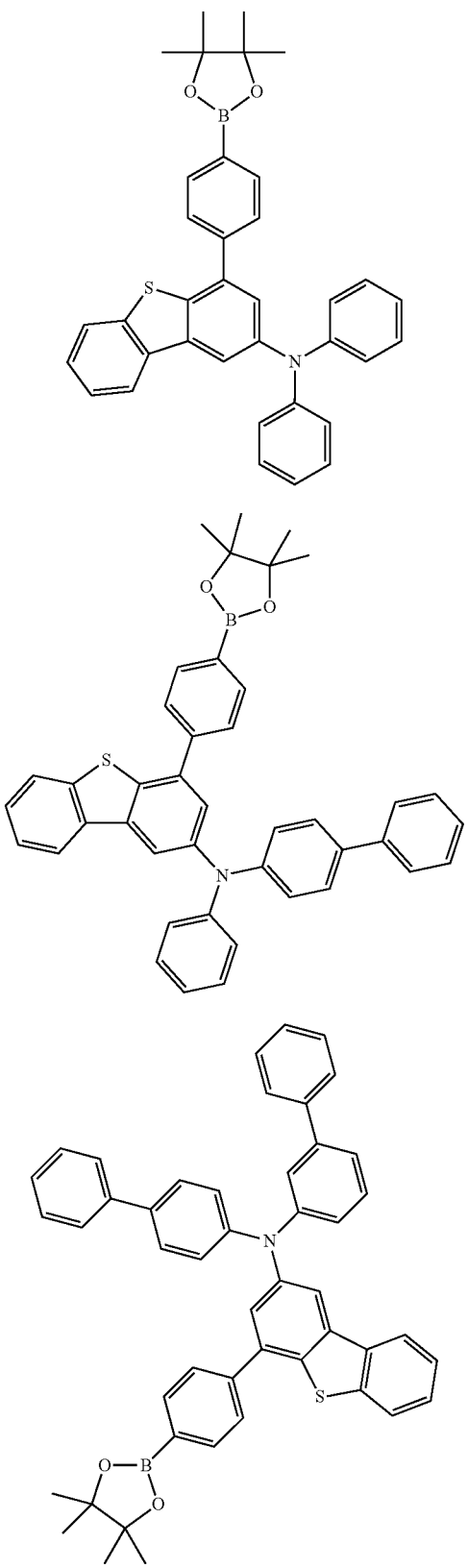
Sub2-1
Sub2-2
Sub2-3
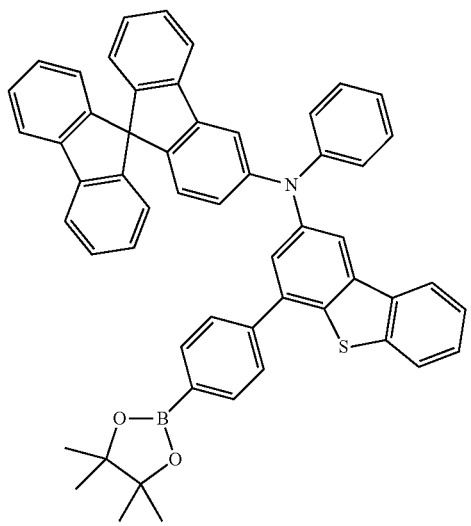
Sub2-4
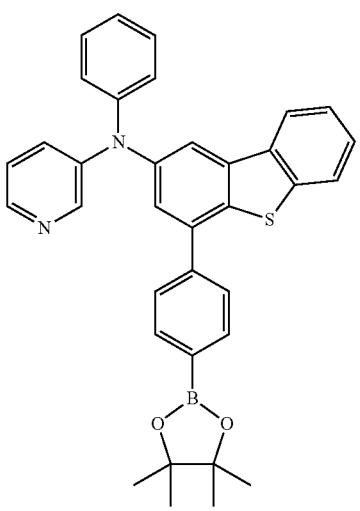
Sub2-5
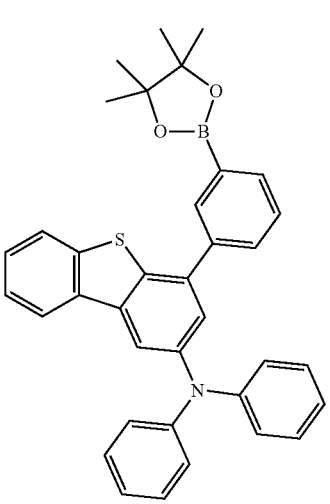
Sub2-6

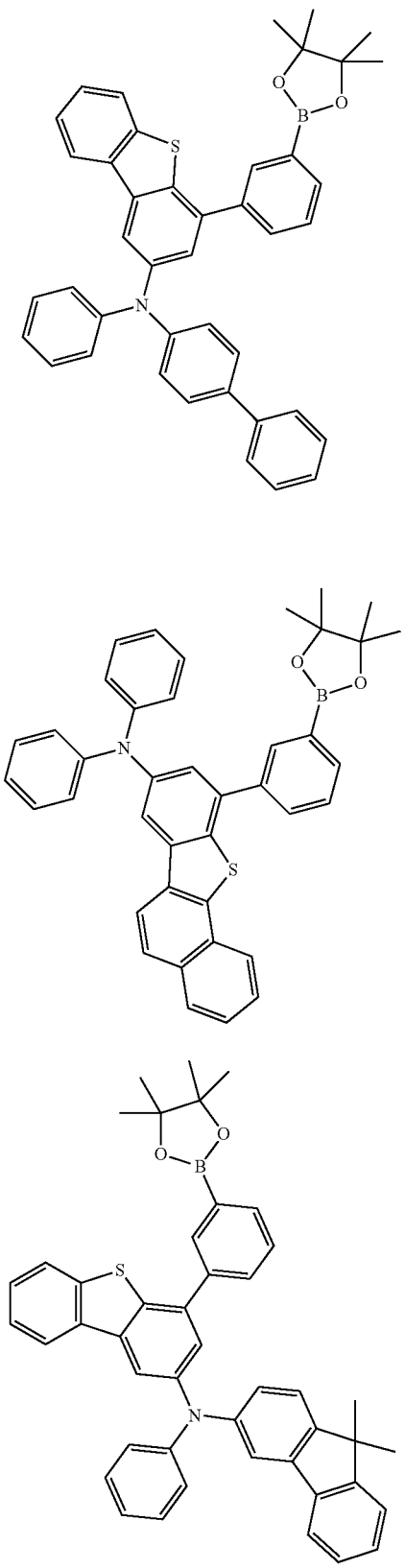
Sub2-7
Sub2-8
Sub2-9
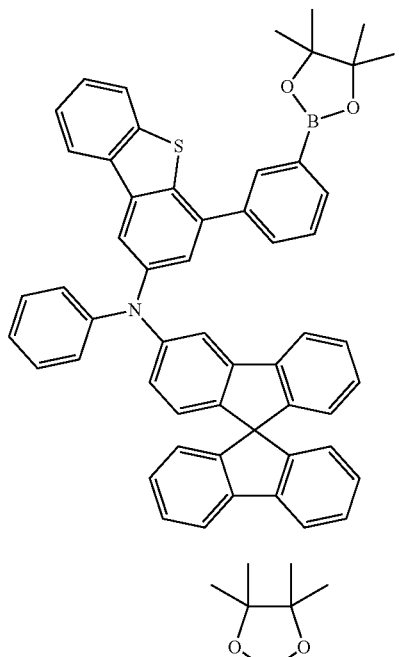
Sub2-10
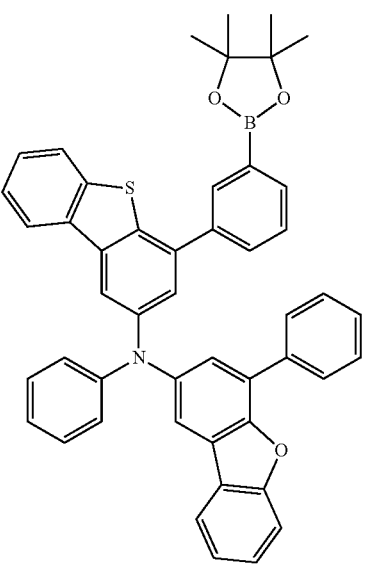
Sub2-11
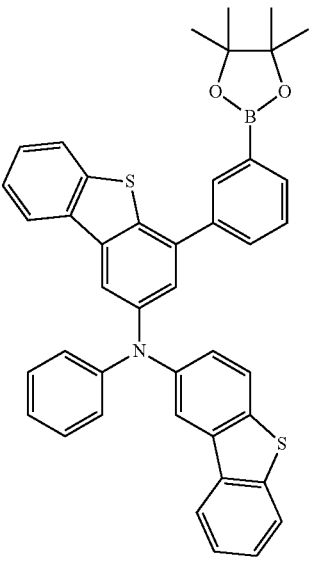
Sub2-12

91
-continued
Sub2-13
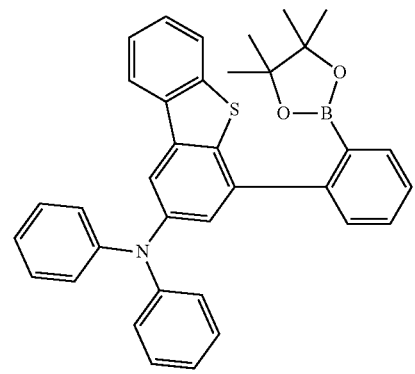
Sub2-14
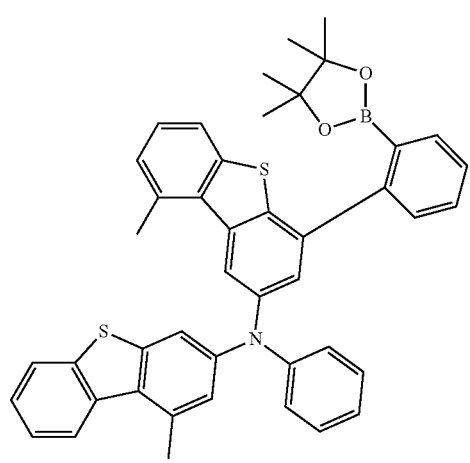
Sub2-15
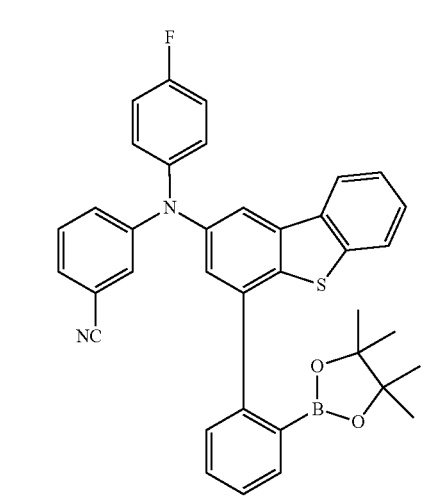
92
-continued
Sub2-16
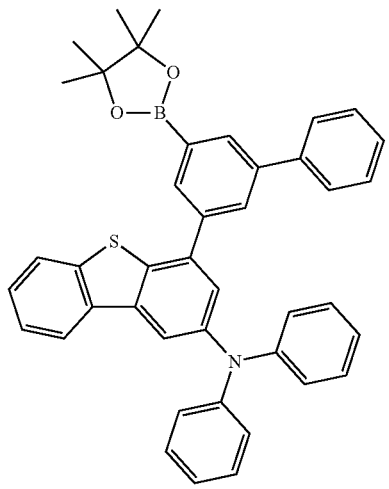
Sub2-17
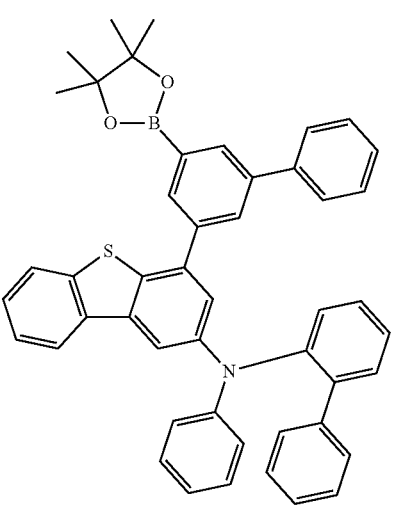
Sub2-18
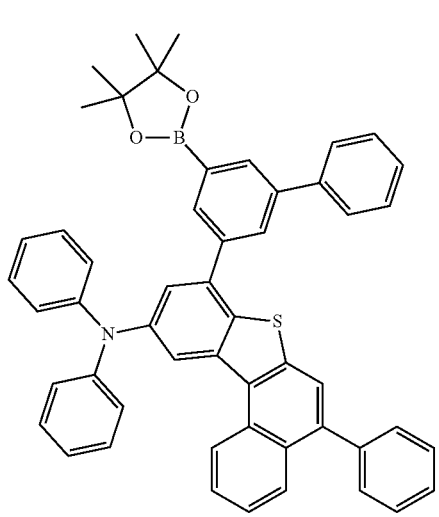

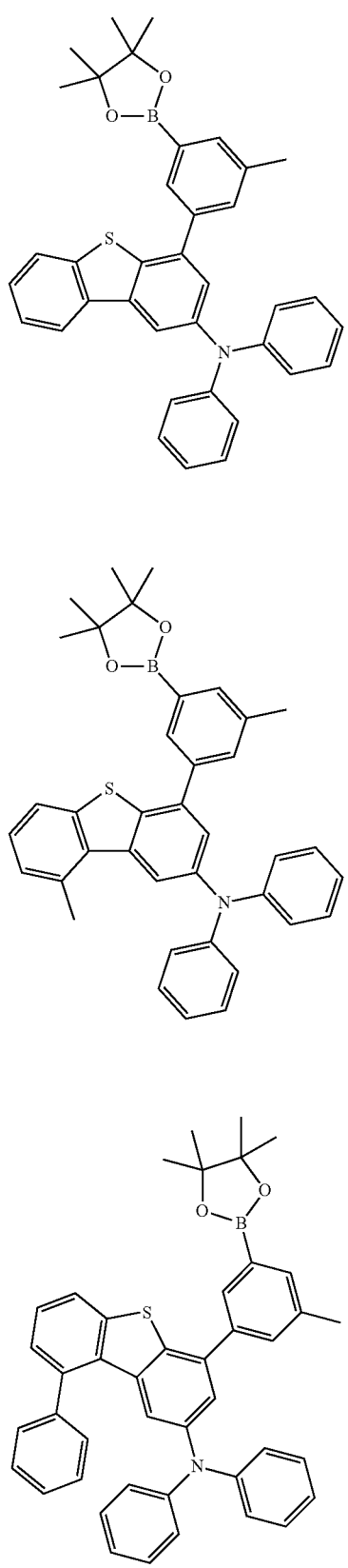
Sub2-19
Sub2-20
Sub2-21
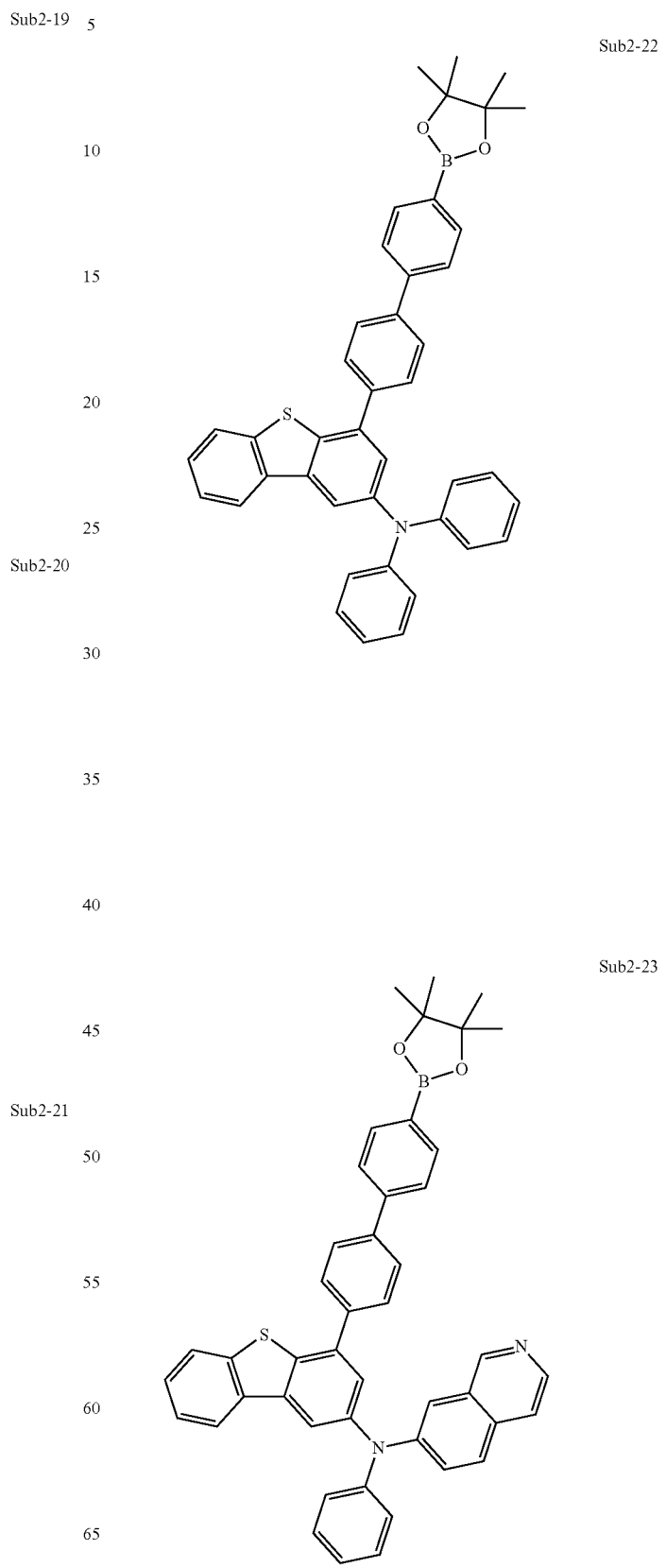
Sub2-22
Sub2-23

Sub2-24
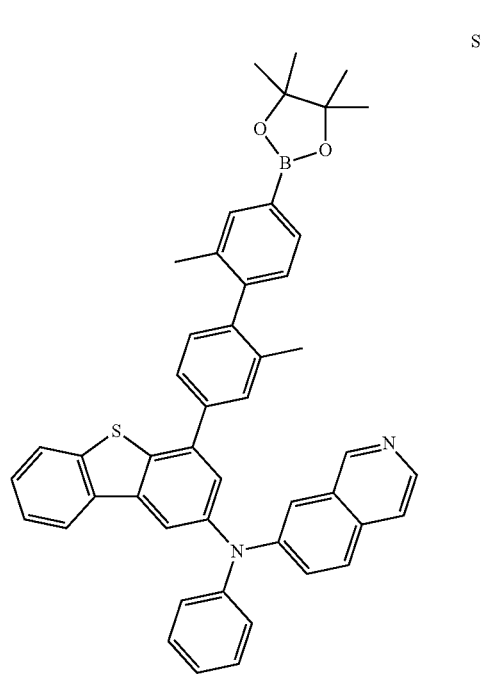
Sub2-26
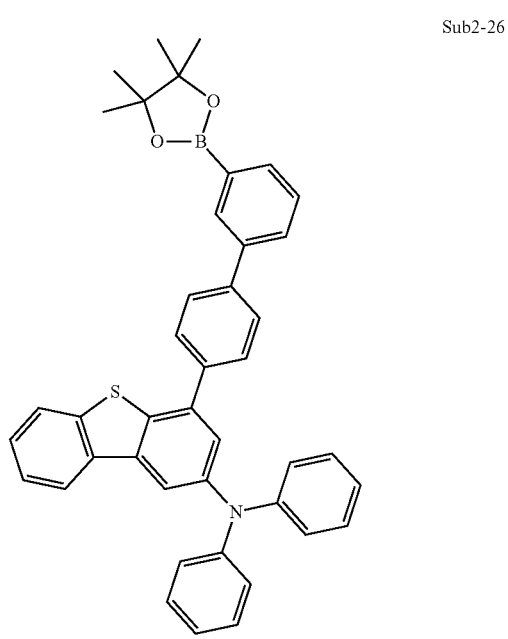
Sub2-25
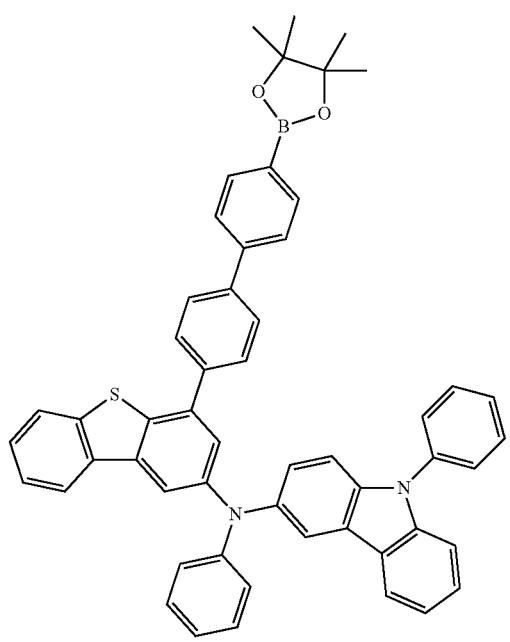
Sub2-27
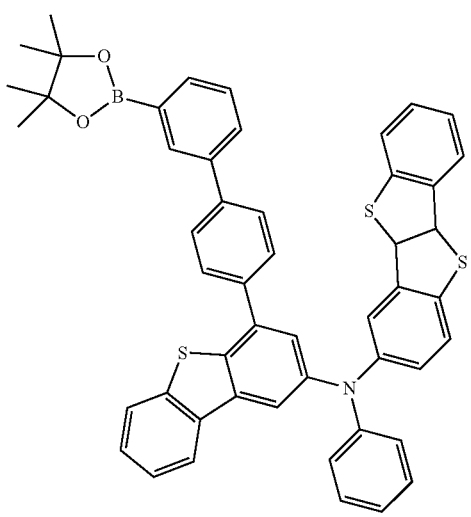

Sub2-28
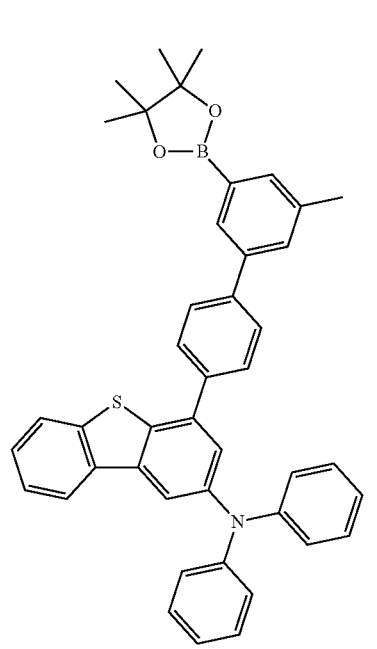
Sub2-30
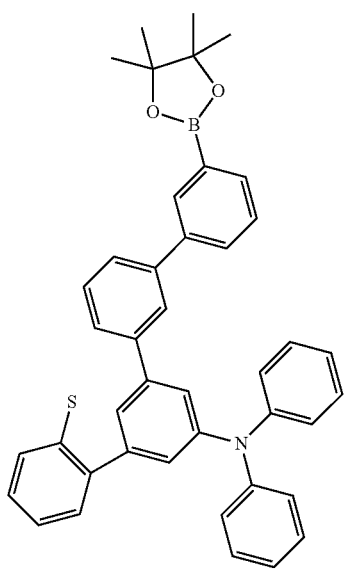
Sub2-29
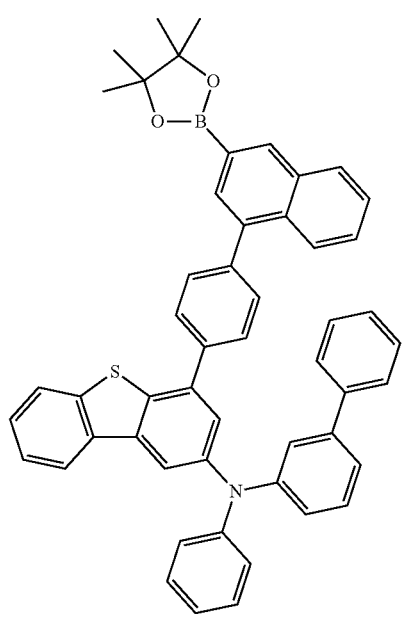
Sub2-31
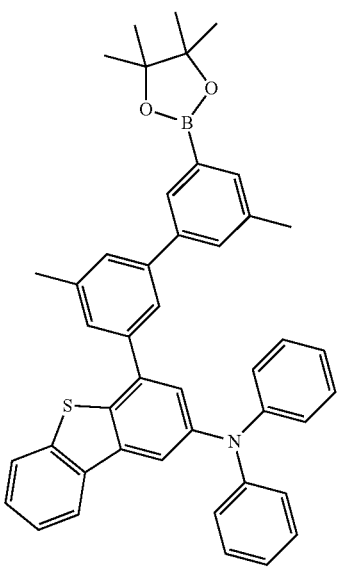

Sub2-32
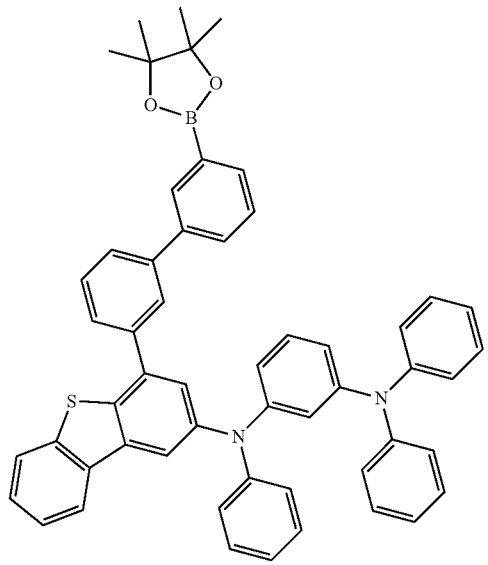
Sub2-33
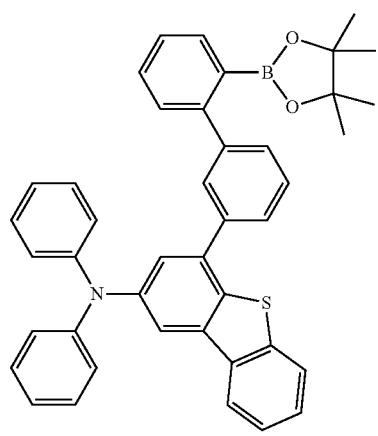
Sub2-34
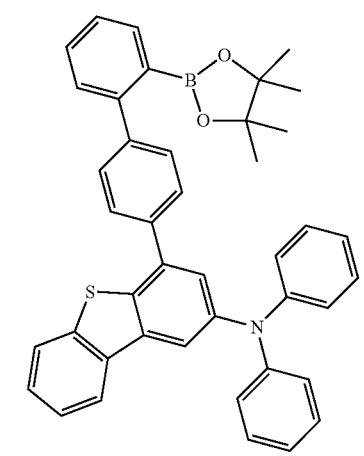
Sub2-35
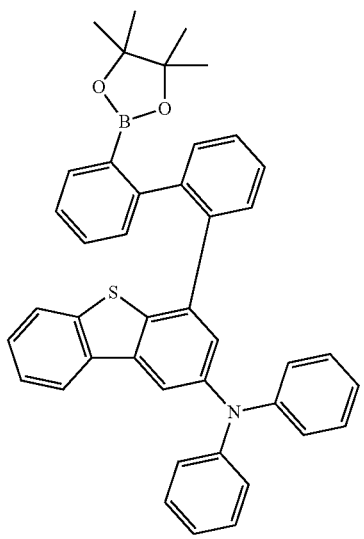
Sub2-36
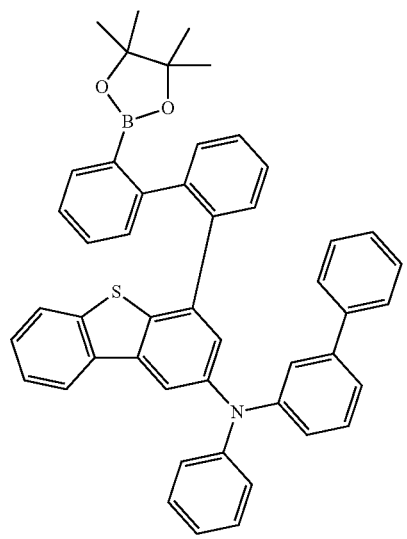
Sub2-37
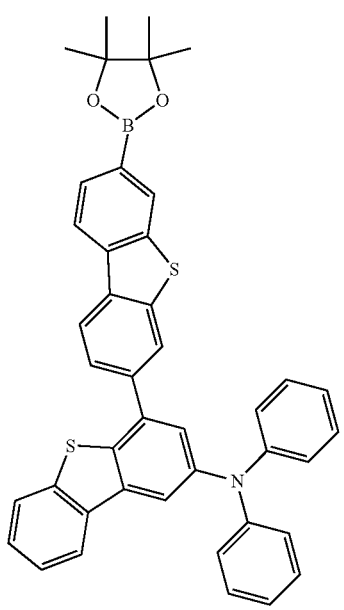

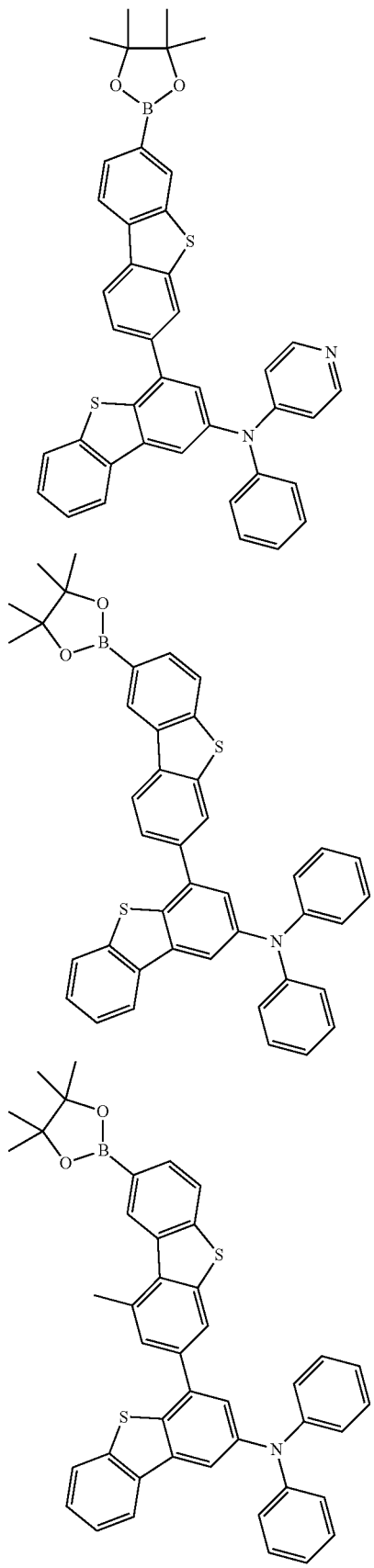
Sub2-38
Sub2-39
Sub2-40
Sub2-41
Sub2-42

Sub2-43
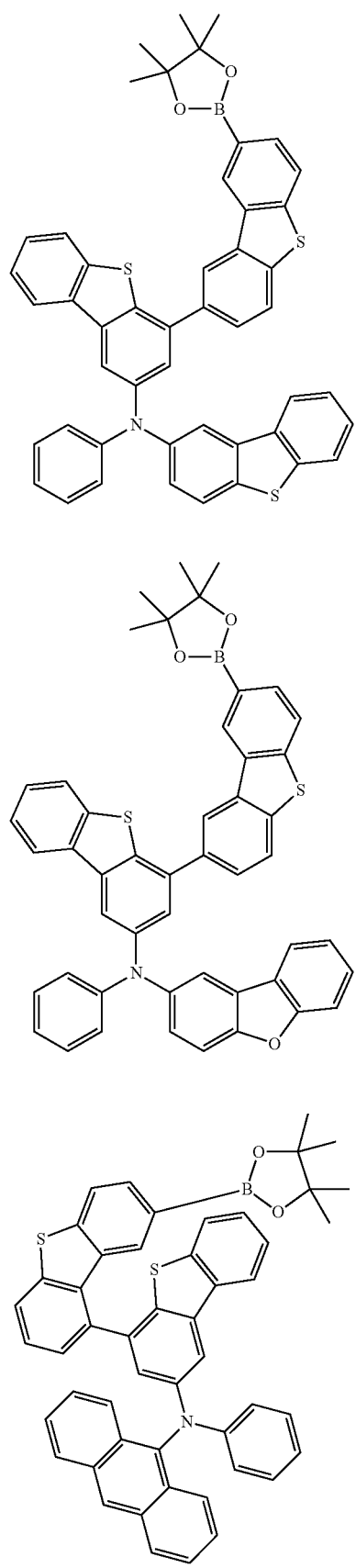
Sub2-44
Sub2-45
Sub2-46
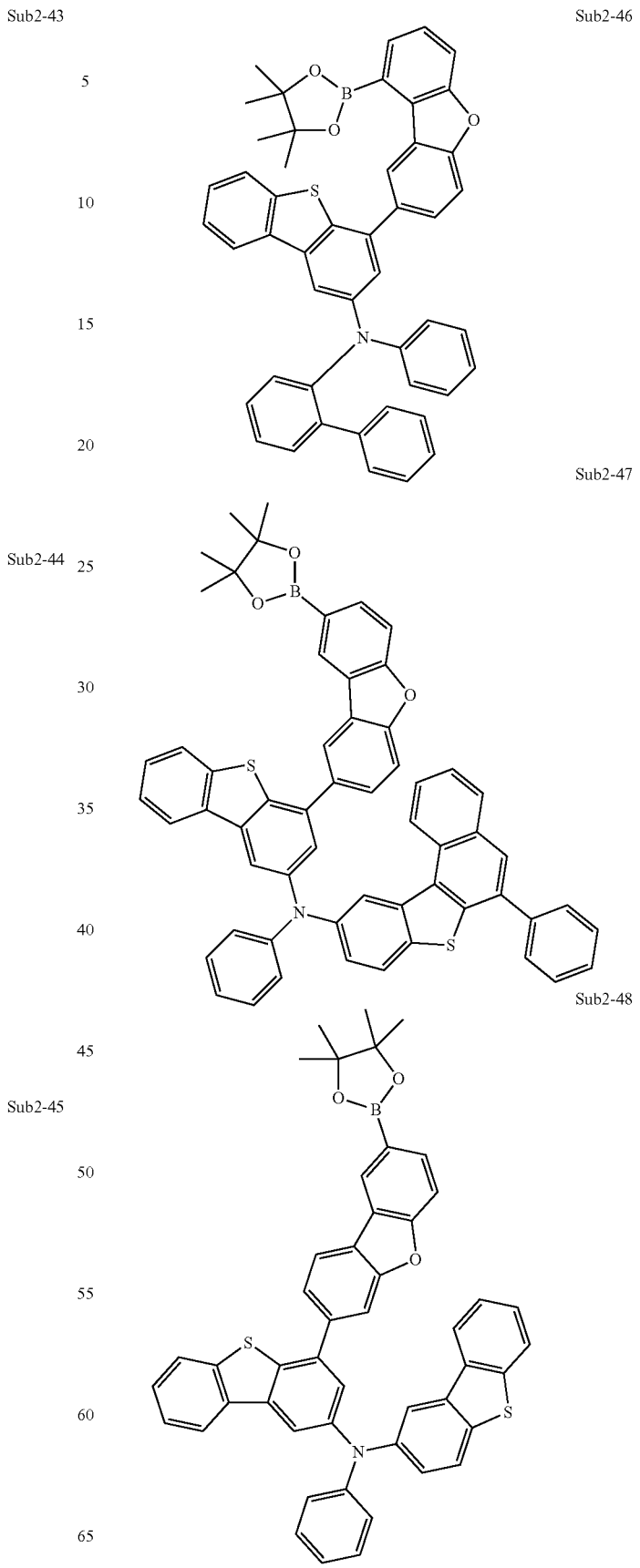
Sub2-47
Sub2-48

Sub2-49
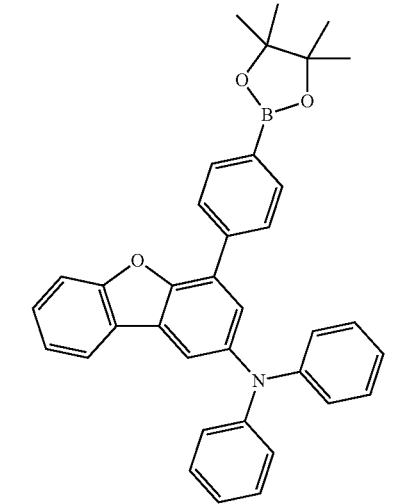
Sub2-50
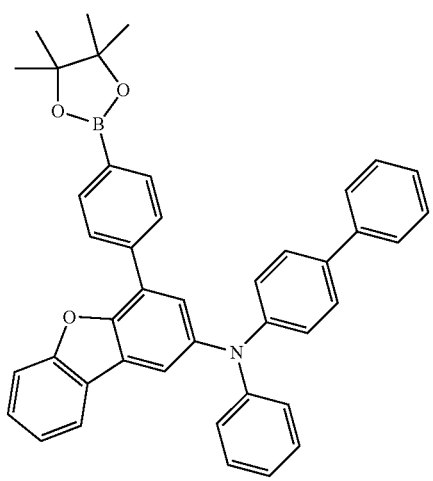
Sub2-51
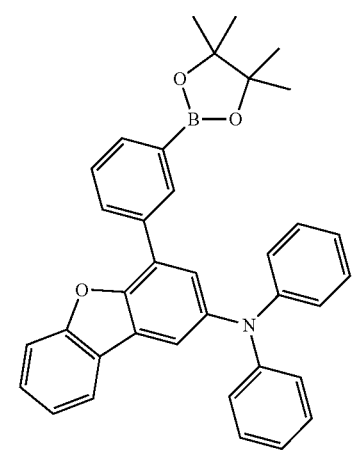
Sub2-52
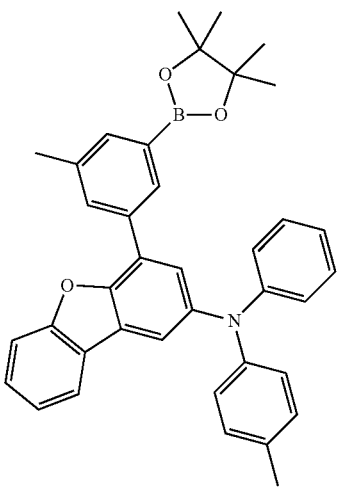
Sub2-53
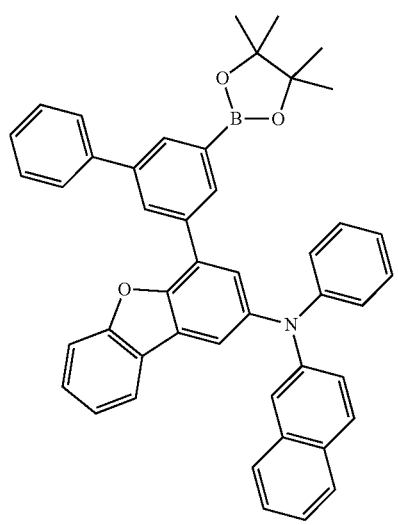
Sub2-54
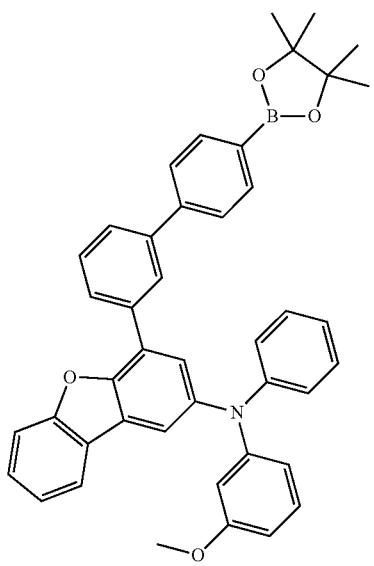

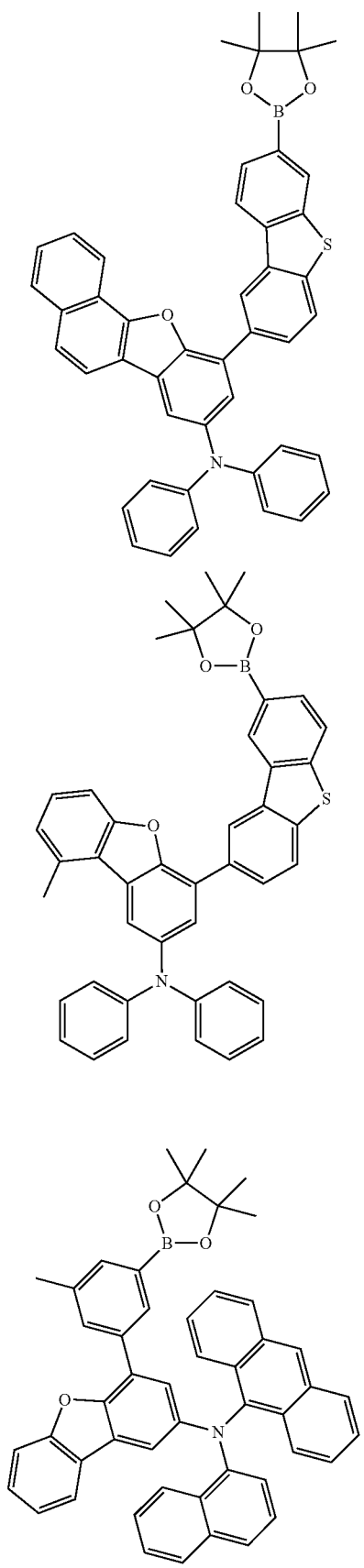
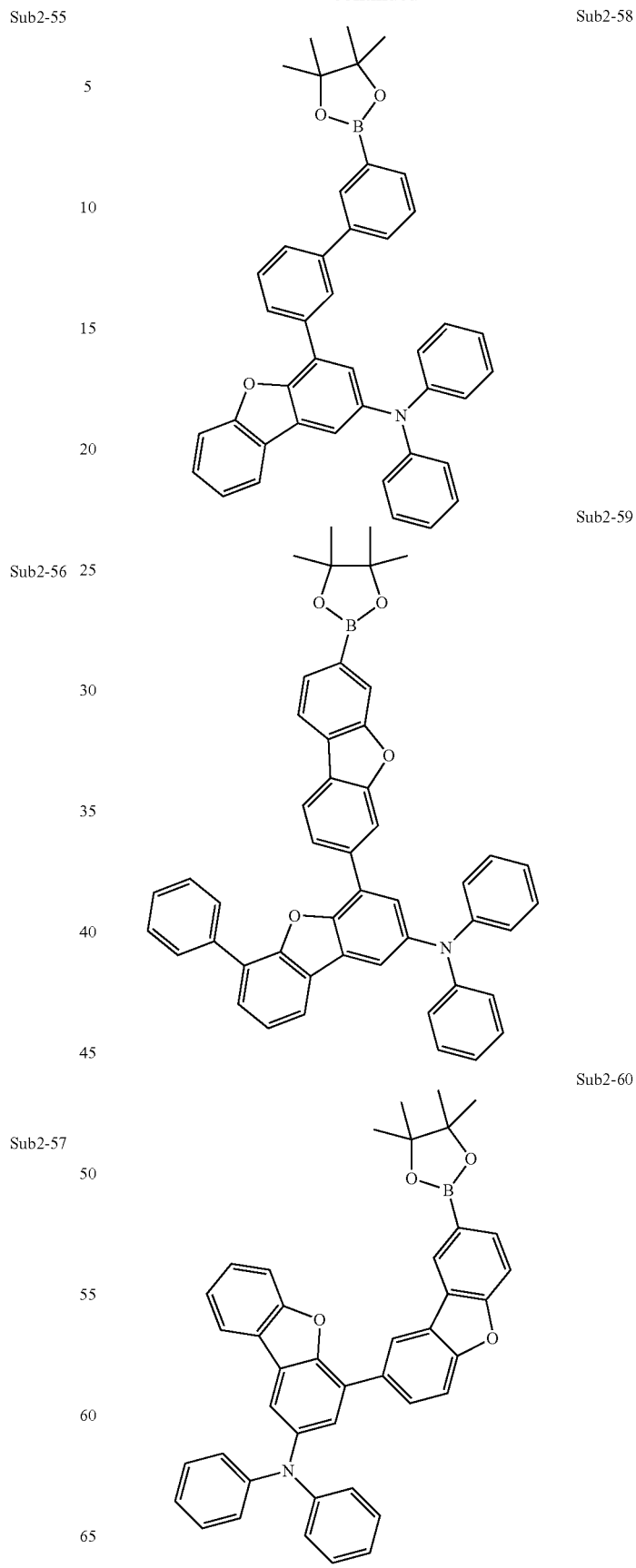

Sub2-61
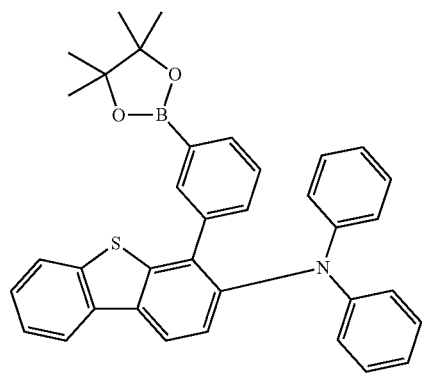
Sub2-62
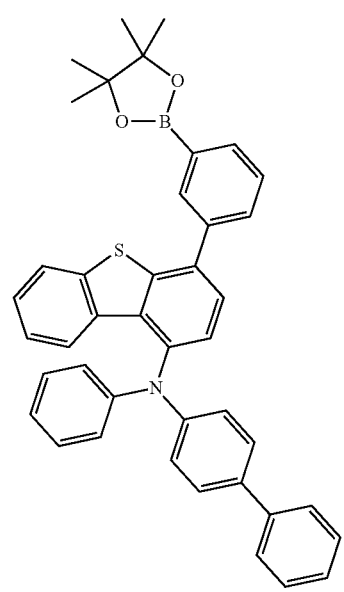
Sub2-63
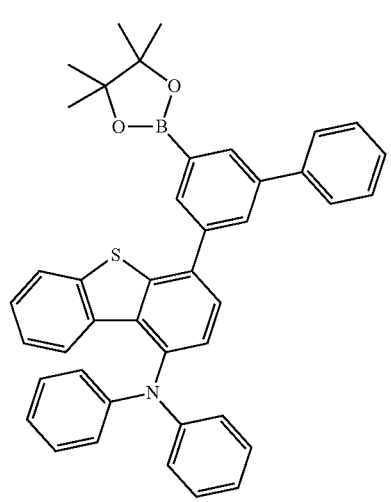
Sub2-64
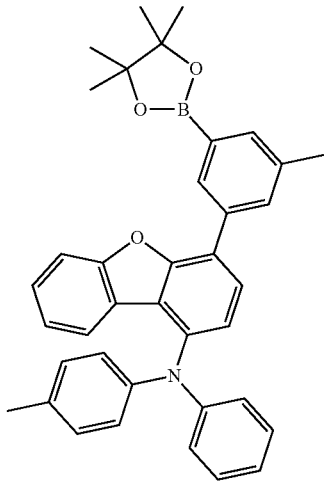
Sub2-65
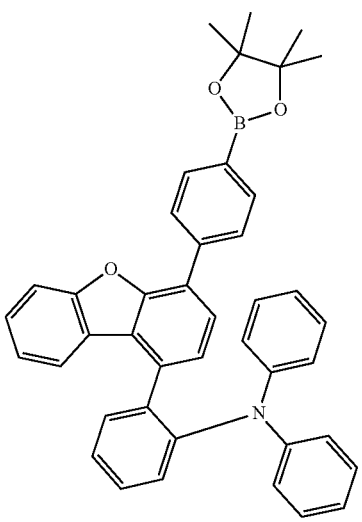
Sub2-66
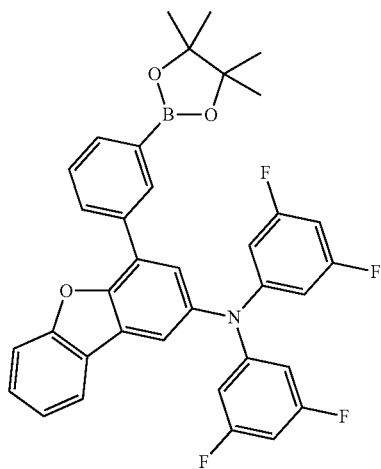

Sub2-67

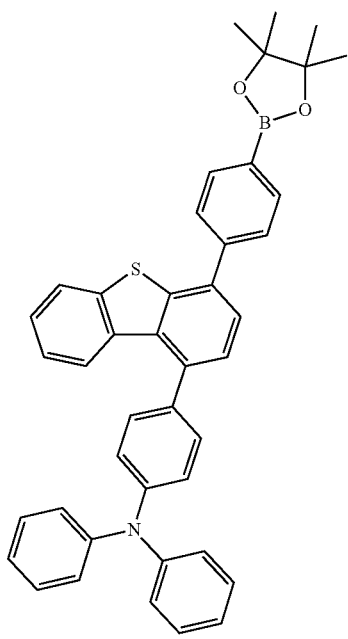

Sub2-68

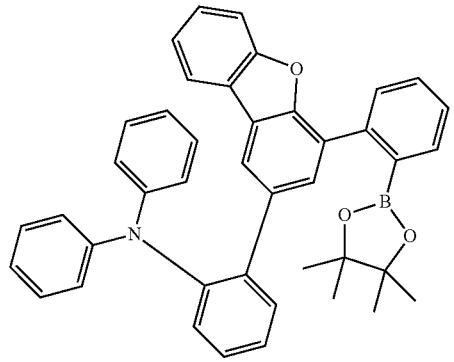

TABLE 2

| Compound | FD-MS | Compound | FD-MS |
| --- | --- | --- | --- |
| Sub 2-1 | m/z = 553.22 ($C_{36}H_{32}BNO_2S$ = 553.53) | Sub 2-2 | m/z = 629.26 ($C_{42}H_{36}BNO_2S$ = 629.63) |
| Sub 2-3 | m/z = 705.29 ($C_{48}H_{40}BNO_2S$ = 705.72) | Sub 2-4 | m/z = 791.30 ($C_{55}H_{42}BNO_2S$ = 791.82) |
| Sub 2-5 | m/z = 554.22 ($C_{35}H_{31}BN_2O_2S$ = 554.52) | Sub 2-6 | m/z = 553.22 ($C_{36}H_{32}BNO_2S$ = 553.53) |
| Sub 2-7 | m/z = 629.26 ($C_{42}H_{36}BNO_2S$ = 629.63) | Sub 2-8 | m/z = 603.24 ($C_{40}H_{34}BNO_2S$ = 603.59) |
| Sub 2-9 | m/z = 669.29 ($C_{45}H_{40}BNO_2S$ = 669.69) | Sub 2-10 | m/z = 791.30 ($C_{55}H_{42}BNO_2S$ = 791.82) |
| Sub 2-11 | m/z = 719.27 ($C_{48}H_{38}BNO_3S$ = 719.71) | Sub 2-12 | m/z = 659.21 ($C_{42}H_{34}BNO_2S_2$ = 659.67) |
| Sub 2-13 | m/z = 553.22 ($C_{36}H_{32}BNO_2S$ = 553.53) | Sub 2-14 | m/z = 687.24 ($C_{44}H_{38}BNO_2S_2$ = 687.72) |
| Sub 2-15 | m/z = 596.21($C_{37}H_{30}BFN_2O_2S$ = 596.53) | Sub 2-16 | m/z = 629.63 ($C_{42}H_{36}BNO_2S$ = 629.26) |
| Sub 2-17 | m/z = 705.29 ($C_{48}H_{40}BNO_2S$ = 705.72) | Sub 2-18 | m/z = 755.30 ($C_{52}H_{42}BNO_2S$ = 755.78) |
| Sub 2-19 | m/z = 567.24 ($C_{37}H_{34}BNO_2S$ = 567.55) | Sub 2-20 | m/z = 581.26 ($C_{38}H_{36}BNO_2S$ = 581.58) |
| Sub 2-21 | m/z = 643.27 ($C_{43}H_{38}BNO_2S$ = 643.65) | Sub 2-22 | m/z = 629.26 ($C_{42}H_{36}BNO_2S$ = 629.63) |
| Sub 2-23 | m/z = 680.27 ($C_{45}H_{37}BN_2O_2S$ = 680.67) | Sub 2-24 | m/z = 708.30 ($C_{47}H_{41}BN_2O_2S$ = 708.73) |
| Sub 2-25 | m/z = 794.31 ($C_{54}H_{43}BN_2O_2S$ = 794.82) | Sub 2-26 | m/z = 629.26 ($C_{42}H_{36}BNO_2S$ = 629.63) |
| Sub 2-27 | m/z = 793.23 ($C_{50}H_{40}BNO_2S_3$ = 793.87) | Sub 2-28 | m/z = 643.27 ($C_{43}H_{38}BNO_2S$ = 643.65) |
| Sub 2-29 | m/z = 755.30 ($C_{52}H_{42}BNO_2S$ = 755.78) | Sub 2-30 | m/z = 629.26 ($C_{42}H_{36}BNO_2S$ = 629.63) |
| Sub 2-31 | m/z = 657.29 ($C_{44}H_{40}BNO_2S_3$ = 657.68) | Sub 2-32 | m/z = 796.33 ($C_{54}H_{45}BN_2O_2S$ = 796.84) |
| Sub 2-33 | m/z = 629.26 ($C_{42}H_{36}BNO_2S$ = 629.63) | Sub 2-34 | m/z = 629.26 ($C_{42}H_{36}BNO_2S$ = 629.63) |
| Sub 2-35 | m/z = 629.26 ($C_{42}H_{36}BNO_2S$ = 629.63) | Sub 2-36 | m/z = 705.29 ($C_{48}H_{40}BNO_2S$ = 705.72) |
| Sub 2-37 | m/z = 659.21 ($C_{42}H_{34}BNO_2S_2$ = 659.67) | Sub 2-38 | m/z = 660.21 ($C_{44}H_{33}BN_2O_2S_2$ = 660.66) |
| Sub 2-39 | m/z = 659.21 ($C_{42}H_{34}BNO_2S_2$ = 659.67) | Sub 2-40 | m/z = 673.23 ($C_{43}H_{36}BNO_2S_2$ = 673.70) |
| Sub 2-41 | m/z = 709.23 ($C_{46}H_{36}BNO_2S_2$ = 709.73) | Sub 2-42 | m/z = 735.24 ($C_{48}H_{38}BNO_2S_2$ = 735.77) |
| Sub 2-43 | m/z = 765.20 ($C_{48}H_{36}BNO_2S_3$ = 765.81) | Sub 2-44 | m/z = 749.22 ($C_{48}H_{36}BNO_3S_2$ = 749.75) |
| Sub 2-45 | m/z = 759.24 ($C_{50}H_{38}BNO_2S_2$ = 759.79) | Sub 2-46 | m/z = 719.27 ($C_{48}H_{38}BNO_3S$ = 719.71) |
| Sub 2-47 | m/z = 875.27 ($C_{58}H_{42}BNO_3S_2$ = 875.91) | Sub 2-48 | m/z = 749.22 ($C_{48}H_{36}BNO_3S_2$ = 749.75) |
| Sub 2-49 | m/z = 537.25 ($C_{36}H_{32}BNO_3$ = 537.47) | Sub 2-50 | m/z = 613.28 ($C_{42}H_{36}BNO_3$ = 613.56) |
| Sub 2-51 | m/z = 537.25 ($C_{36}H_{32}BNO_3$ = 537.47) | Sub 2-52 | m/z = 565.28 ($C_{38}H_{36}BNO_3$ = 565.52) |
| Sub 2-53 | m/z = 663.29 ($C_{46}H_{38}BNO_3$ = 663.62) | Sub 2-54 | m/z = 643.29 ($C_{43}H_{38}BNO_4$ = 643.59) |
| Sub 2-55 | m/z = 693.25 ($C_{46}H_{36}BNO_3S$ = 693.67) | Sub 2-56 | m/z = 657.25 ($C_{43}H_{36}BNO_3S$ = 657.64) |
| Sub 2-57 | m/z = 537.25 ($C_{36}H_{32}BNO_3$ = 537.47) | Sub 2-58 | m/z = 613.28 ($C_{42}H_{36}BNO_3$ = 613.56) |
| Sub 2-59 | m/z = 703.29 ($C_{48}H_{38}BNO_4$ = 703.65) | Sub 2-60 | m/z = 627.26 ($C_{42}H_{34}BNO_4$ = 627.55) |
| Sub 2-61 | m/z = 553.22 ($C_{36}H_{32}BNO_2S$ = 553.53) | Sub 2-62 | m/z = 629.26 ($C_{42}H_{36}BNO_2S$ = 629.63) |
| Sub 2-63 | m/z = 629.26 ($C_{42}H_{36}BNO_2S$ = 629.63) | Sub 2-64 | m/z = 565.28 ($C_{38}H_{36}BNO_3$ = 565.52) |
| Sub 2-65 | m/z = 613.28 ($C_{42}H_{36}BNO_3$ = 613.56) | Sub 2-66 | m/z = 537.25 ($C_{36}H_{32}BNO_3$ = 537.47) |
| Sub 2-67 | m/z = 629.26 ($C_{42}H_{36}BNO_2S$ = 629.63) | Sub 2-68 | m/z = 613.28 ($C_{42}H_{36}BNO_3$ = 613.56) |

III. Synthesis of Product

Sub1 (1 eq.) was added into a round bottom flask and dissolved in THF and water, then Sub 2 (1 eq.), $Pd_2(dba)_3$ (0.03 eq.), $(t-Bu)_3P$ (0.06 eq.) and NaOt-Bu (3 eq.) were added thereto and stirred at 75° C. for 6 hours. When the reaction was completed, the reaction product was extracted with $CH_2Cl_2$ and water. Then, the organic layer was dried with $MgSO_4$ and concentrated. Then, the concentrate was applied to silicagel column and recrystallized to obtain the final product.

1. Synthesis Example of P-1

<Reaction Scheme 13>

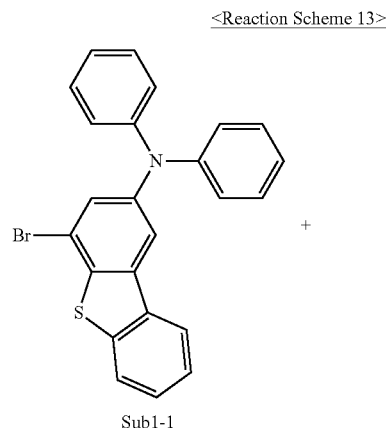

Sub1-1

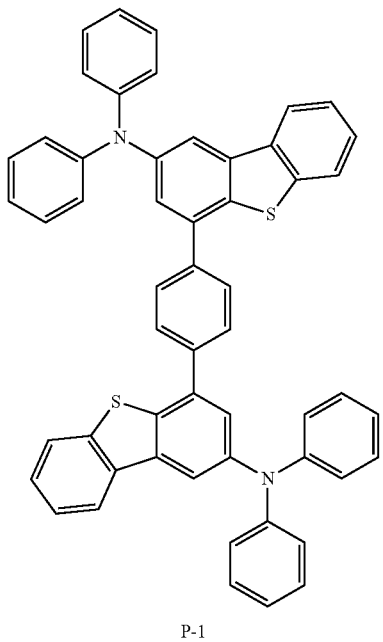

P-1

Sub 1-1 (10 g, 0.023 mol) obtained in the above synthesis and Sub 2-1 (12.8 g, 0.023 mol) were dissolved in THF (46 ml) and $H_2O$ (15 mL). After $Pd(PPh_3)_4$ (0.8 g, 0.0006 mol) and NaOH (2.8 g, 0.069 mol) were added the solution, the reaction was carried out at 75° C. When the reaction was completed, the reaction product was extracted with $CH_2Cl_2$ and water. Then, the organic layer was dried with $MgSO_4$ and concentrated. Then, the concentrate was applied to silicagel column and recrystallized to obtain 15 g (yield: 83%) of the product P-1.

2. Synthesis Example of P-10

<Reaction Scheme 14>

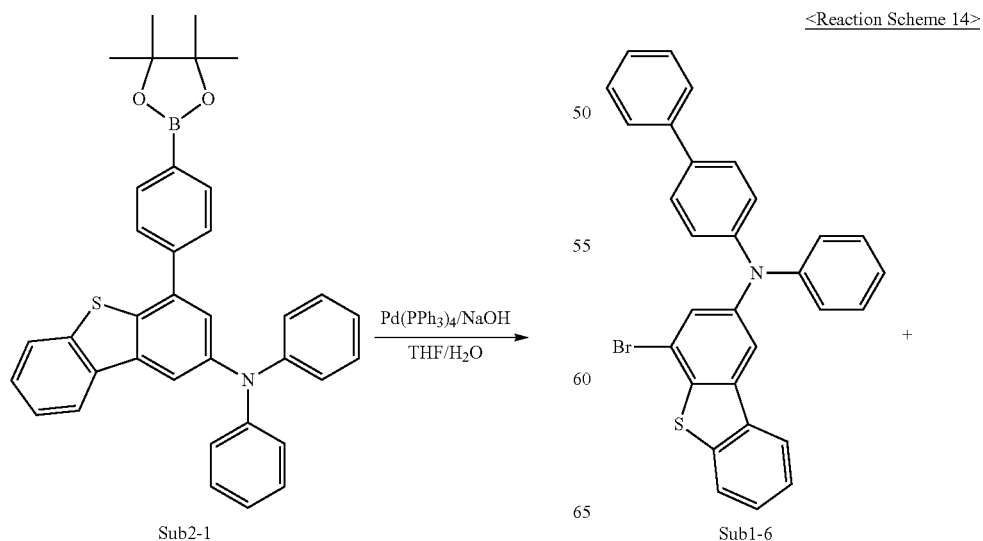

Sub2-1

Sub1-6

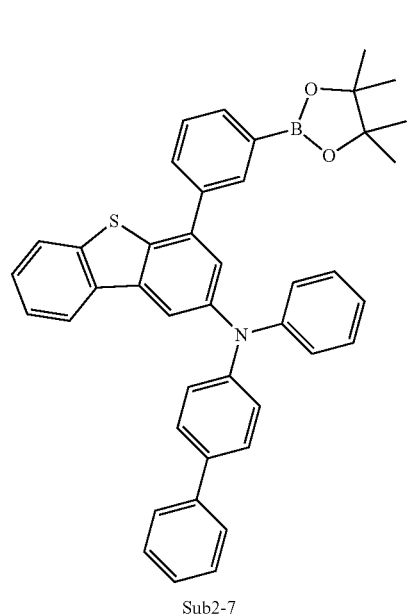
3. Synthesis Example of P-24
<Reaction Scheme 15>
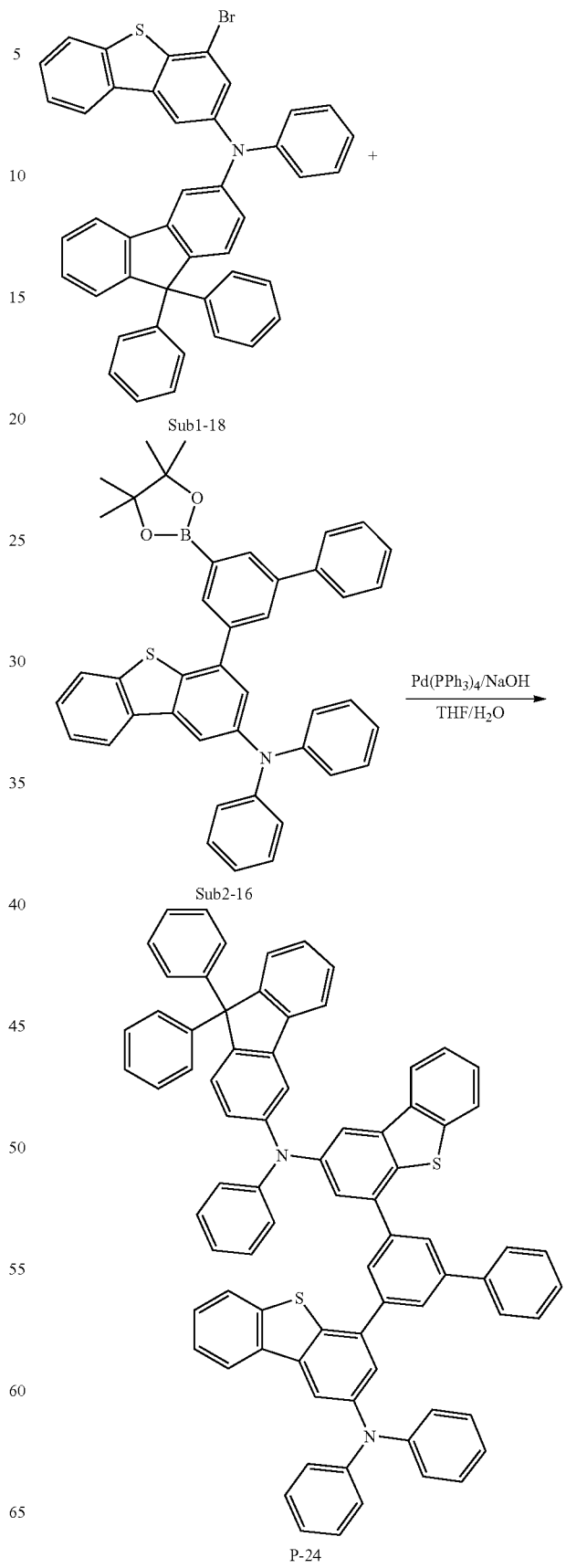
Sub 1-6 (15 g, 0.029 mol) obtained in the above synthesis and Sub 2-7 (18.6 g, 0.029 mol) were dissolved in THF (60 ml) and H₂O (20 mL). After Pd(PPh)₄ (1 g, 0.0009 mol) and NaOH (3.55 g, 0.088 mol) were added the solution, the reaction was carried out at 75° C. When the reaction was completed, 23 g (yield: 84%) of the product P-10 was obtained by using the same manner as in the synthesis method of P-1.

Sub 1-18 (10 g, 0.015 mol) obtained in the above synthesis and Sub 2-16 (9.4 g, 0.015 mol) were dissolved in THF (30 ml) and H₂O (10 mL). After Pd(PPh₃)₄ (0.5 g, 0.0005 mol) and NaOH (1.8 g, 0.044 mol) were added the solution, the reaction was carried out at 75° C. When the reaction was completed, 14 g (yield: 85.8%) of the product P-24 was obtained by using the same manner as in the synthesis method of P-1.

4. Synthesis Example of P-26

<Reaction Scheme 16>

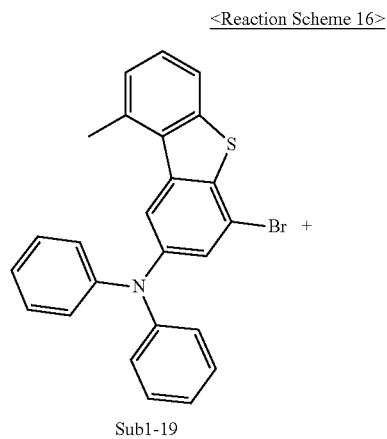

Sub1-19

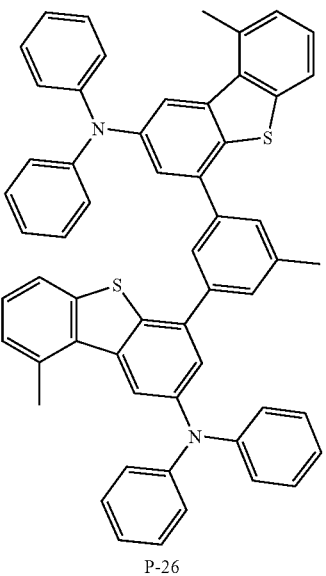

P-26

Sub 1-19 (13 g, 0.029 mol) obtained in the above synthesis and Sub 2-20 (17 g, 0.029 mol) were dissolved in THF (60 ml) and H₂O (20 mL). After Pd(PPh₃)₄ (1 g, 0.0008 mol) and NaOH (3.5 g, 0.087 mol) were added the solution, the reaction was carried out at 75° C. When the reaction was completed, 22 g (yield: 91.7%) of the product P-26 was obtained by using the same manner as in the synthesis method of P-1.

5. Synthesis Example of P-30

<Reaction Scheme 17>

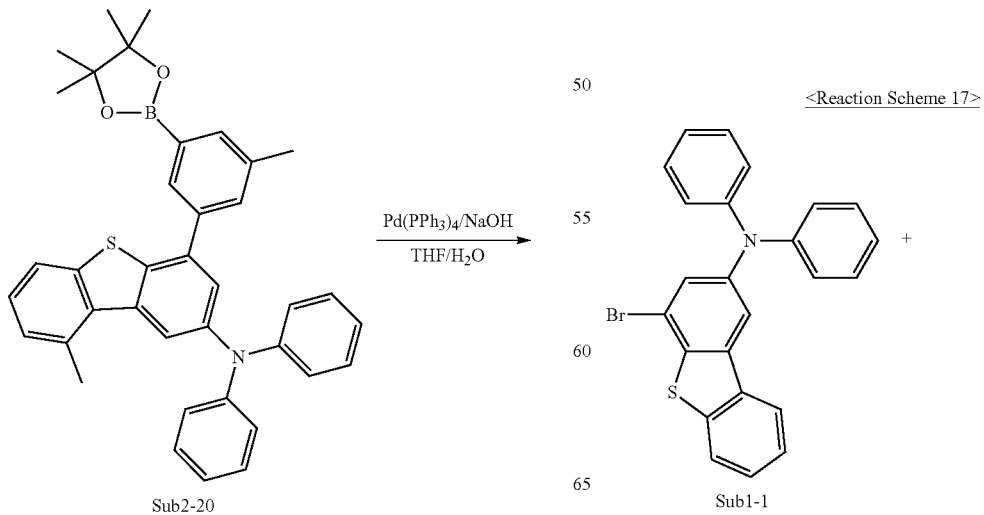

6. Synthesis Example of P-40

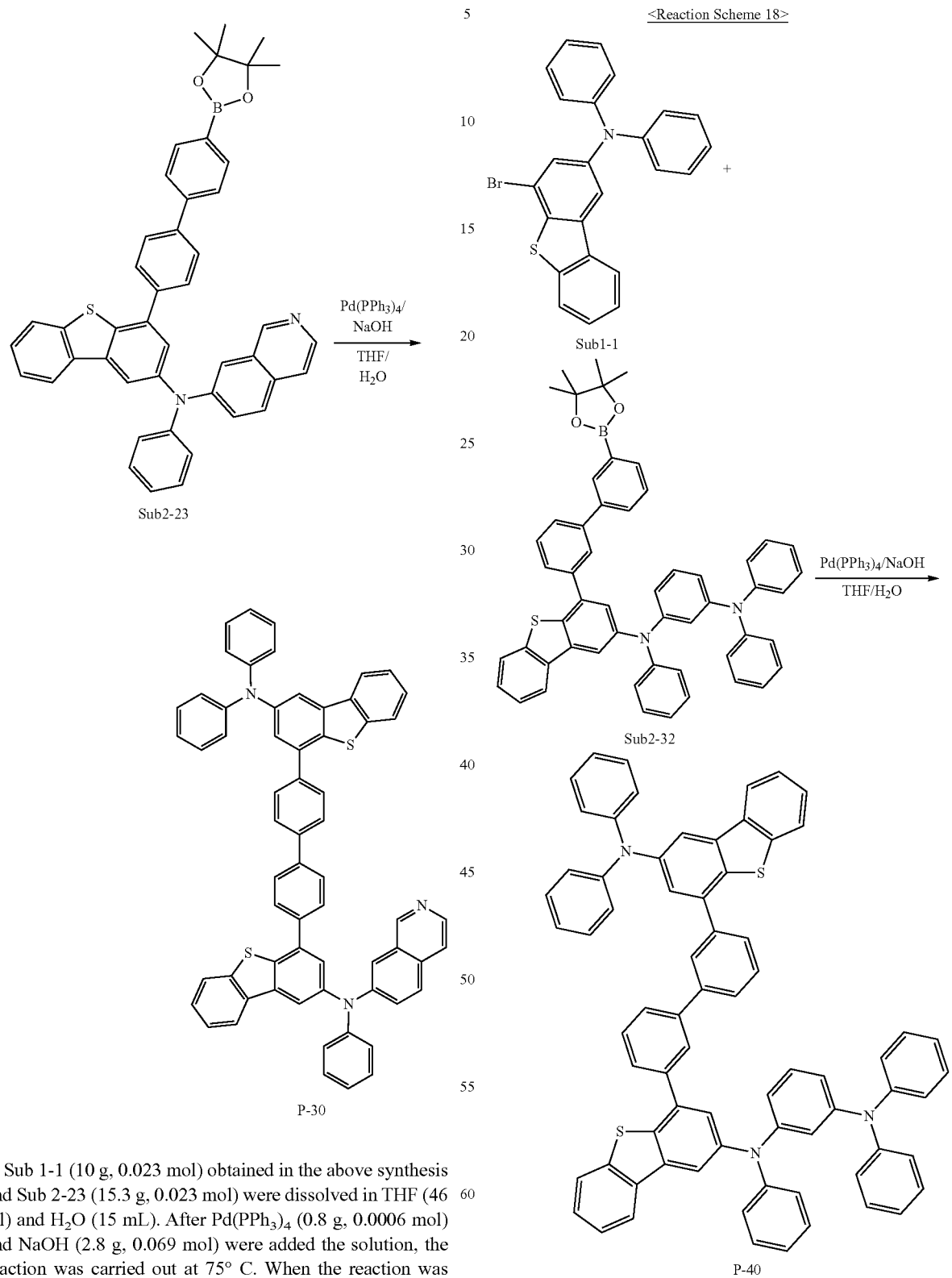

Sub 1-1 (10 g, 0.023 mol) obtained in the above synthesis and Sub 2-23 (15.3 g, 0.023 mol) were dissolved in THF (46 ml) and H₂O (15 mL). After Pd(PPh₃)₄ (0.8 g, 0.0006 mol) and NaOH (2.8 g, 0.069 mol) were added the solution, the reaction was carried out at 75° C. When the reaction was completed, 14 g (yield: 68.7%) of the product P-30 was obtained by using the same manner as in the synthesis method of P-1.

Sub 1-1 (10 g, 0.023 mol) obtained in the above synthesis and Sub 2-32 (18 g, 0.023 mol) were dissolved in THF (46 ml) and H₂O (15 mL). After Pd(PPh₃)₄ (0.8 g, 0.0006 mol) and NaOH (2.8 g, 0.069 mol) were added the solution, the reaction was carried out at 75° C. When the reaction was completed, 17 g (yield: 74%) of the product P-40 was obtained by using the same manner as in the synthesis method of P-1.

7. Synthesis Example of P-51

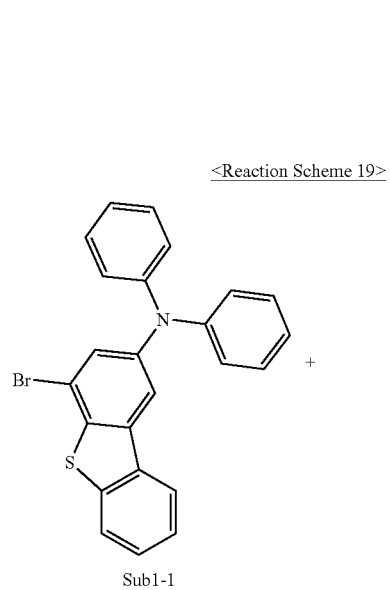

Sub 1-1 (10 g, 0.023 mol) obtained in the above synthesis and Sub 2-32 (17 g, 0.023 mol) were dissolved in THF (46 ml) and H₂O (15 mL). After Pd(PPh₃)₄ (0.8 g, 0.0006 mol) and NaOH (2.8 g, 0.069 mol) were added the solution, the reaction was carried out at 75° C. When the reaction was completed, 18 g (yield: 81%) of the product P-51 was obtained by using the same manner as in the synthesis method of P-1.

8. Synthesis Example of P-65

123
-continued
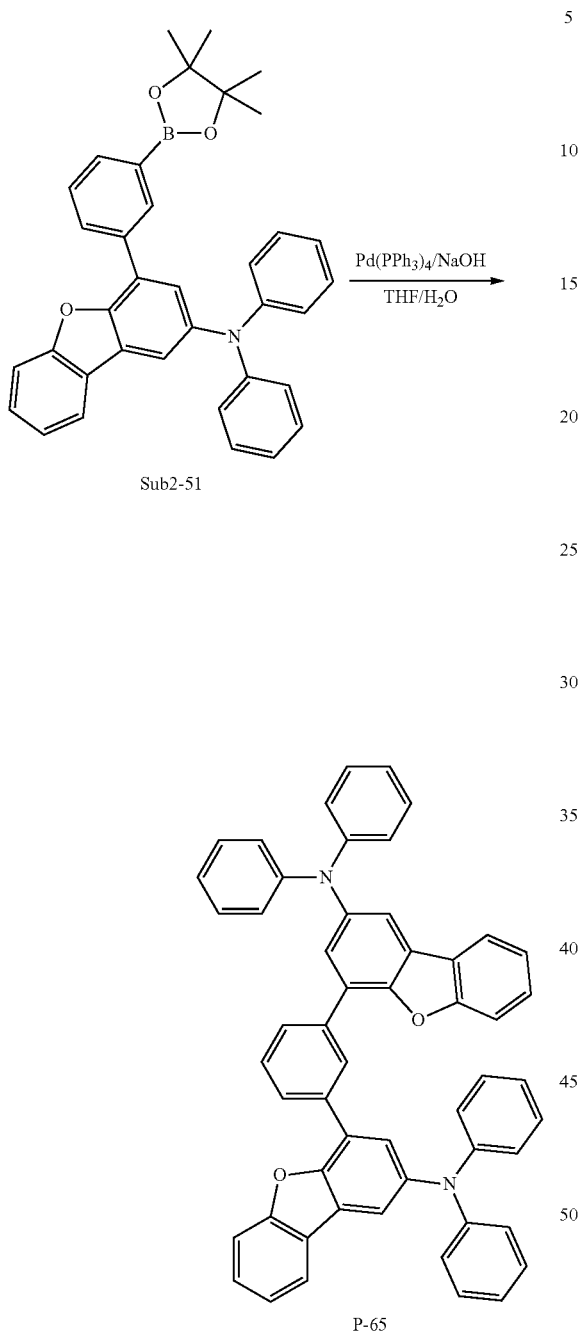
Sub 1-30 (15 g, 0.036 mol) obtained in the above synthesis and Sub 2-51 (19.5 g, 0.036 mol) were dissolved in THF (72 ml) and H$_2$O (24 mL). After Pd(PPh$_3$)$_4$ (1.25 g, 0.001 mol) and NaOH (4.3 g, 0.10 mol) were added the solution, the reaction was carried out at 75° C. When the reaction was completed, 24 g (yield: 89%) of the product P-65 was obtained by using the same manner as in the synthesis method of P-1.
124
9. Synthesis Example of P-74
<Reaction Scheme 21>
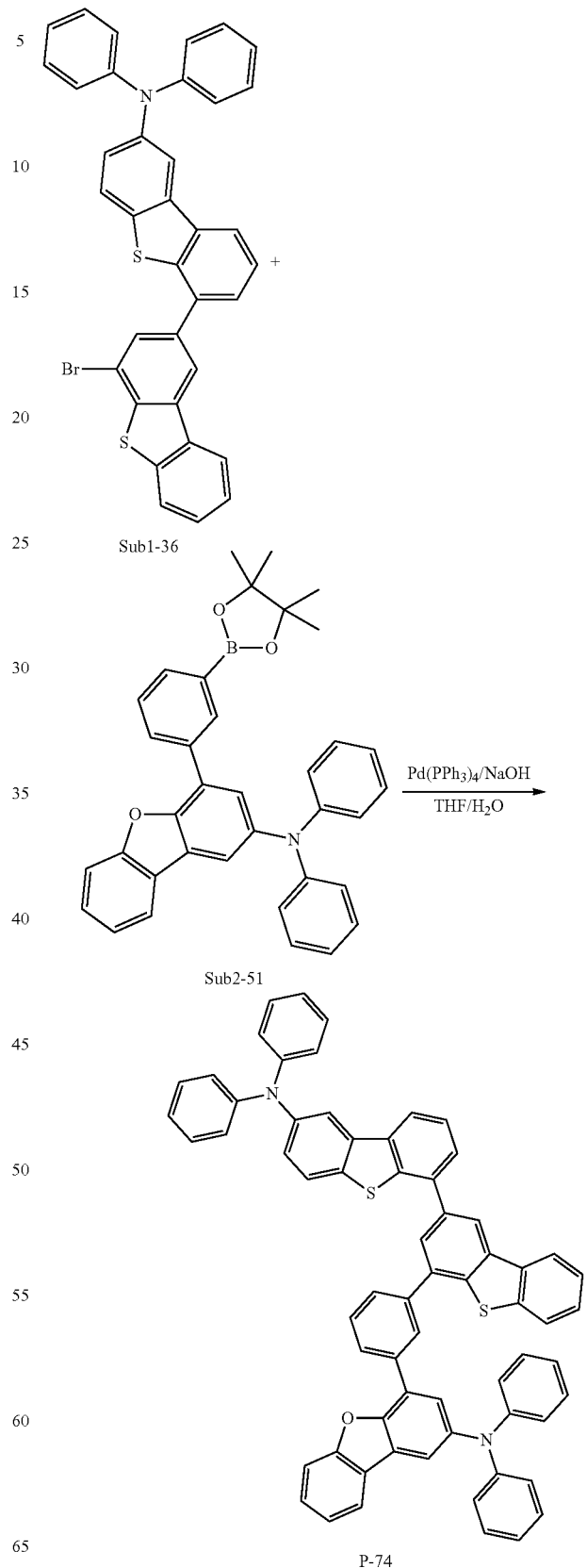

Sub 1-36 (15 g, 0.025 mol) obtained in the above synthesis and Sub 2-51 (13.1 g, 0.025 mol) were dissolved in THF (50 ml) and H$_2$O (15 mL). After Pd(PPh$_3$)$_4$ (0.85 g, 0.0007 mol) and NaOH (2.9 g, 0.073 mol) were added the solution, the reaction was carried out at 75° C. When the reaction was completed, 19 g (yield: 82%) of the product P-74 was obtained by using the same manner as in the synthesis method of P-1.

The FD-MS values of the compounds P-1 to P-64 prepared according to the above synthesis examples are shown in the following Table 3.

the emission-auxiliary layer to form a light emitting layer with a thickness of 30 nm.

Subsequently, (1,1'-biphenyl-4-olato)bis(2-methyl-8-quinolinolato)aluminum (abbreviated as "BAlq") was vacuum-deposited with a thickness of 10 nm on the light emitting layer to form a hole blocking layer, and a film of tris(8-quinolinolato)aluminum (hereinafter, "Alq$_3$") was formed with a thickness of 40 nm to form an electron transport layer. Thereafter, LiF being an alkali metal halide was deposited to a thickness of 0.2 nm as an electron injection layer, and then Al was deposited to a thickness of 150 nm to form a cathode.

TABLE 3

| Compound | FD-MS | Compound | FD-MS |
|---|---|---|---|
| P-1 | m/z = 776.23 (C$_{54}$H$_{36}$N$_2$S$_2$ = 777.02) | P-2 | m/z = 826.25 (C$_{58}$H$_{38}$N$_2$S$_2$ = 827.08) |
| P-3 | m/z = 902.28 (C$_{64}$H$_{42}$N$_2$S$_2$ = 903.17) | P-4 | m/z = 1028.33 (C$_{74}$H$_{48}$N$_2$S$_2$ = 1029.33) |
| P-5 | m/z = 1130.37 (C$_{82}$H$_{54}$N$_2$S$_2$ = 1131.47) | P-6 | m/z = 858.29 (C$_{59}$H$_{34}$D$_5$N$_3$S$_2$ = 859.13) |
| P-7 | m/z = 866.24 (C$_{60}$H$_{38}$N$_2$OS$_2$ = 867.10) | P-8 | m/z = 882.22 (C$_{60}$H$_{38}$N$_2$S$_3$ = 883.16) |
| P-9 | m/z = 776.23 (C$_{54}$H$_{36}$N$_2$S$_2$ = 777.02) | P-10 | m/z = 928.29 (C$_{66}$H$_{44}$N$_2$S$_2$ = 929.21) |
| P-11 | m/z = 876.26 (C$_{62}$H$_{40}$N$_2$S$_2$ = 877.14) | P-12 | m/z = 952.29 (C$_{68}$H$_{44}$N$_2$S$_2$ = 953.23) |
| P-13 | m/z = 906.31 (C$_{64}$H$_{46}$N$_2$S$_2$ = 907.21) | P-14 | m/z = 1164.36 (C$_{85}$H$_{52}$N$_2$S$_2$ = 1165.49) |
| P-15 | m/z = 942.27 (C$_{66}$H$_{42}$N$_2$OS$_2$ = 943.20) | P-16 | m/z = 882.22 (C$_{60}$H$_{38}$N$_2$S$_3$ = 883.16) |
| P-17 | m/z = 776.23 (C$_{54}$H$_{36}$N$_2$S$_2$ = 777.02) | P-18 | m/z = 928.29 (C$_{66}$H$_{44}$N$_2$S$_2$ = 929.21) |
| P-19 | m/z = 924.27 (C$_{63}$H$_{44}$N$_2$S$_3$ = 925.24) | P-20 | m/z = 845.23 (C$_{57}$H$_{36}$FN$_3$S$_2$ = 846.05) |
| P-21 | m/z = 852.26 (C$_{60}$H$_{40}$N$_2$S$_2$ = 853.11) | P-22 | m/z = 928.29 (C$_{66}$H$_{44}$N$_2$S$_2$ = 929.21) |
| P-23 | m/z = 1028.33 (C$_{74}$H$_{48}$N$_2$S$_2$ = 1029.33) | P-24 | m/z = 1092.36 (C$_{79}$H$_{52}$N$_2$S$_2$ = 1093.42) |
| P-25 | m/z = 790.25 (C$_{55}$H$_{38}$N$_2$S$_2$ = 791.04) | P-26 | m/z = 818.28 (C$_{57}$H$_{42}$N$_2$S$_2$ = 819.10) |
| P-27 | m/z = 942.31 (C$_{67}$H$_{46}$N$_2$S$_2$ = 943.24) | P-28 | m/z = 942.31 (C$_{67}$H$_{46}$N$_2$S$_2$ = 943.24) |
| P-29 | m/z = 852.26 (C$_{60}$H$_{40}$N$_2$S$_2$ = 853.11) | P-30 | m/z = 903.27 (C$_{63}$H$_{41}$N$_3$S$_2$ = 904.16) |
| P-31 | m/z = 931.31 (C$_{65}$H$_{45}$N$_3$S$_2$ = 932.22) | P-32 | m/z = 1017.32 (C$_{72}$H$_{47}$N$_3$S$_2$ = 1018.31) |
| P-33 | m/z = 852.26 (C$_{60}$H$_{40}$N$_2$S$_2$ = 853.11) | P-34 | m/z = 1016.24 (C$_{68}$H$_{44}$N$_2$S$_4$ = 1017.35) |
| P-35 | m/z = 866.24 (C$_{61}$H$_{42}$N$_2$S$_2$ = 867.10) | P-36 | m/z = 1104.36 (C$_{80}$H$_{52}$N$_2$S$_2$ = 1105.43) |
| P-37 | m/z = 852.26 (C$_{60}$H$_{40}$N$_2$S$_2$ = 853.11) | P-38 | m/z = 880.29 (C$_{62}$H$_{44}$N$_2$S$_2$ = 881.17) |
| P-39 | m/z = 1110.4 (C$_{78}$H$_{54}$N$_2$S$_2$Si = 1111.51) | P-40 | m/z = 1019.34 (C$_{72}$H$_{49}$N$_3$S$_2$ = 1020.33) |
| P-41 | m/z = 852.26 (C$_{60}$H$_{40}$N$_2$S$_2$ = 853.11) | P-42 | m/z = 852.26 (C$_{60}$H$_{40}$O$_2$ = 853.11) |
| P-43 | m/z = 852.26 (C$_{60}$H$_{40}$N$_2$S$_2$ = 853.11) | P-44 | m/z = 1004.33 (C$_{72}$H$_{48}$N$_2$S$_2$ = 1005.31) |
| P-45 | m/z = 882.25 (C$_{60}$H$_{38}$N$_2$S$_3$ = 883.16) | P-46 | m/z = 983.25 (C$_{67}$H$_{41}$N$_3$S$_3$ = 984.27) |
| P-47 | m/z = 882.22 (C$_{60}$H$_{38}$N$_2$S$_3$ = 883.16) | P-48 | m/z = 896.24 (C$_{61}$H$_{40}$N$_2$S$_3$ = 897.19) |
| P-49 | m/z = 982.25 (C$_{68}$H$_{42}$N$_2$S$_3$ = 983.28) | P-50 | m/z = 972.27 (C$_{67}$H$_{44}$N$_2$S$_3$ = 973.28) |
| P-51 | m/z = 988.21 (C$_{66}$H$_{40}$N$_2$S$_4$ = 989.30) | P-52 | m/z = 1062.2 (C$_{72}$H$_{42}$N$_2$O$_2$S$_3$ = 1063.32) |
| P-53 | m/z = 1147.31 (C$_{80}$H$_{49}$N$_3$S$_3$ = 1148.47) | P-54 | m/z = 960.29 (C$_{66}$H$_{41}$FN$_2$OS$_2$ = 961.19) |
| P-55 | m/z = 1098.28 (C$_{76}$H$_{46}$N$_2$OS$_3$ = 1099.4) | P-56 | m/z = 1078.2 (C$_{72}$H$_{42}$N$_2$OS$_4$ = 1079.38) |
| P-57 | m/z = 760.25 (C$_{54}$H$_{36}$N$_2$OS = 760.96) | P-58 | m/z = 912.32 (C$_{66}$H$_{44}$N$_2$OS = 913.15) |
| P-59 | m/z = 760.25 (C$_{54}$H$_{36}$N$_2$OS = 760.96) | P-60 | m/z = 802.30 (C$_{57}$H$_{42}$N$_2$OS = 803.04) |
| P-61 | m/z = 936.32 (C$_{68}$H$_{44}$N$_2$OS = 937.17) | P-62 | m/z = 884.29 (C$_{61}$H$_{41}$FN$_2$O$_2$S = 885.07) |
| P-63 | m/z = 916.26 (C$_{64}$H$_{40}$N$_2$OS$_2$ = 917.16) | P-64 | m/z = 880.26 (C$_{61}$H$_{40}$N$_2$OS$_2$ = 881.12) |

Fabrication and Evaluation of Organic Electronic Element

[Example 1] Red OLED (an Emission-Auxiliary Layer)

After vacuum depositing N$^1$ (naphthalen-2-yl)-N$^4$,N$^4$-bis(4-(naphthalen-2-yl(phenyl)amino)phenyl)-N$^1$-phenylbenzene-1,4-diamine (abbreviated as "2-TNATA") film on an ITO layer (anode) to form a hole injection layer having a thickness of 60 nm, wherein the ITO layer was formed on a glass substrate, N,N'-bis(1-naphthalenyl)-N,N'-bis-phenyl-(1,1'-biphenyl)-4,4'-diamine (abbreviated as "NPB") film was vacuum-deposited with a thickness of 60 nm on the hole injection layer to form a hole transport layer.

Next, compound P-1 of the present invention was vacuum-deposited to a thickness of 20 nm on the hole transport layer to form an emission-auxiliary layer.

Next, 4,4'-N,N'-dicarbazole-biphenyl (hereinafter, "CBP") as a host material and bis-(1-phenylisoquinolyl)iridium(III)acetylacetonate (hereinafter "(piq)$_2$Ir(acac)") as a dopant material in a weight ratio of 95:5 were deposited on

[Example 2] to [Example 31]

The OLEDs were fabricated in the same manner as described in Example 1 except that the compounds of the present invention described in the following Table 4, instead of the compound P-1 of the present invention, were used as an emission-auxiliary layer material.

Comparative Example 1

The OLED was fabricated in the same manner as described in Example 1 except that an emission-auxiliary layer was not formed.

[Comparative Example 2] to [Comparative Example 4]

The OLEDs were fabricated in the same manner as described in Example 1 except that one of one of the following Comparative compounds A to C, instead of the compound P-1 of the present invention, was used as an emission-auxiliary layer material.

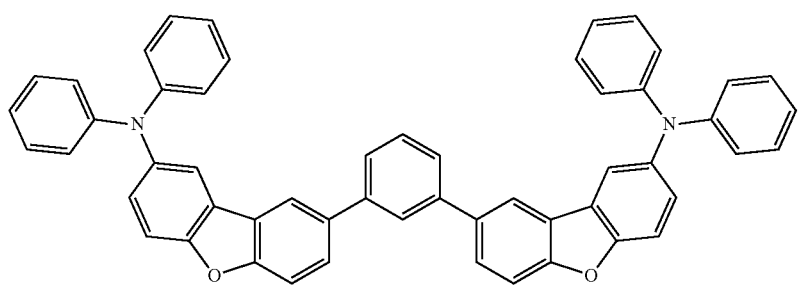

<Comp.compd A>

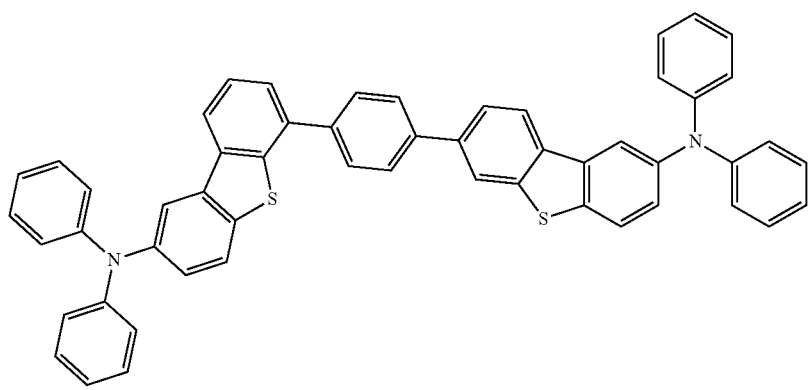

<Comp.compd B>

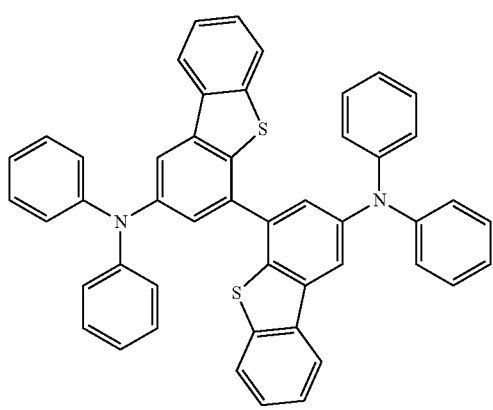

<Comp.compd C>

Electroluminescence (EL) characteristics were measured with a PR-650 (Photoresearch) by applying a forward bias DC voltage to the OLEDs prepared in Examples 1 to 31 of the present invention and Comparative Examples 1 to 4. And, the T95 life time was measured using a life time measuring apparatus manufactured by Macscience Inc. at reference brightness of 2500 cd/m$^2$. The measurement results are shown in Tables 4 below.

TABLE 4

|  | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| comp. Ex(1) | — | 6.0 | 32.9 | 2500.0 | 7.6 | 61.8 | 0.66 | 0.32 |
| comp. Ex(2) | comp. Com A | 5.8 | 24.5 | 2500.0 | 10.2 | 98.5 | 0.64 | 0.32 |
| comp. Ex(3) | comp. Com B | 5.7 | 20.2 | 2500.0 | 12.4 | 95.6 | 0.64 | 0.34 |
| comp. Ex(4) | comp. Com C | 5.5 | 16.9 | 2500.0 | 14.8 | 99.9 | 0.65 | 0.34 |
| Ex. (1) | P-1 | 5.0 | 11.9 | 2500.0 | 21.0 | 118.5 | 0.64 | 0.34 |
| Ex. (2) | P-2 | 5.0 | 11.9 | 2500.0 | 20.9 | 117.5 | 0.65 | 0.33 |
| Ex. (3) | P-3 | 4.9 | 12.0 | 2500.0 | 20.9 | 120.0 | 0.62 | 0.33 |
| Ex. (4) | P-7 | 4.9 | 12.1 | 2500.0 | 20.6 | 116.8 | 0.64 | 0.33 |
| Ex. (5) | P-9 | 4.9 | 12.3 | 2500.0 | 20.3 | 115.0 | 0.65 | 0.34 |
| Ex. (6) | P-10 | 5.0 | 12.2 | 2500.0 | 20.4 | 116.9 | 0.62 | 0.34 |
| Ex. (7) | P-11 | 5.0 | 12.3 | 2500.0 | 20.3 | 118.1 | 0.60 | 0.33 |
| Ex. (8) | P-12 | 4.9 | 12.2 | 2500.0 | 20.5 | 116.6 | 0.65 | 0.33 |

TABLE 4-continued

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Ex. (9) | P-21 | 5.2 | 12.6 | 2500.0 | 19.8 | 111.0 | 0.61 | 0.34 |
| Ex. (10) | P-22 | 5.2 | 12.6 | 2500.0 | 19.9 | 113.6 | 0.64 | 0.34 |
| Ex. (11) | P-24 | 5.2 | 13.0 | 2500.0 | 19.2 | 113.0 | 0.60 | 0.33 |
| Ex. (12) | P-25 | 4.9 | 12.2 | 2500.0 | 20.4 | 116.0 | 0.64 | 0.32 |
| Ex. (13) | P-29 | 5.2 | 13.2 | 2500.0 | 19.0 | 110.6 | 0.64 | 0.32 |
| Ex. (14) | P-30 | 5.2 | 13.5 | 2500.0 | 18.5 | 114.8 | 0.62 | 0.34 |
| Ex. (15) | P-32 | 5.1 | 13.4 | 2500.0 | 18.7 | 113.1 | 0.62 | 0.33 |
| Ex. (16) | P-33 | 5.1 | 13.3 | 2500.0 | 18.7 | 114.6 | 0.61 | 0.35 |
| Ex. (17) | P-35 | 5.2 | 13.2 | 2500.0 | 18.9 | 114.1 | 0.63 | 0.35 |
| Ex. (18) | P-37 | 5.2 | 13.2 | 2500.0 | 19.0 | 112.2 | 0.62 | 0.31 |
| Ex. (19) | P-40 | 5.1 | 13.2 | 2500.0 | 18.9 | 110.0 | 0.62 | 0.31 |
| Ex. (20) | P-44 | 5.2 | 13.4 | 2500.0 | 18.7 | 110.1 | 0.61 | 0.34 |
| Ex. (21) | P-45 | 5.3 | 13.9 | 2500.0 | 18.0 | 108.8 | 0.64 | 0.34 |
| Ex. (22) | P-56 | 5.2 | 14.3 | 2500.0 | 17.5 | 107.1 | 0.64 | 0.31 |
| Ex. (23) | P-57 | 4.9 | 12.0 | 2500.0 | 20.8 | 118.9 | 0.64 | 0.35 |
| Ex. (24) | P-59 | 5.0 | 12.5 | 2500.0 | 20.0 | 115.8 | 0.60 | 0.32 |
| Ex. (25) | P-61 | 5.1 | 12.8 | 2500.0 | 19.5 | 107.0 | 0.63 | 0.34 |
| Ex. (26) | P-65 | 5.0 | 12.4 | 2500.0 | 20.1 | 118.2 | 0.64 | 0.33 |
| Ex. (27) | P-67 | 5.2 | 14.1 | 2500.0 | 17.7 | 109.4 | 0.61 | 0.31 |
| Ex. (28) | P-69 | 4.9 | 12.3 | 2500.0 | 20.3 | 115.7 | 0.60 | 0.34 |
| Ex. (29) | P-78 | 4.9 | 12.1 | 2500.0 | 20.7 | 115.9 | 0.65 | 0.32 |
| Ex. (30) | P-86 | 4.9 | 12.2 | 2500.0 | 20.5 | 116.6 | 0.62 | 0.32 |
| Ex. (31) | P-93 | 5.0 | 12.3 | 2500.0 | 20.4 | 116.5 | 0.63 | 0.32 |

From Table 4, it can be seen that the driving voltage of the organic electroluminescent element can be lowered and the luminous efficiency and lifetime are significantly improved in case where the red organic electroluminescent element was manufactured by employing material for the organic electroluminescent element of the present invention, compared with Comparative Examples not forming an emission-auxiliary layer or employing one of Comparative Compounds A to C.

The results of Comparative Examples 2 to 4 employing one of Comparative Compounds A to C as material of the emission-auxiliary layer were superior to Comparative Example 1 not forming an emission-auxiliary layer, and the results of Examples 1 to 31 employing the compounds of the present invention were the best, wherein the compound of the present invention is similar in structure to Comparative Compounds A to C but different in type and the bonding position of substituents.

Comparing the results of using the comparative compounds A, B and the compounds of the present invention, it can be seen that different element results are obtained. This is because if the position of the substituent is changed even if the core is similar, the energy level (e.g., HOMO, LUMO, T1) value is changed. As the physical properties of the compound change, it acts as a major factor in improving performance during element deposition process. As a result, significantly different results were obtained.

The difference between the comparative compound C and the compound of the present invention is the presence of L$^2$. The element results of the case using the compound of the present invention as material of an emission-auxiliary layer, wherein the compound has an arylene group or a heteroarylene group as a linker, are superior to those of Comparative Compound C having L$^2$ as a single bond. This means that even if the compound is similar, the energy level of the compound varies depending on the presence or absence of L$^2$, and thus results of element are also changed.

In conclusion, it can be seen that the results of the element employing the compound of the present invention, in which L$^2$ is necessarily present and the amine group and L$^2$ are bonded to a specific position of two dibenzothiophen or dibenzofuran, are is superior to existing similar compounds.

Although exemplary embodiments of the present invention have been described for illustrative purposes, those skilled in the art will appreciate that various modifications can be made without departing from the essential characteristics of the present invention. Therefore, the embodiments disclosed in the present invention are intended to illustrate the present invention, and the scope of the present invention is not limited by the embodiments. The scope of the present invention shall be construed on the basis of the accompanying claims, and it shall be construed that all of the technical ideas included within the scope equivalent to the claims belong to the present invention.

The invention claimed is:

1. A compound of Formula 1:

[Formula 1]

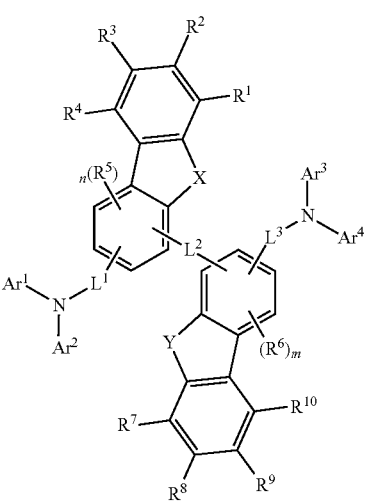

wherein:

X and Y are each independently O or S, $L^1$ and $L^3$ are each independently selected from the group consisting of a single bond, a $C_6$-$C_{60}$ arylene group, a fluorenylene group, a $C_2$-$C_{60}$ heterocyclic group containing at least one heteroatom selected from the group consisting of O, N, S, Si, and P, and a fused ring group formed by a $C_3$-$C_{60}$ aliphatic ring with a $C_6$-$C_{60}$ aromatic ring, $L^2$ is selected from the group consisting of a $C_6$-$C_{60}$ arylene group, a fluorenylene group, a $C_2$-$C_{60}$ heterocyclic group containing at least one heteroatom selected from the group consisting of O, N, S, Si, and P, and a fused ring group formed by a $C_3$-$C_{60}$ aliphatic ring with a $C_6$-$C_{60}$ aromatic ring, $Ar^1$ to $Ar^4$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group formed by a $C_3$-$C_{60}$ aliphatic ring with a $C_6$-$C_{60}$ aromatic ring, a $C_6$-$C_{30}$ aryloxy group and -L'-N($R_a$)($R_b$), $R^1$ to $R^{10}$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a fused ring group formed by a $C_3$-$C_{60}$ aliphatic ring with a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and adjacent groups may be optionally linked to each other to form a ring, m and n are each an integer of 0 to 2, L' is selected from the group consisting of a single bond, a $C_6$-$C_{60}$ arylene group, a fluorenylene group, and a $C_2$-$C_{60}$ heterocyclic group containing at least one heteroatom selected from the group consisting of O, N, S, Si, and P, and a fused ring group formed by a $C_3$-$C_{60}$ aliphatic ring with a $C_6$-$C_{60}$ aromatic ring, $R_a$ and $R_b$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, and a fused ring group formed by a $C_3$-$C_{60}$ aliphatic ring with a $C_6$-$C_{60}$ aromatic ring, and the aryl group, the arylene group, the fluorenyl group, the fluorenylene group, the heterocyclic group, the fused ring group, the alkyl group, the alkenyl group, the alkynyl group, the alkoxyl group, the aryloxyl group, and the ring formed by adjacent groups may be each optionally substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, a $C_8$-$C_{20}$ arylalkenyl group and a combination thereof, with a proviso that the arylene group of $L^2$ may be optionally substituted with one or more substituents selected from the group consisting of deuterium, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, S, Si, and P, a $C_3$-$C_{20}$ cycloalkyl group, a $C_7$-$C_{20}$ arylalkyl group, a $C_8$-$C_{20}$ arylalkenyl group and a combination thereof.

2. The compound of claim 1, wherein Formula 1 is represented by one of Formula 2 to Formula 10:

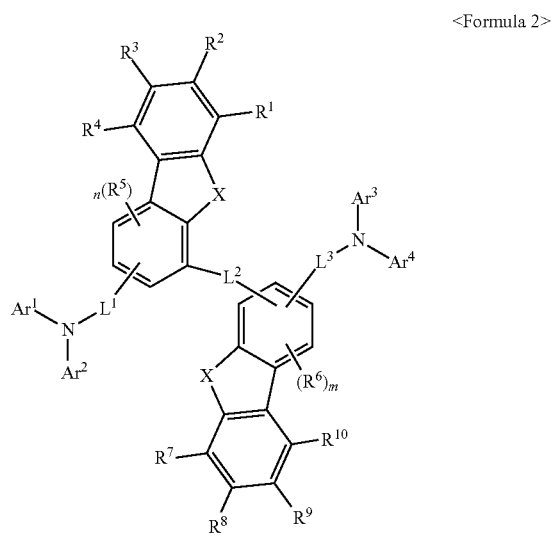

<Formula 2>

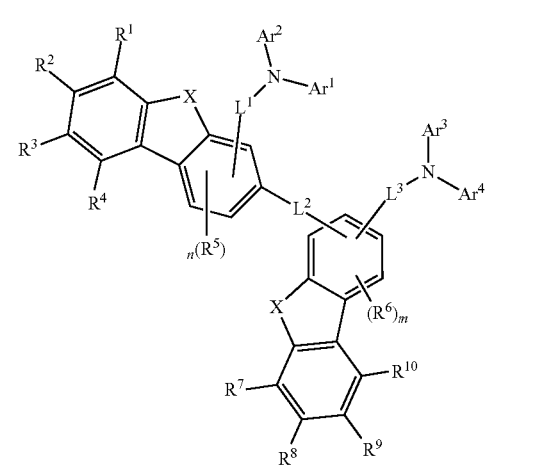

<Formula 3>

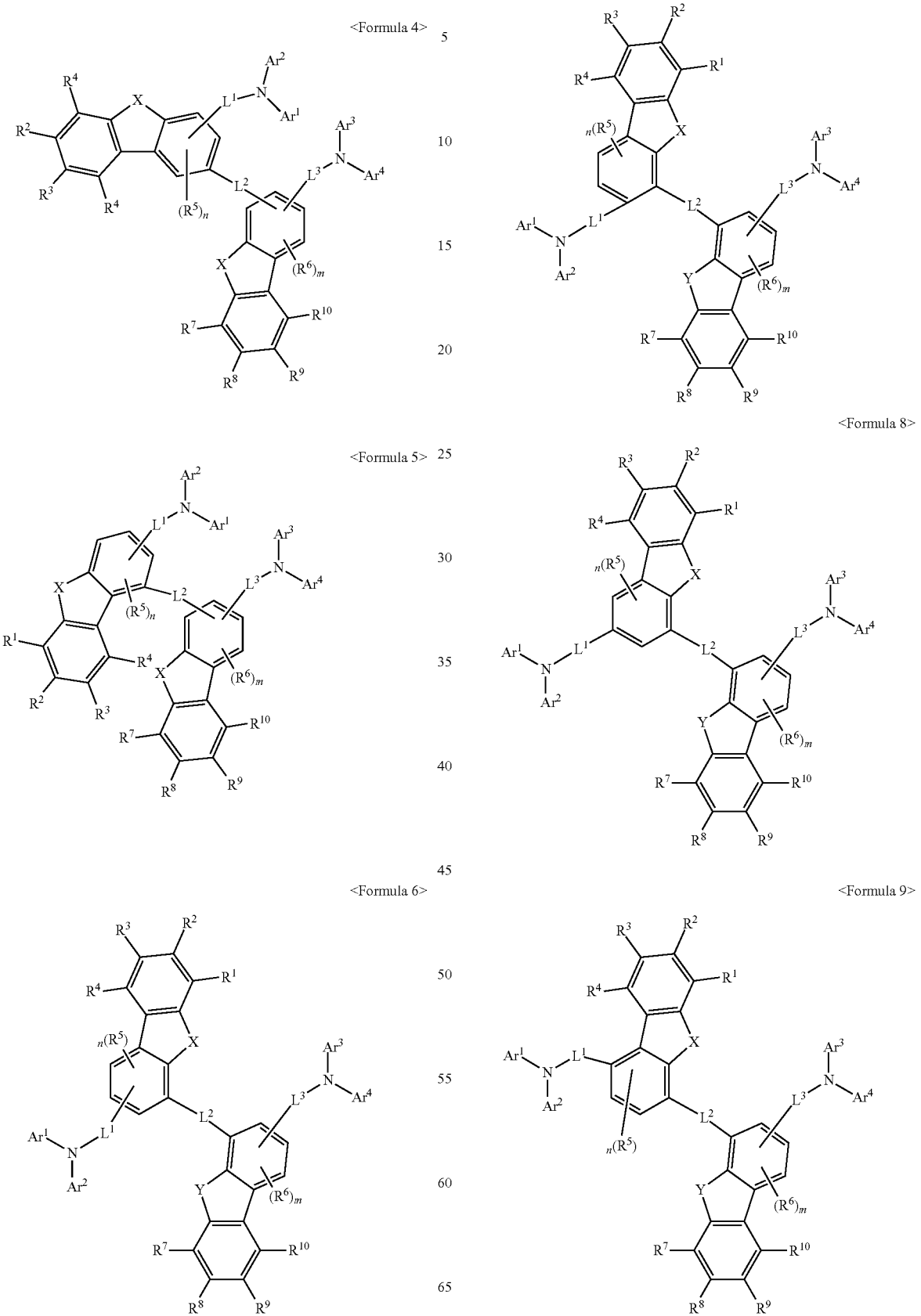

<Formula 10>
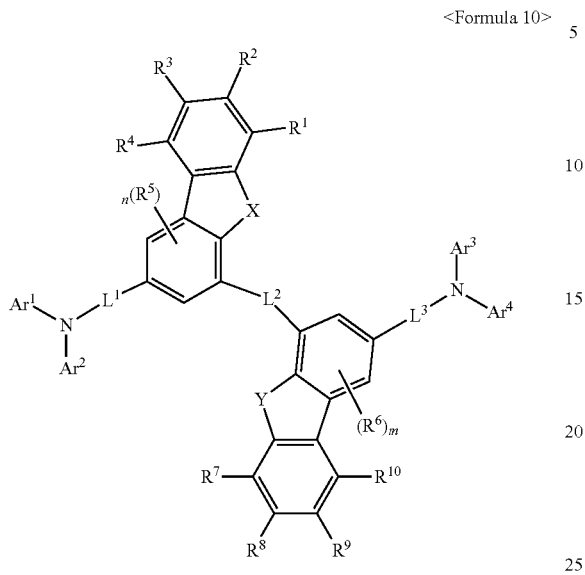
wherein X, Y, $L^1$ to $L^3$, $Ar^1$ to $Ar^4$, $R^1$ to $R^{10}$, m and n are the same as defined in claim 1.
3. The compound of claim 1, wherein $L^1$ or $L^3$ is represented by one of Formulas A-1 to A-13:
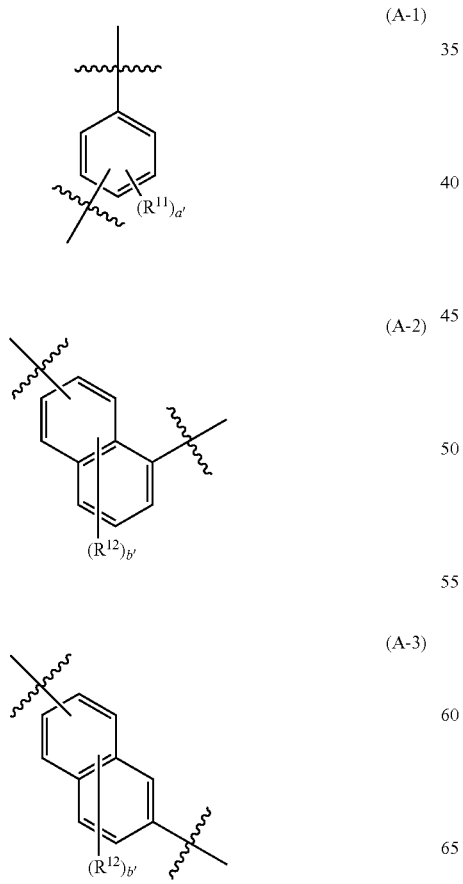
(A-1)
(A-2)
(A-3)
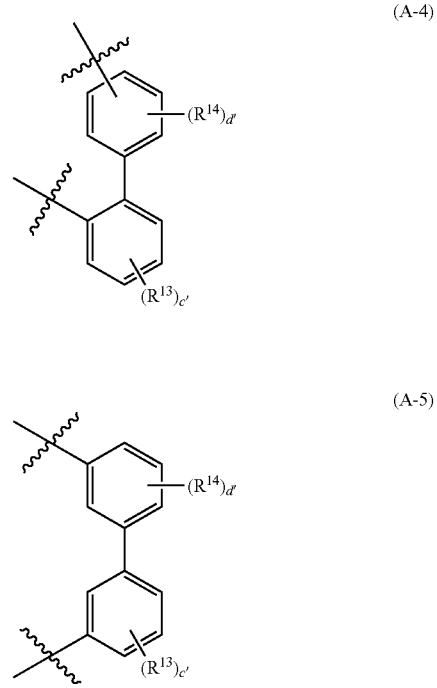
(A-4)
(A-5)
(A-6)
(A-7)

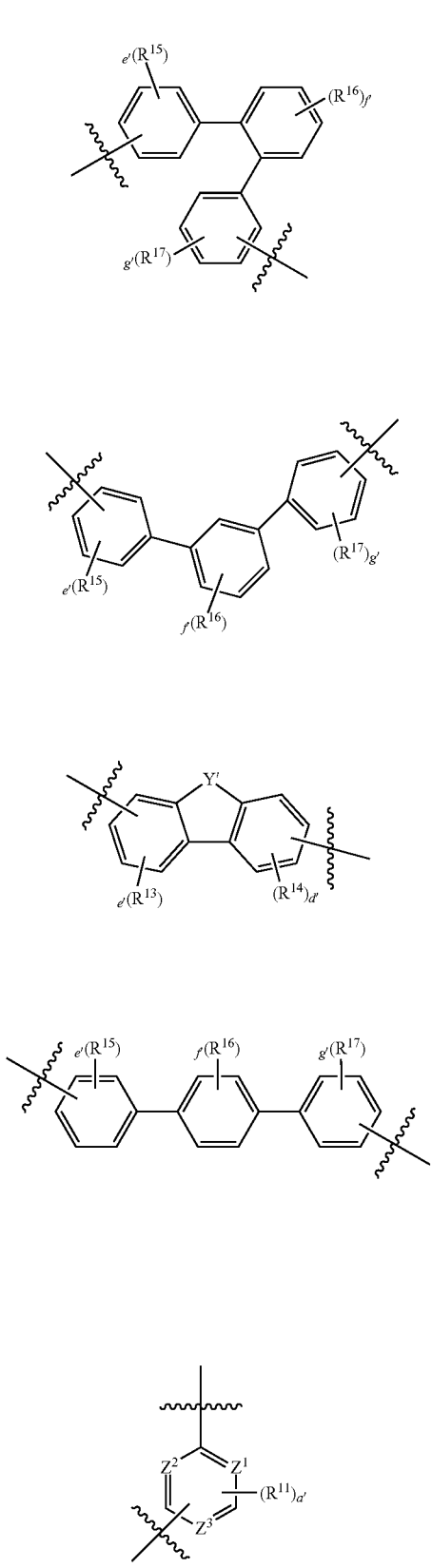

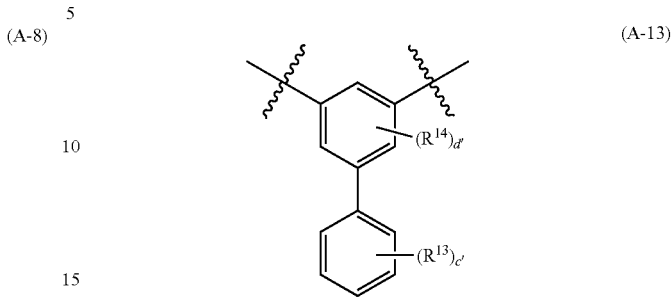

wherein, a', c', d', e', f' and g' are each an integer of 0 to 4, b' is an integer of 0 to 6, $R^{11}$ to $R^{17}$ are each independently selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, and adjacent groups may be optionally linked to each other to form a ring, Y' is N(R'), O, S or C(R')(R"), $Z^1$ to $Z^3$ are each independently C, C(R') or N, and at least one of them is N, R' and R" are each independently selected from the group consisting of hydrogen, deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, and R' and R" may be optionally linked to each other to form a ring.

4. The compound of claim 1, wherein adjacent groups among $R^1$ to $R^{10}$ are linked to each other to form a $C_6$-$C_{20}$ aromatic ring or a $C_2$-$C_{20}$ heterocyclic ring.

5. The compound of claim 1, wherein the compound represented by Formula 1 is one of the following compounds:

139
140
P-1
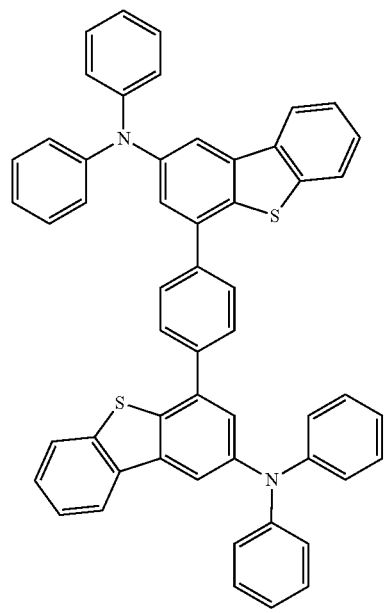
P-2
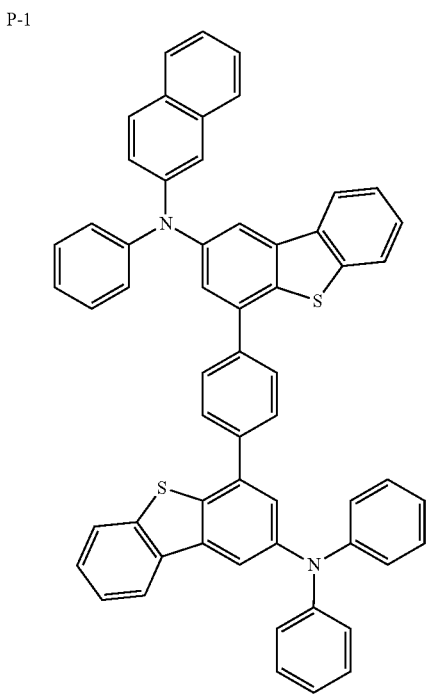
P-3
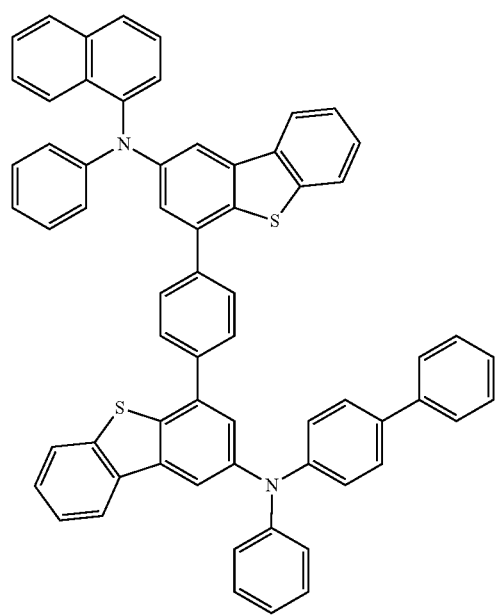
P-4
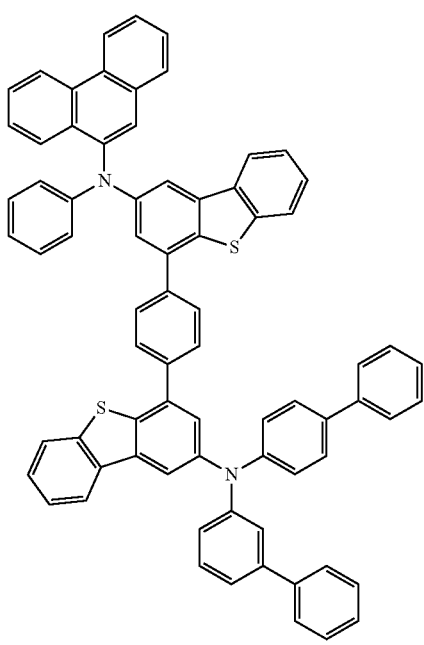

P-5
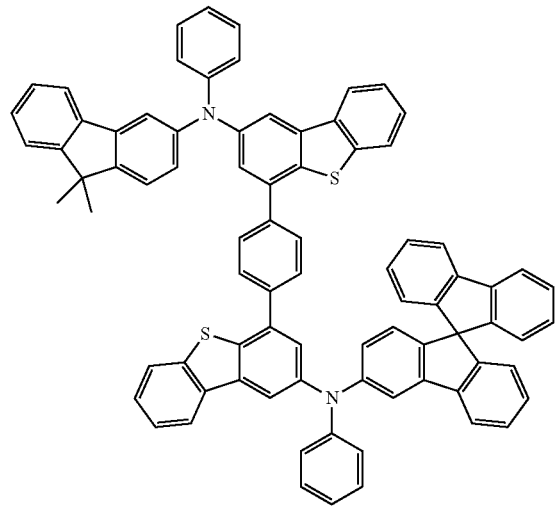
P-6
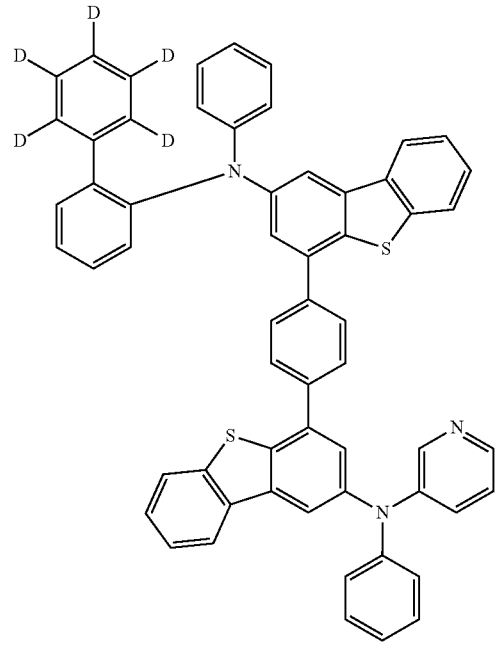
P-7
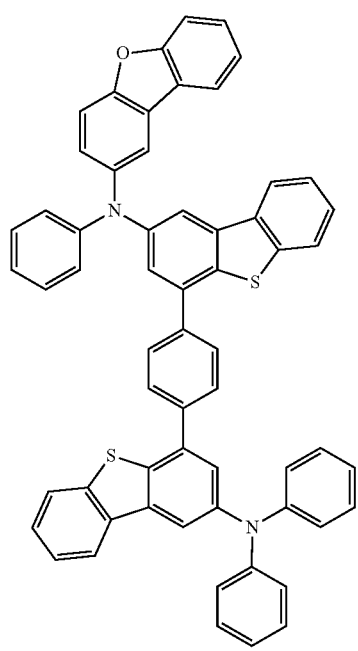
P-8
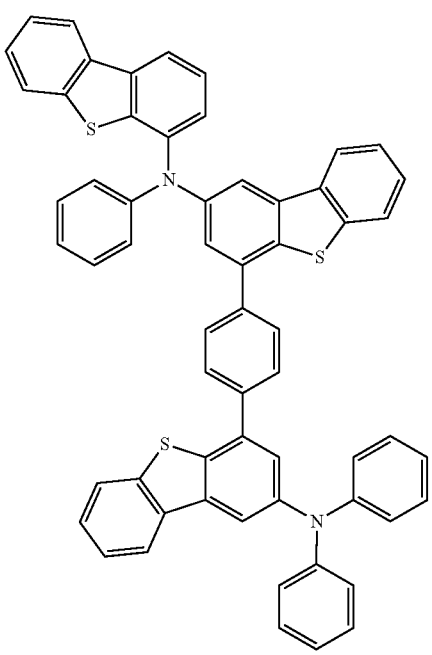

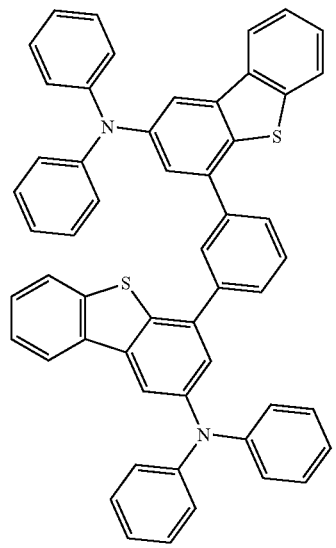
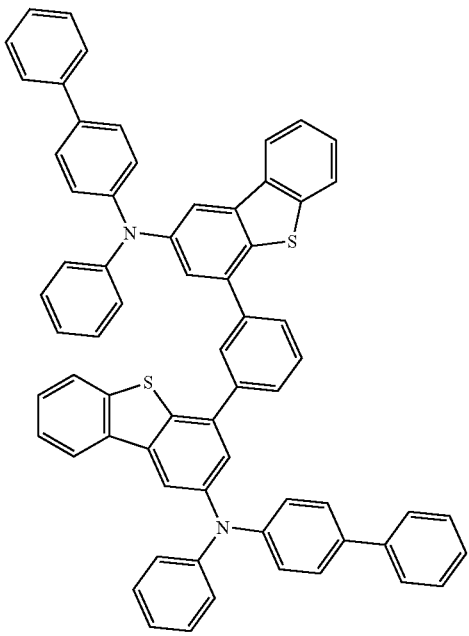
P-9
P-10
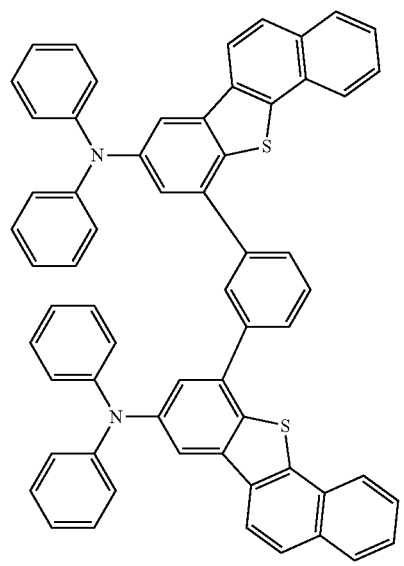
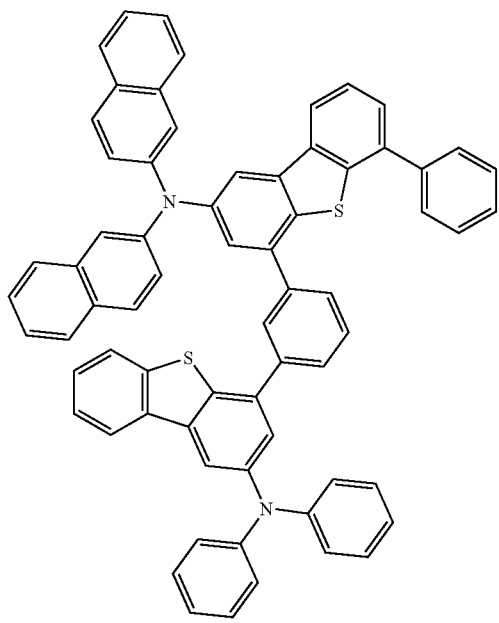
P-11
P-12

-continued
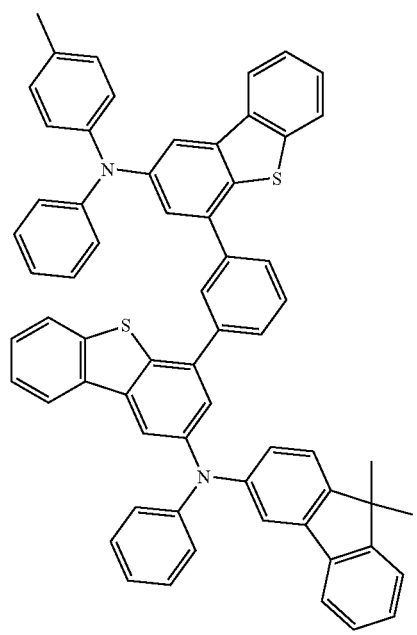
P-13
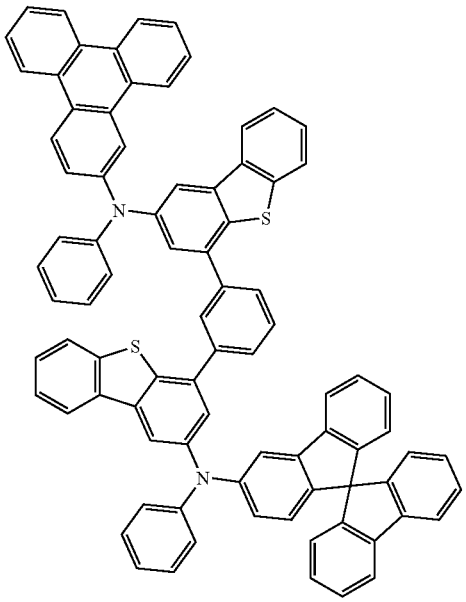
P-14
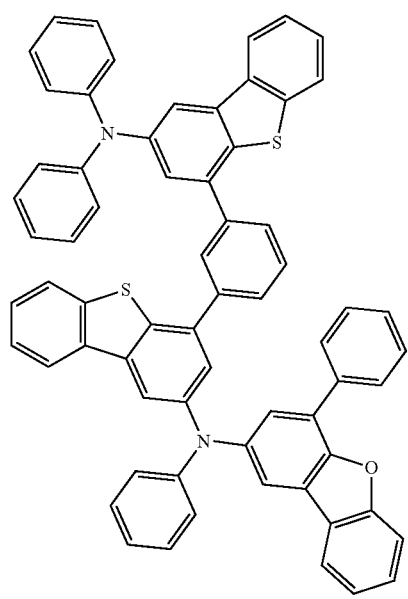
P-15
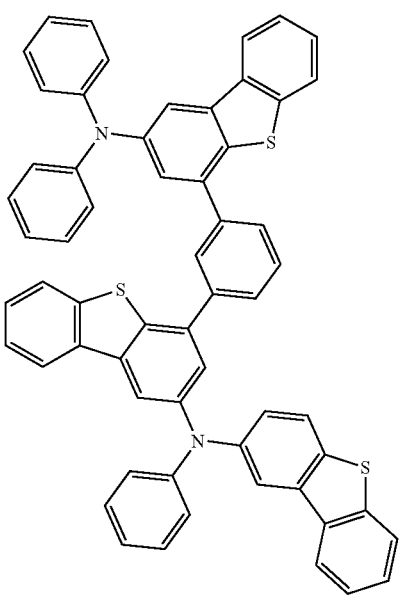
P-16

P-17
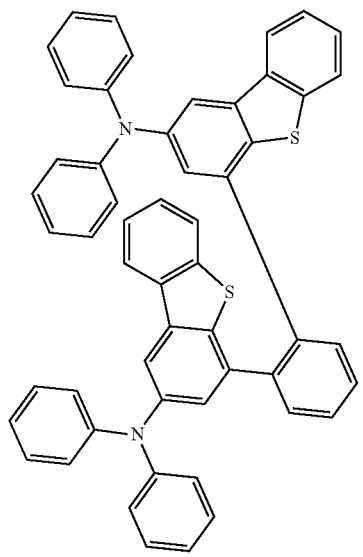
P-18
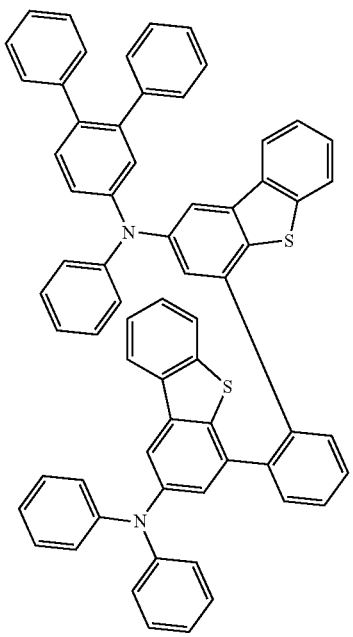
P-19
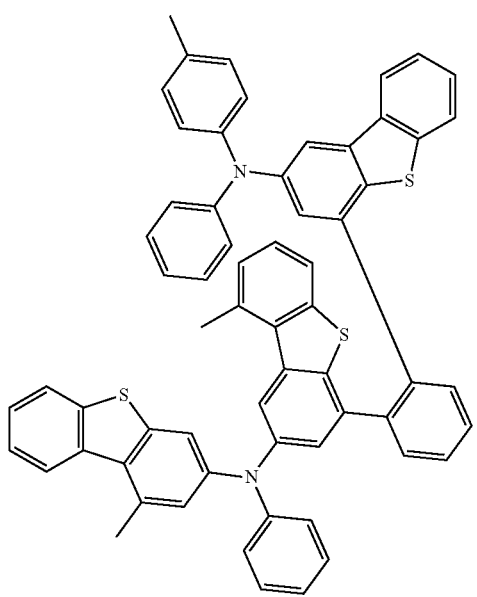
P-20
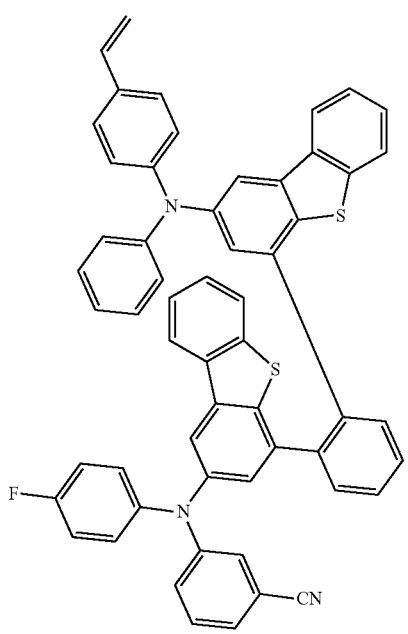

-continued
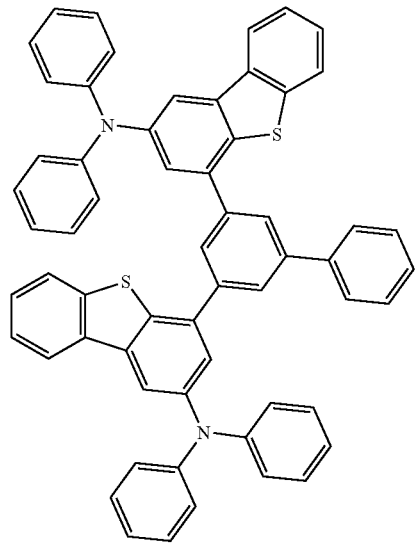
P-21
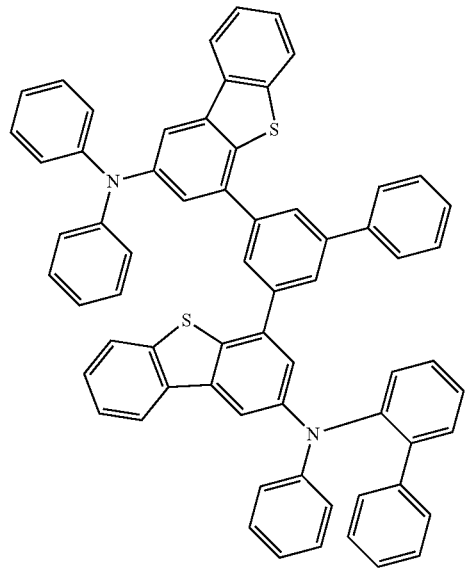
P-22
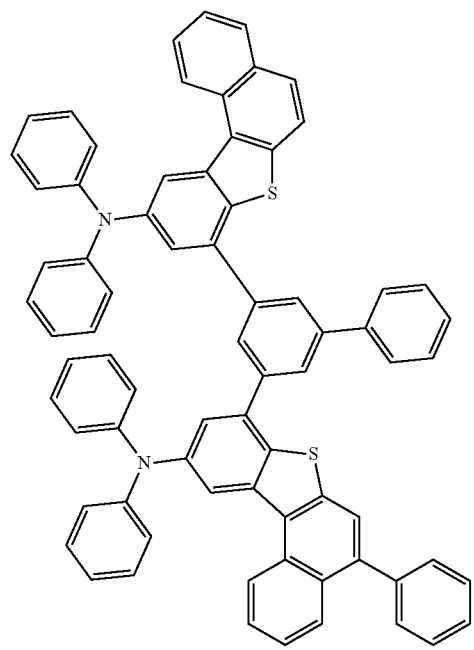
P-23
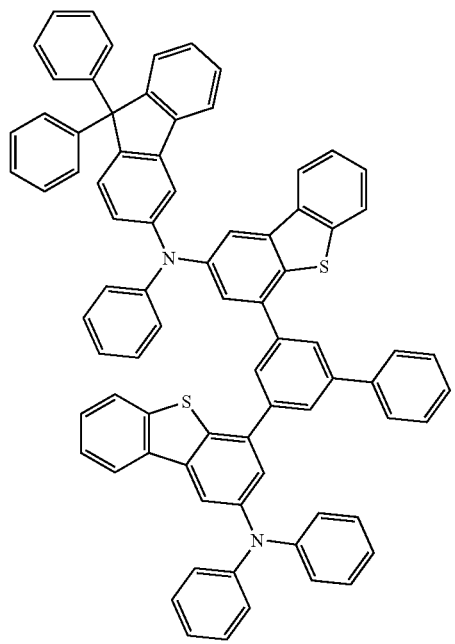
P-24

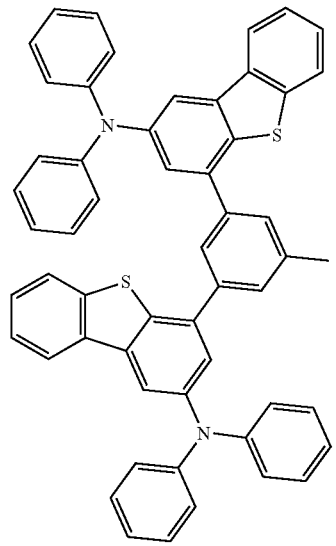
P-25
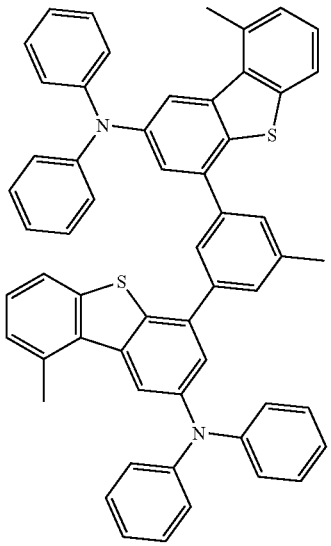
P-26
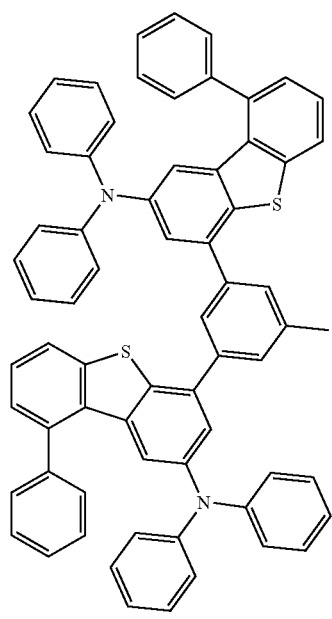
P-27
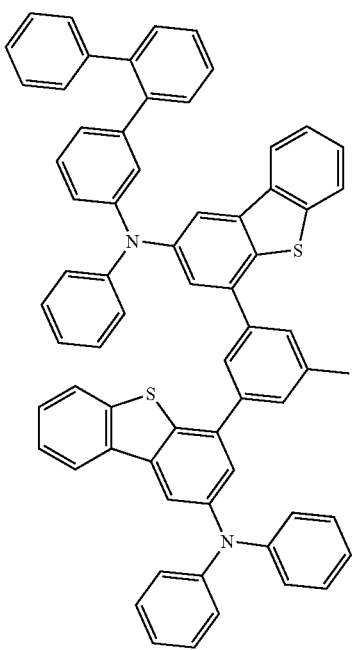
P-28

P-29
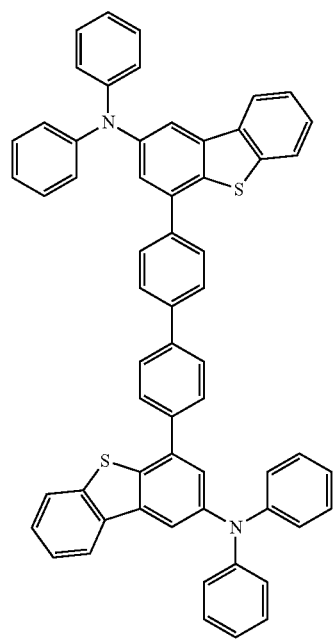
P-30
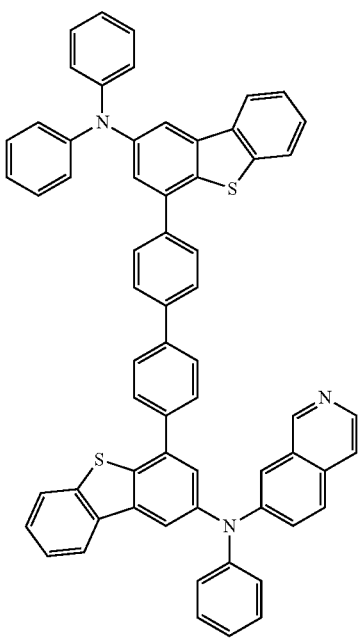
P-31
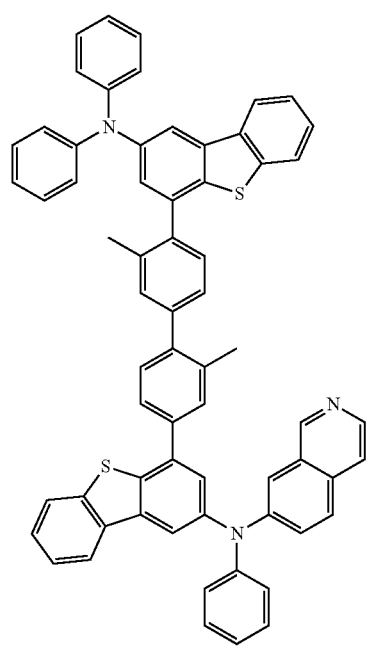
P-32
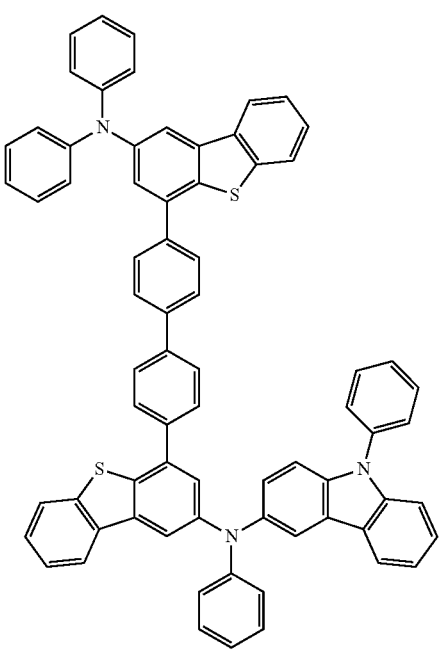

P-33
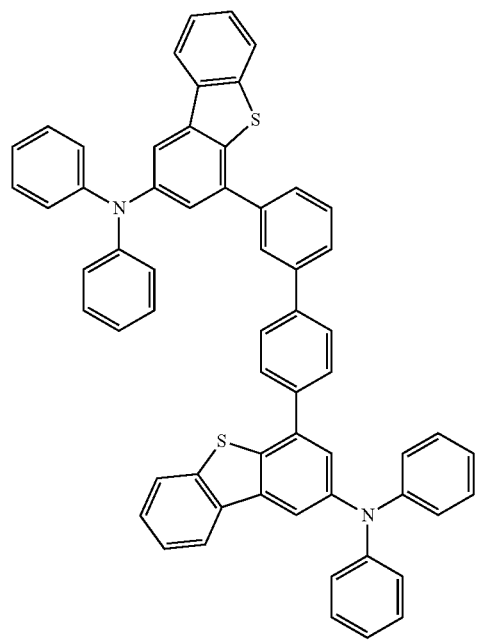
P-34
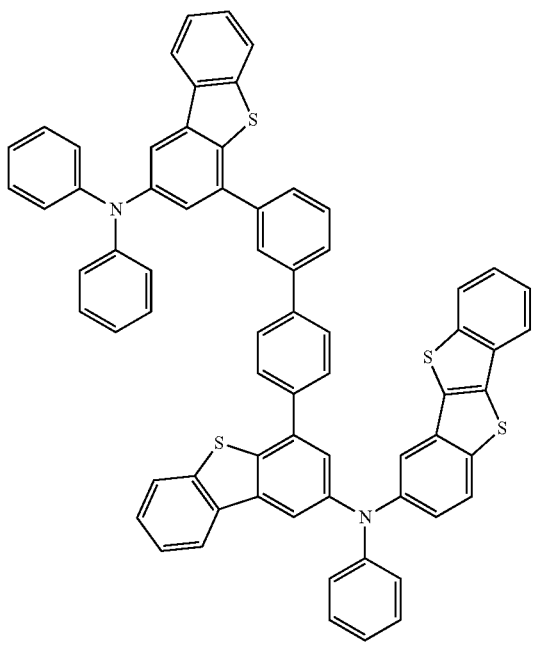
P-35
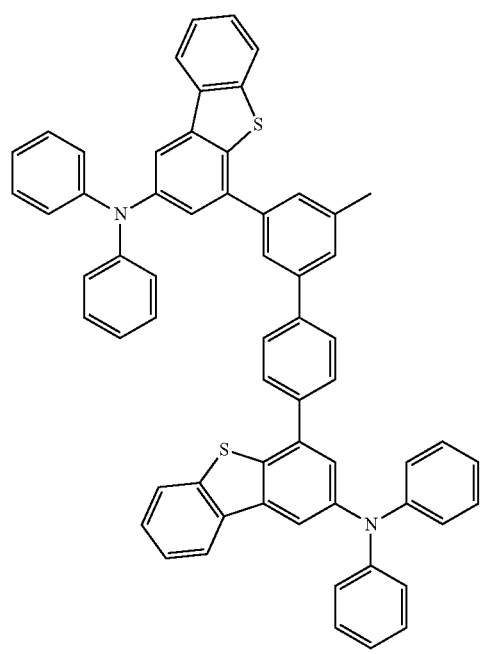
P-36
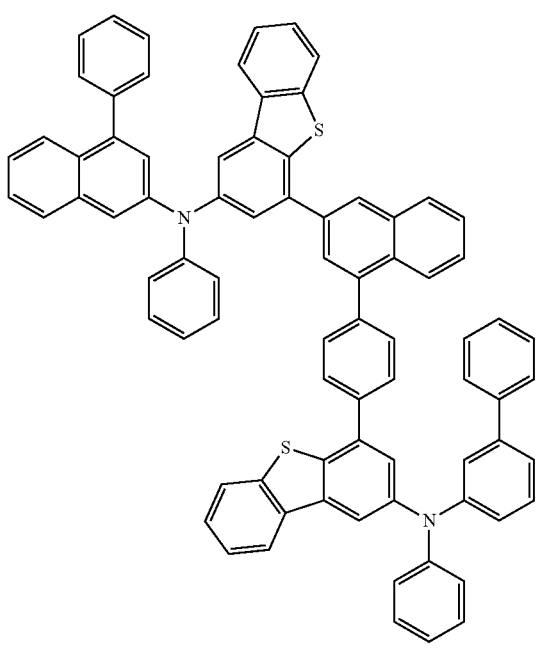

-continued
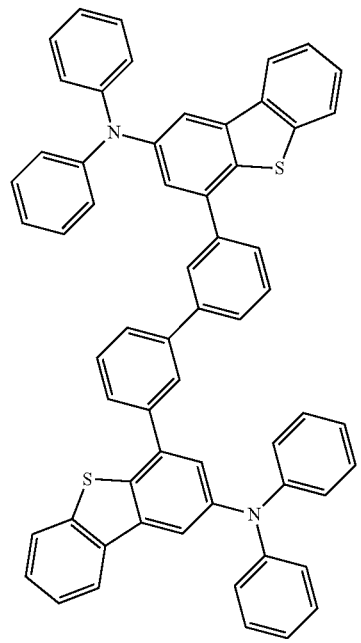
P-37
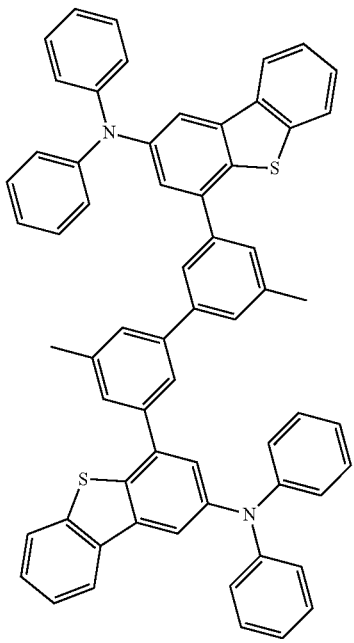
P-38
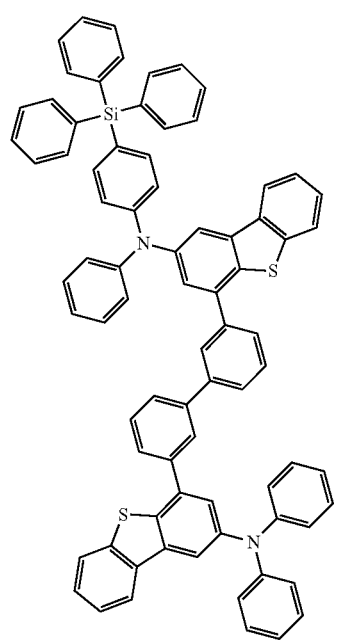
P-39
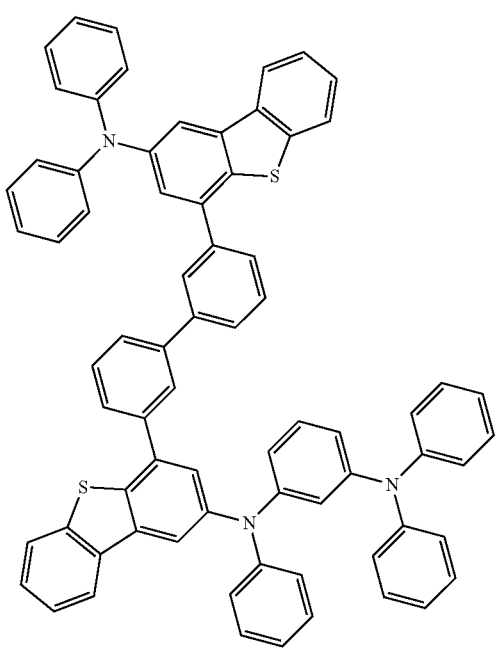
P-40

-continued
P-41
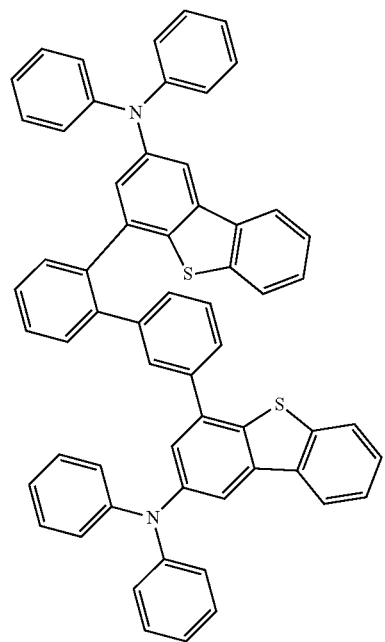
P-42
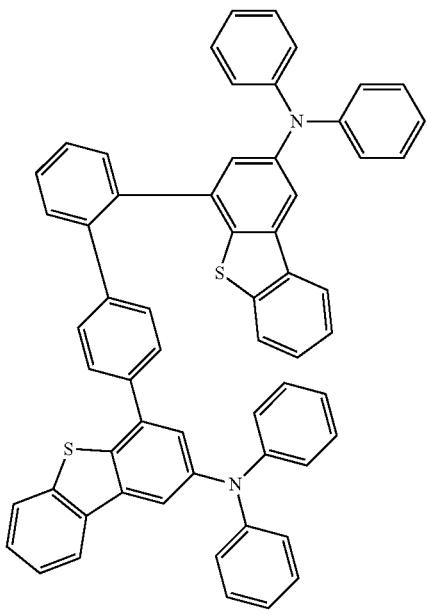
P-43
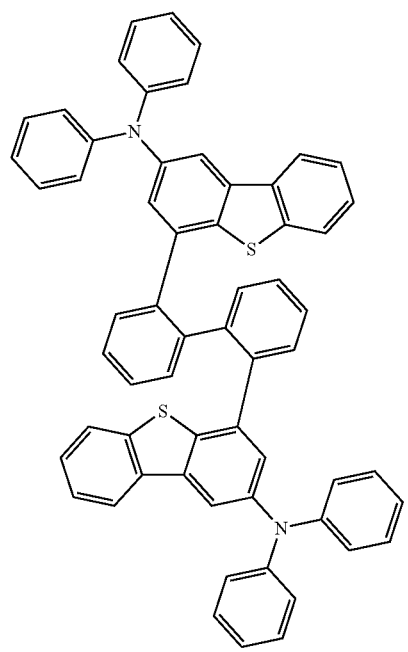
P-44
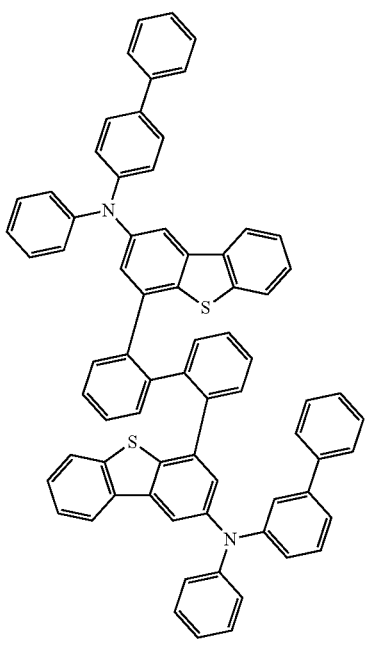

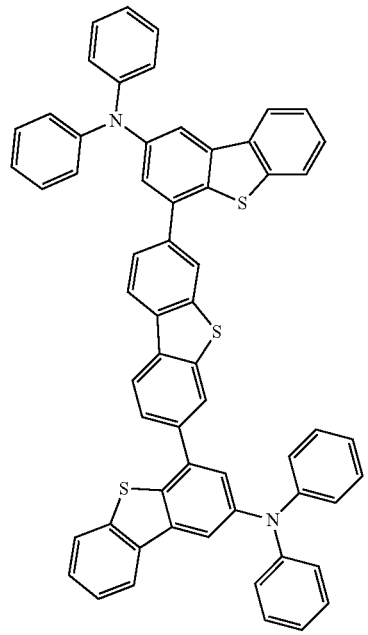 P-45
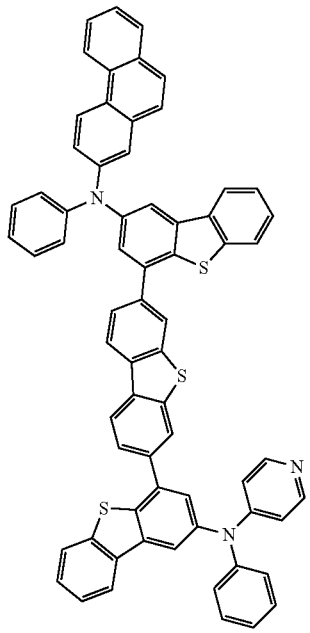 P-46
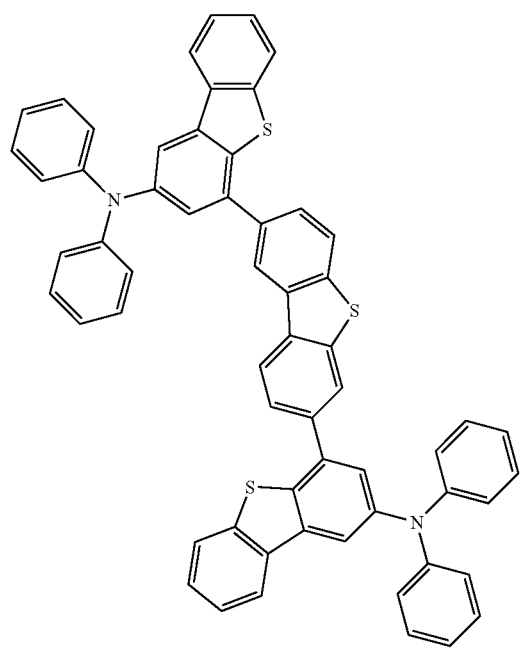 P-47
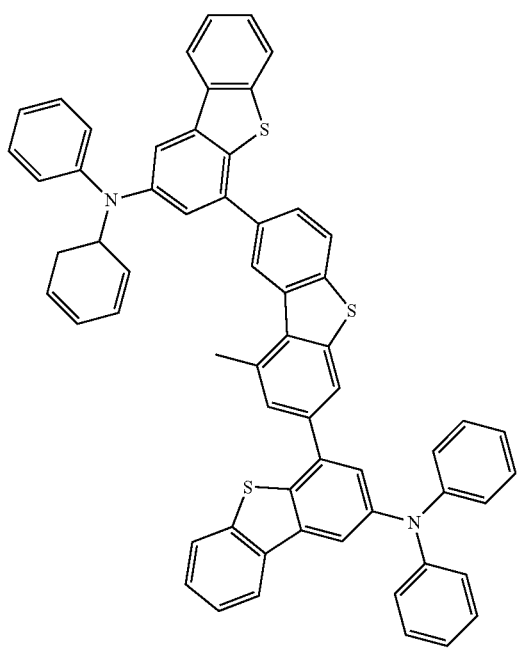 P-48

-continued
P-49
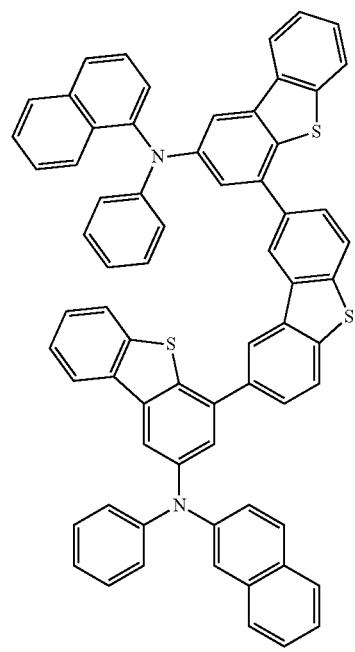
P-50
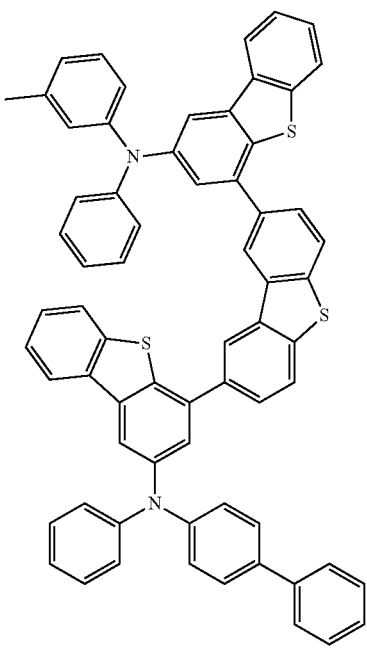
P-51
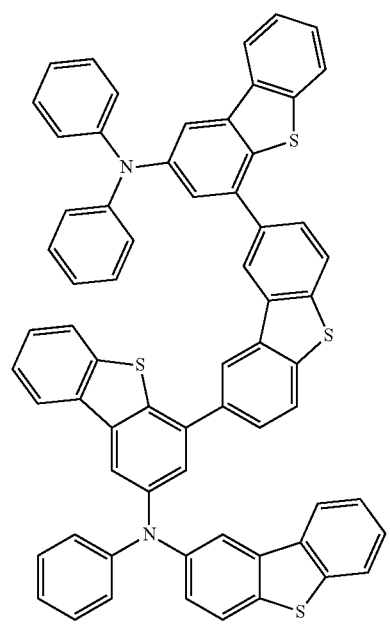
P-52
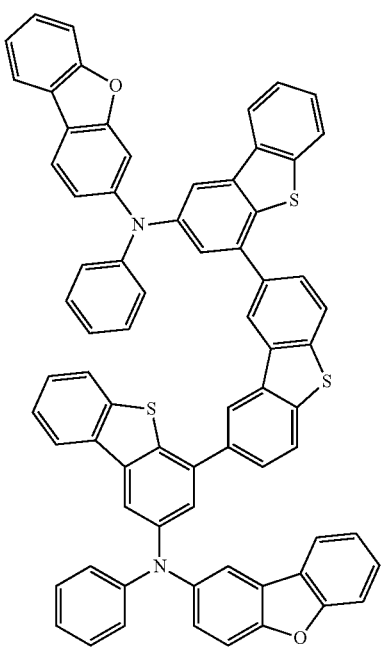

P-53
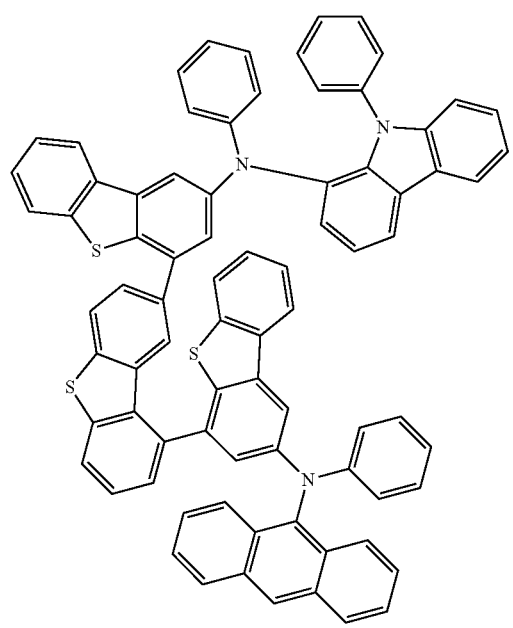
P-54
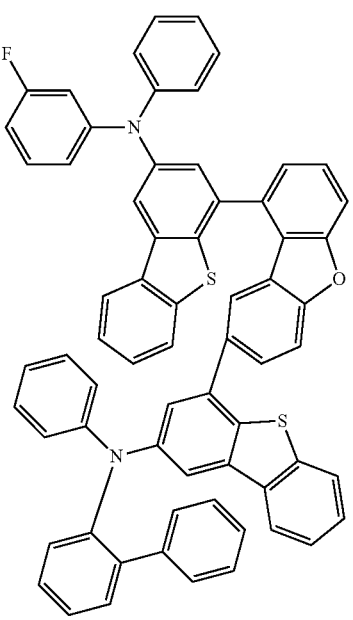
P-55
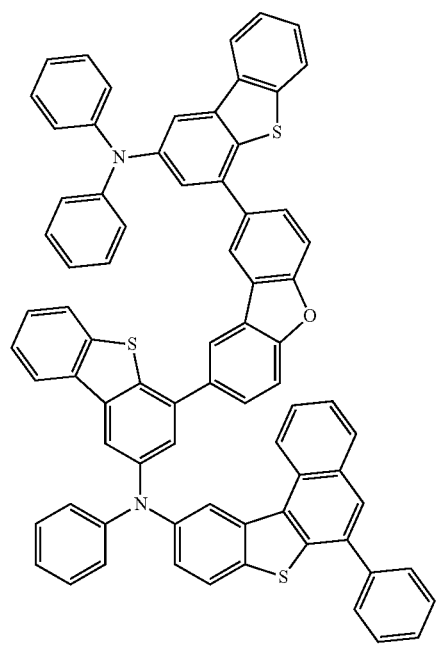
P-56
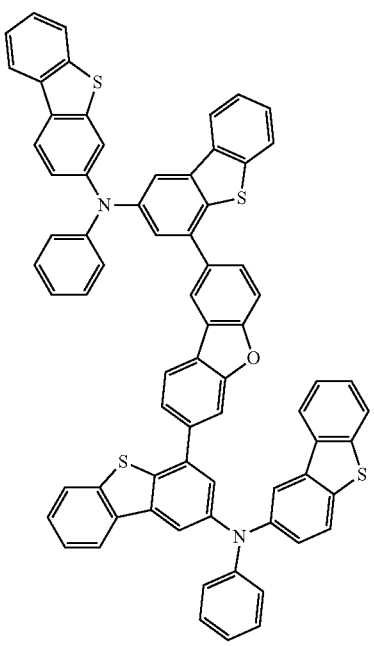

P-57
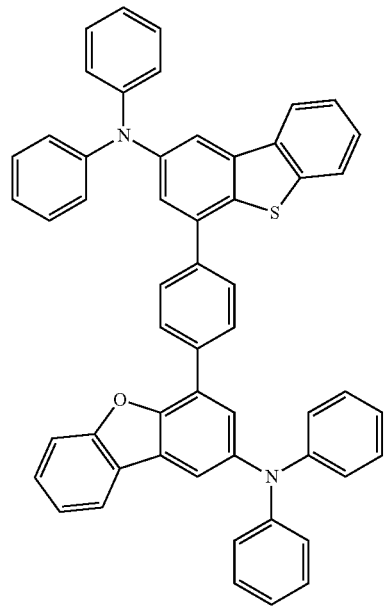
P-58
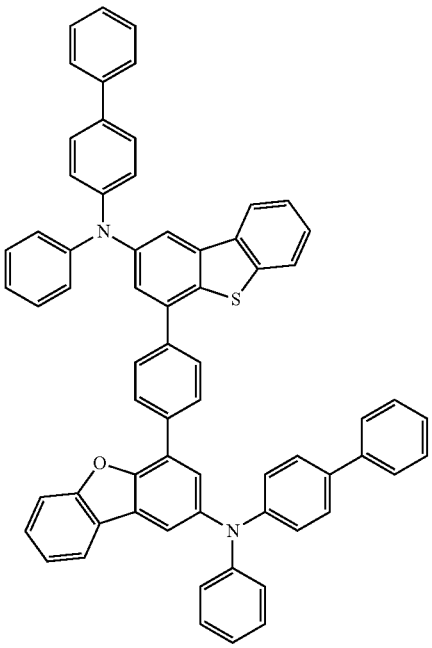
P-59
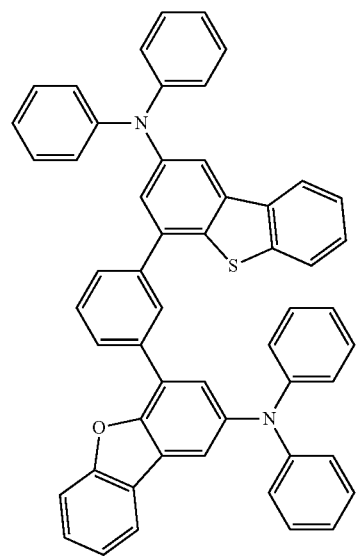
P-60
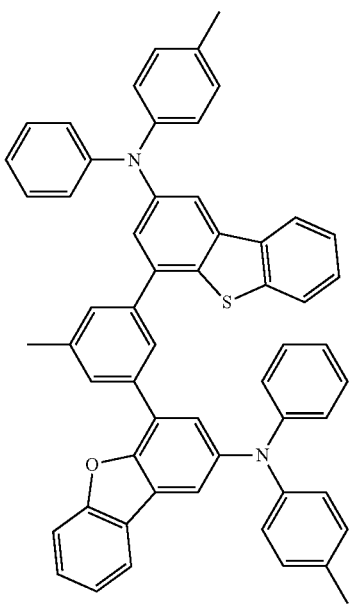

P-61
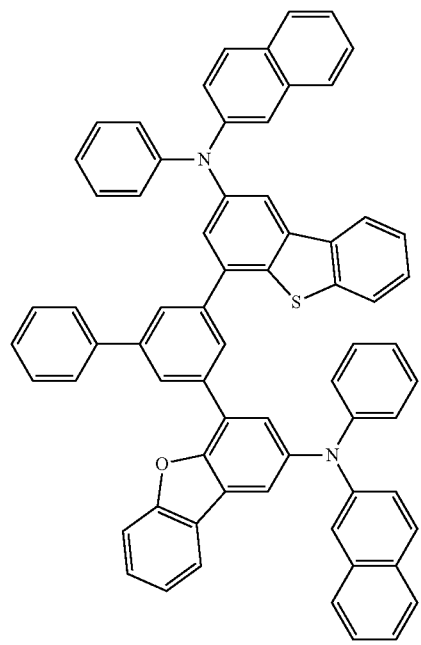
P-62
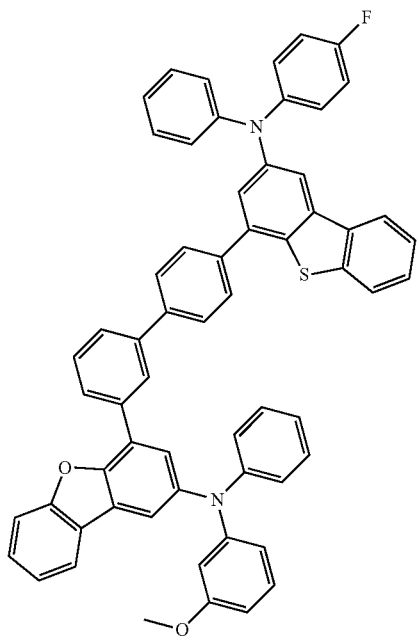
P-63
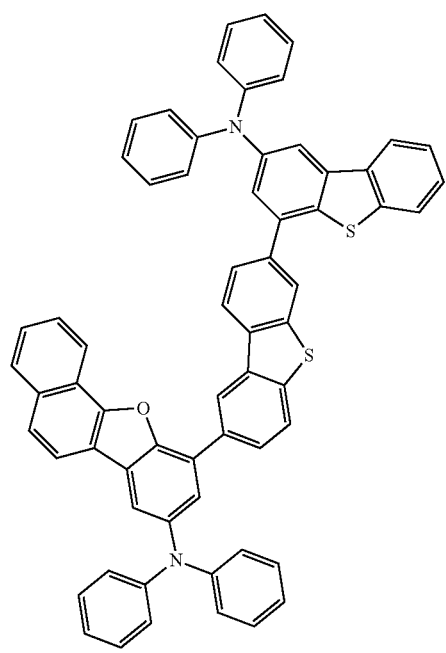
P-64
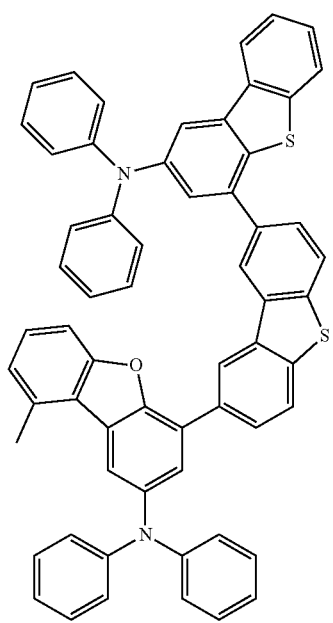

P-65
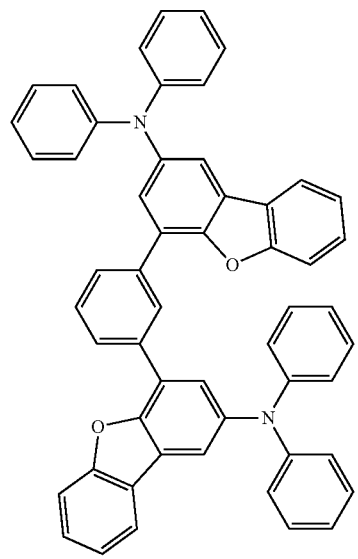
P-66
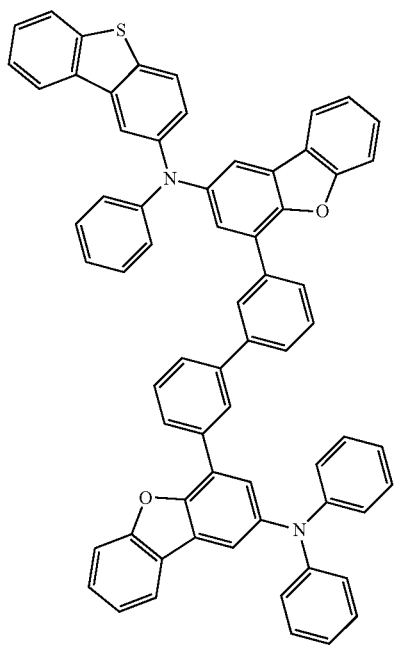
P-67
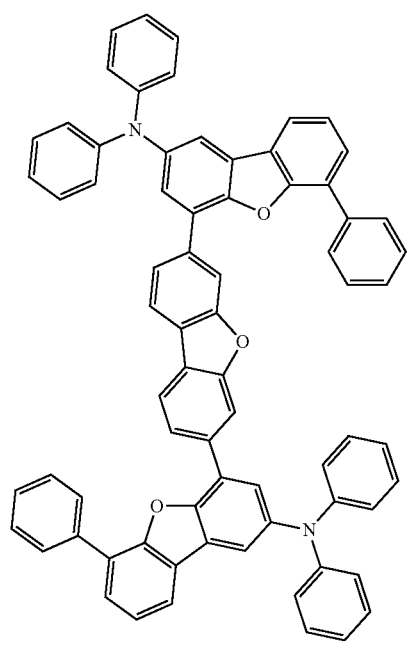
P-68
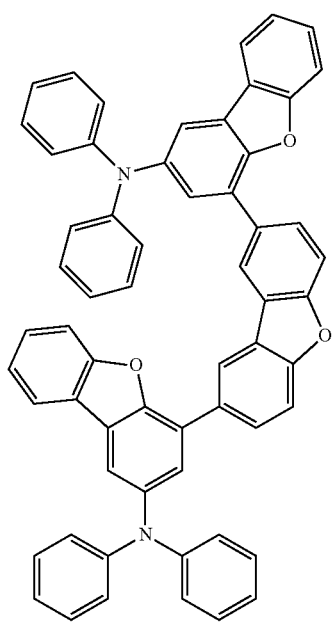

P-69
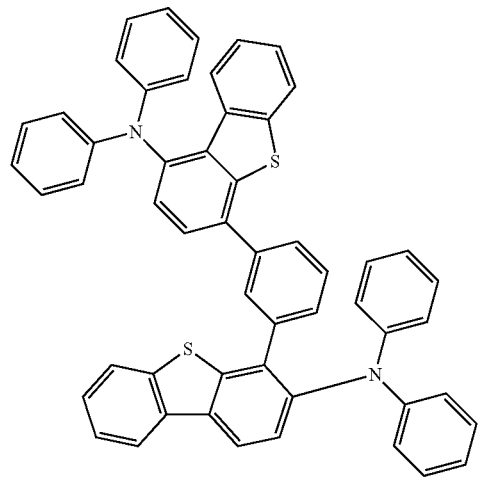
P-70
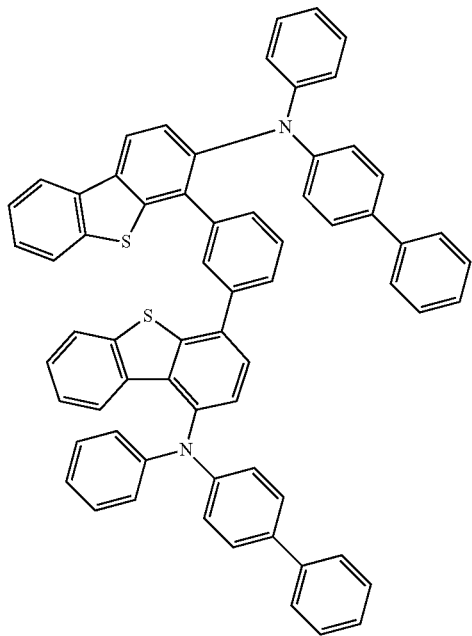
P-71
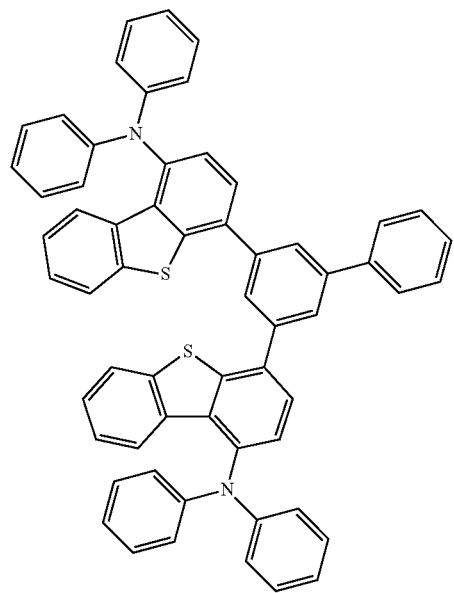
P-72
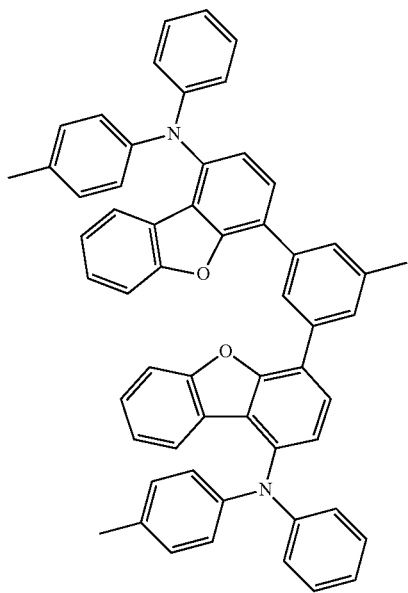

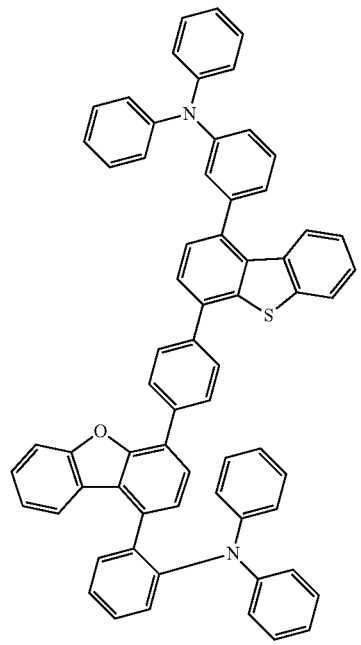
P-73
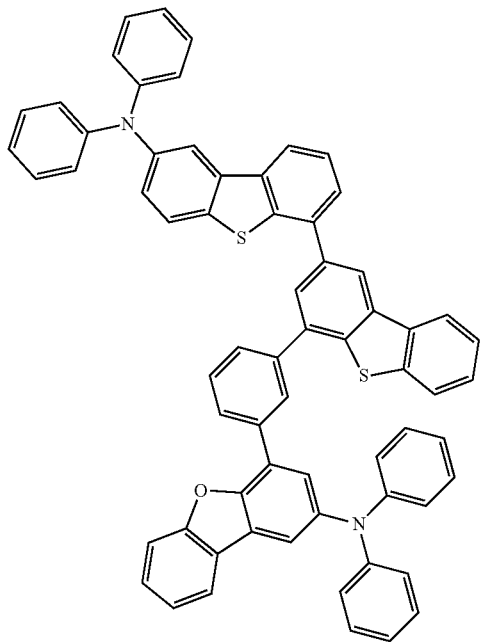
P-74
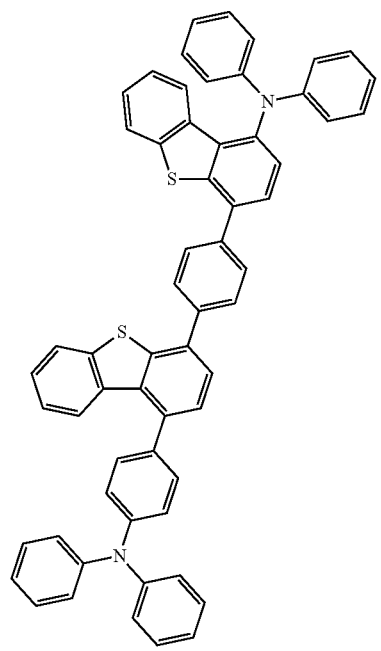
P-75
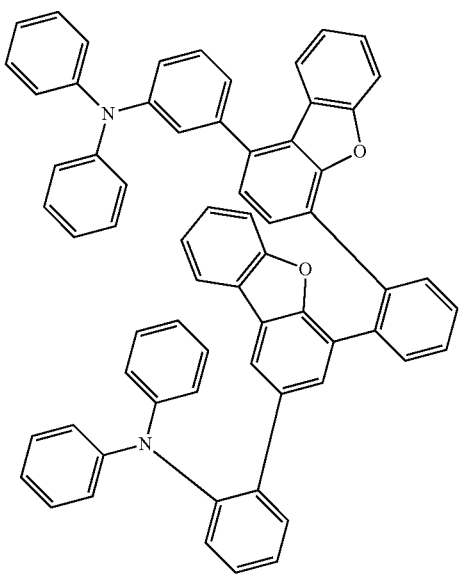
P-76

-continued
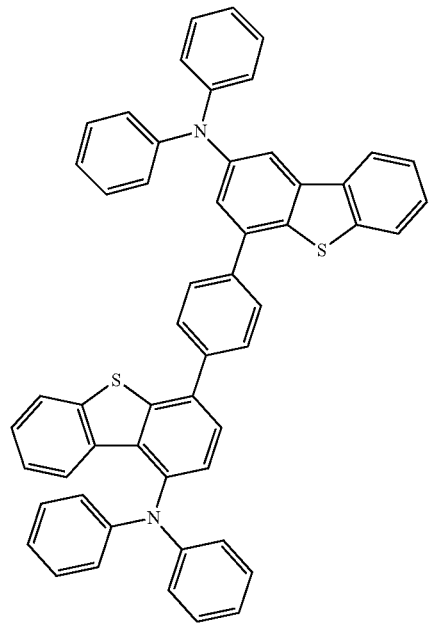
P-78
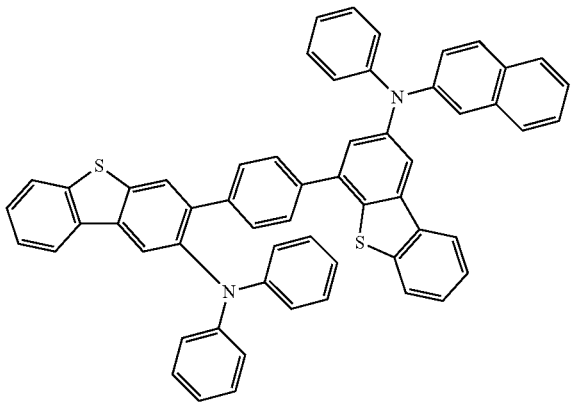
P-79
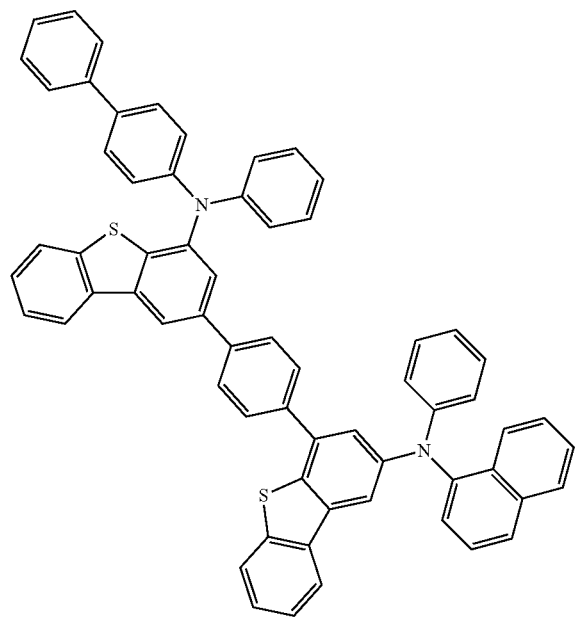
P-80

-continued
P-81
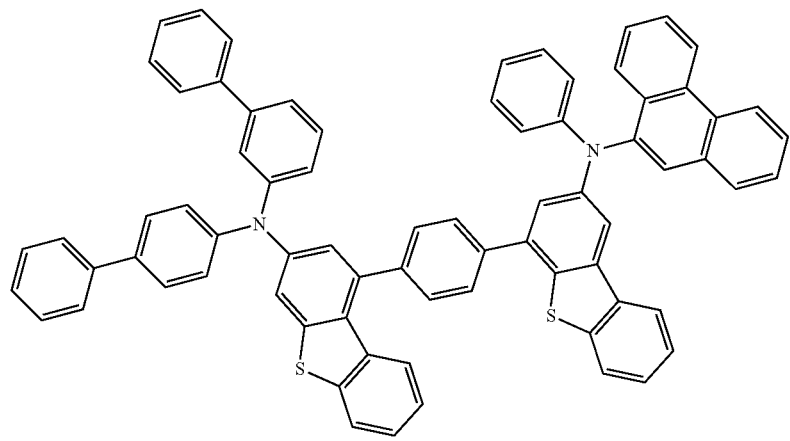
P-82
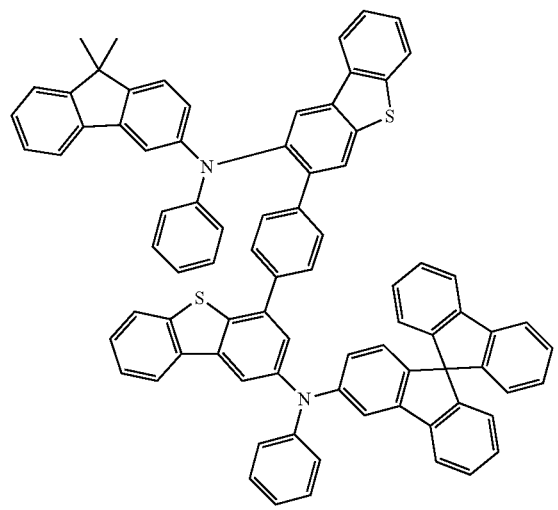
P-83
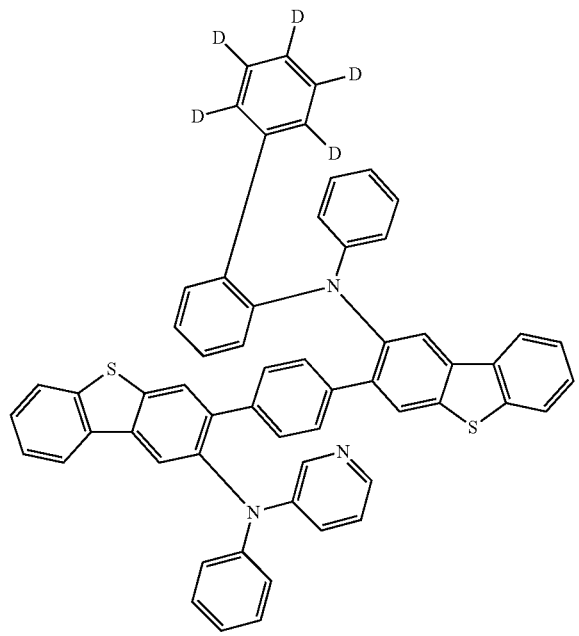
P-84
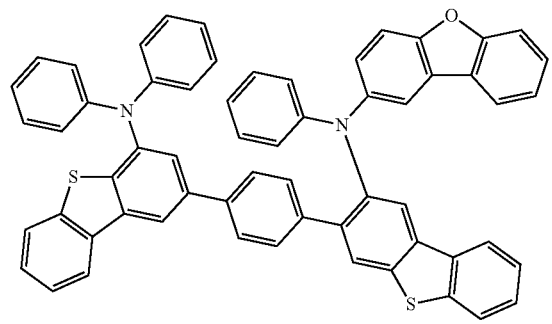
P-85
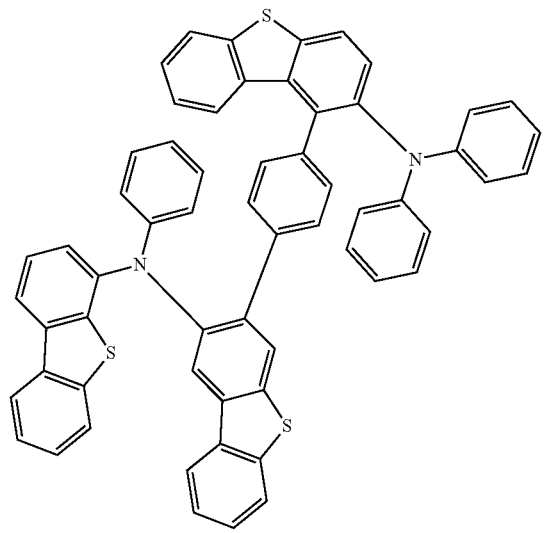

P-86
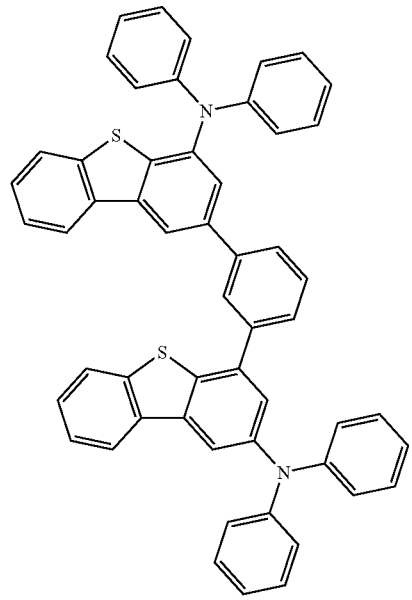
P-87
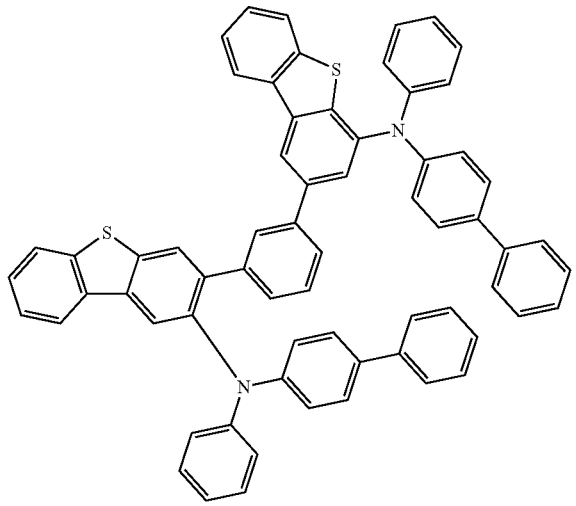
P-88
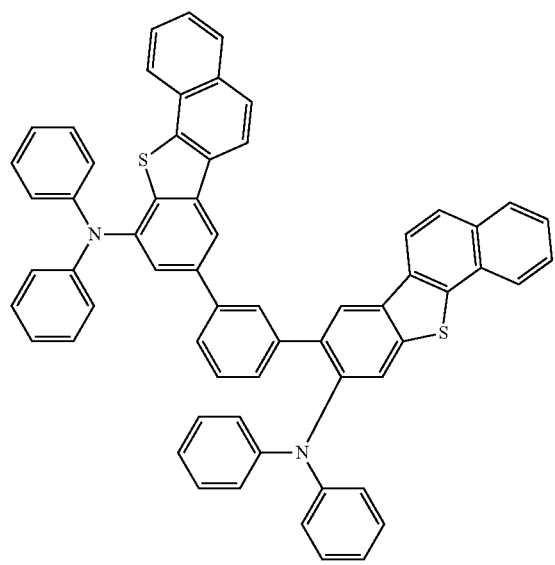
P-89
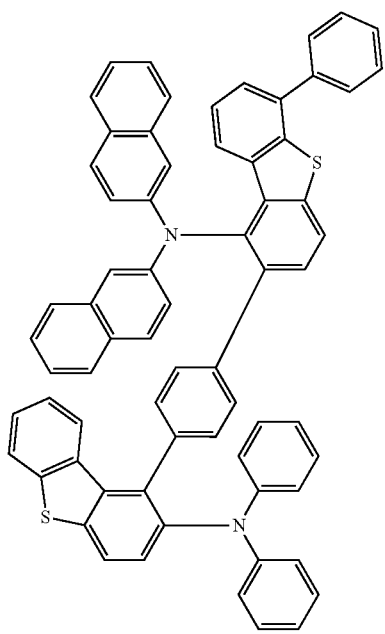

P-90

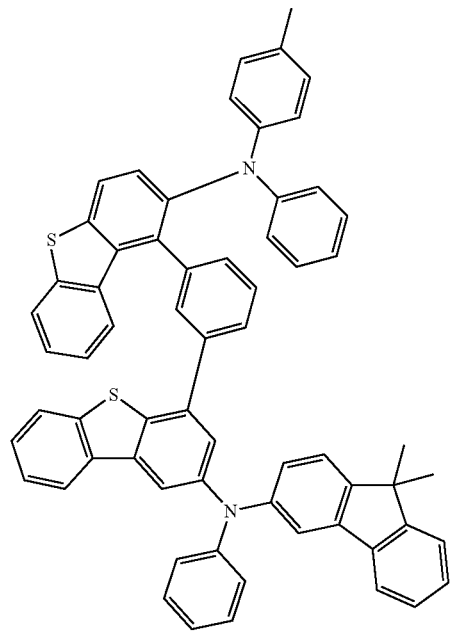

P-91

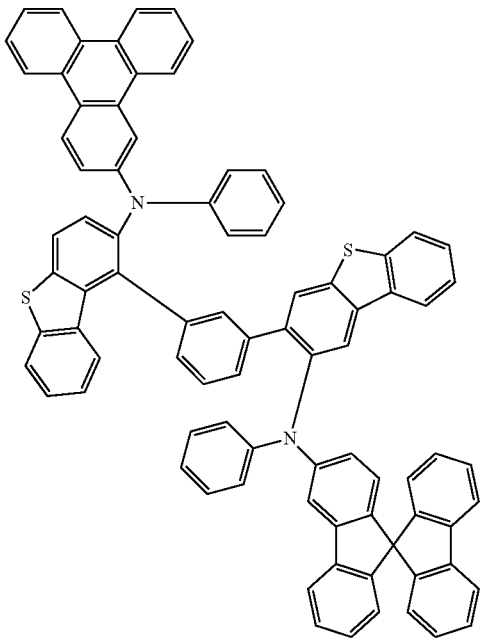

P-92

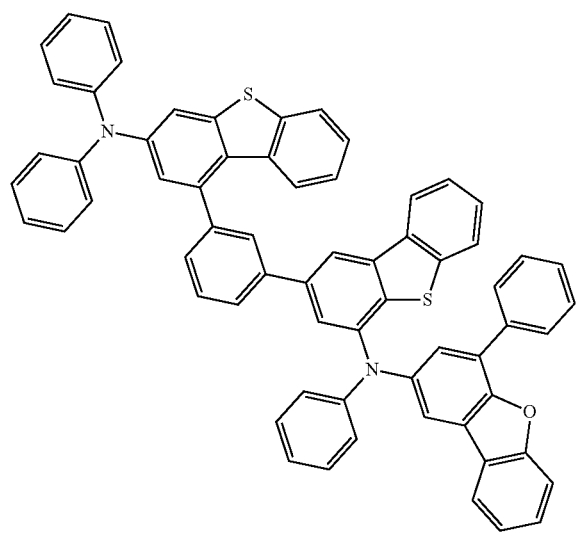

P-93

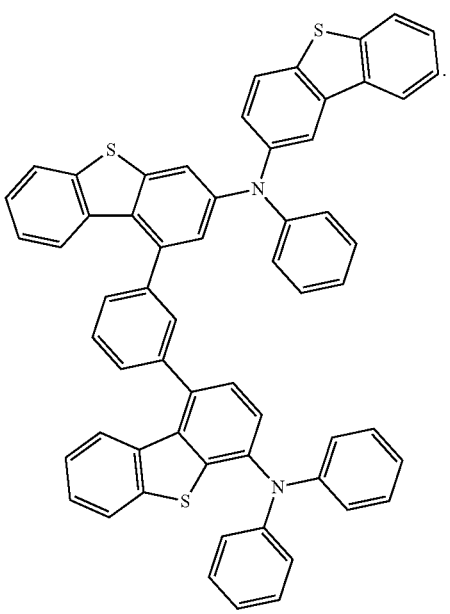

6. An organic electric element comprising a first electrode, a second electrode, and an organic material layer formed between the first electrode and the second electrode, wherein the organic material layer comprises the compound of Formula 1 of claim 1.

7. The organic electric element of claim 6, wherein the organic material layer comprises at least one layer of a hole injection layer, a hole transport layer, an emission-auxiliary layer, a light emitting layer, an electron transport auxiliary layer, an electron transport layer and an electron injection layer, and at least one layer of the hole injection layer, the hole transport layer, the emission-auxiliary layer, the light emitting layer, the electron transport auxiliary layer, the electron transport layer and the electron injection layer comprises one or more of the compound of Formula 1.

8. The organic electric element of claim 7, wherein the emission-auxiliary layer comprises the compound.

9. The organic electric element of claim 6, wherein the organic material layer is formed by a process of spin coating, nozzle printing, inkjet printing, slot coating, dip coating or roll-to-roll.

10. An electronic device comprising a display device and a control unit for driving the display device, wherein the display device comprises the organic electric element of claim 6.

11. The electronic device of claim 10, wherein the organic electric element is one of an organic light emitting diode, an organic solar cell, an organic photo conductor, an organic transistor, and an element for monochromatic or white illumination.

* * * * *